US009682078B2

(12) United States Patent
Botchwey, III et al.

(10) Patent No.: US 9,682,078 B2
(45) Date of Patent: Jun. 20, 2017

(54) COMPOSITIONS AND METHODS FOR TISSUE ENGINEERING AND CELL BASED THERAPIES

(75) Inventors: Edward A. Botchwey, III, Charlottesville, VA (US); Mary J. Laughlin, Crozet, VA (US); Kevin R. Lynch, Charlottesville, VA (US); Anusuya Das, Charlottesville, VA (US); Anthony Awojoodu, Burtonsville, MD (US)

(73) Assignee: University of Virginia Patent Foundation, Charlottesville, VA (US)

( * ) Notice: Subject to any disclaimer, the term of this patent is extended or adjusted under 35 U.S.C. 154(b) by 442 days.

(21) Appl. No.: 14/006,053

(22) PCT Filed: Mar. 16, 2012

(86) PCT No.: PCT/US2012/029369
§ 371 (c)(1),
(2), (4) Date: Sep. 18, 2013

(87) PCT Pub. No.: WO2012/129073
PCT Pub. Date: Sep. 27, 2012

(65) Prior Publication Data
US 2014/0094444 A1  Apr. 3, 2014

Related U.S. Application Data

(60) Provisional application No. 61/454,169, filed on Mar. 18, 2011, provisional application No. 61/547,357, filed on Oct. 14, 2011.

(51) Int. Cl.
| A61K 31/137 | (2006.01) |
| A61K 31/395 | (2006.01) |
| A61K 31/495 | (2006.01) |
| A61K 45/06 | (2006.01) |
| A61K 31/4164 | (2006.01) |
| A61K 31/135 | (2006.01) |
| A61K 31/66 | (2006.01) |

(52) U.S. Cl.
CPC .......... *A61K 31/495* (2013.01); *A61K 31/135* (2013.01); *A61K 31/137* (2013.01); *A61K 31/395* (2013.01); *A61K 31/4164* (2013.01); *A61K 31/66* (2013.01); *A61K 45/06* (2013.01)

(58) Field of Classification Search
None
See application file for complete search history.

(56) References Cited

U.S. PATENT DOCUMENTS

| 2007/0190023 | A1  | 8/2007 | Battista et al. |
| 2009/0062238 | A1* | 3/2009 | Lynch |
| 2010/0003224 | A1  | 1/2010 | Bridger et al. |
| 2011/0044997 | A1  | 2/2011 | Rankin et al. |

FOREIGN PATENT DOCUMENTS

| WO | WO 2008019371     | 2/2008  |
| WO | WO 2008/075369    | 6/2008  |
| WO | WO 2009/074969 A2 * | 6/2009  |
| WO | WO 2010118298     | 10/2010 |

OTHER PUBLICATIONS

Juarez, J., et al., "Chemokines and their Receptors as Therapeutic Targets: The Role of the SDF-1/CXCR4 Axis", Current Pharmaceutical Design, 2004, 10, 1245-1259.
Cyster, J.G., "Chemokines, Sphingosine-1-Phosphate, and Cell Migration in Secondary Lymphoid Organs", Annual Rev. Immunol., 2005, 23:127-59.
Huang, C., et al., "Local delivery of FTY720 accelerates cranial allograft incorporation and bone formation", Cell Tissue Research, (2012), No. 3, 347:553-566. XP-002717655.
Petrie Aronin, C., et al., "FTY720 Promotes Local Microvascular Network Formation and Regeneration of Cranial Bone Defects", Tissue Engineering, Part A., vol. 16, No. 6, 2010, 1801-1809. XP-002717656.
Sefcik, L., et al., "Selective Activation of Sphingosine 1-Phosphate Receptors 1 and 3 Promotes Local Microvascular Network Growth", Tissue Engineering, Part A., vol. 17., Nos. 5 and 6, 2011, 617-629. XP-002717657.
Kennedy, P., et al., "Characterization of a Sphingosine-1-phosphate Receptor Antagonist", FASEB Journal, vol. 22, Apr. 2008. XP009174960.
Chun, J., et al., "International Union of Basic and Clinical Pharmacology". LXXVIII: Lysophospholipid Receptor Nomenclature, Pharmacological Reviews, Dec. 2010, vol. 62, No. 4, 579-587. XP002717659.
Kimura, T., et al., "The sphingosine 1-phosphate receptor agonist FTY720 su7pports CXCR4-dependent migration and bone marrow homing of human Cd 34 + progenitor cells", Blood, 2004, 103: 4478-4486.

(Continued)

Primary Examiner — Savitha Rao
Assistant Examiner — Gregg Polansky
(74) Attorney, Agent, or Firm — Rodney L. Sparks

(57) ABSTRACT

The present application discloses strategies to recruit and mobilize stem cells using S1P receptor selective agonists and antagonists as wells as regulators of chemokine receptors. In an in vivo ischemic model, $S1P_1/S1P_3$ activation with FTY720 impeded inflammatory cell infiltration and recruited endothelial progenitor cells (EPCs) with the potential to increase microvascular remodeling. $S1P_3$ expression on marrow-derived cells was essential for this remodeling. Concurrent systemic $S1P_3$ and CXCR4 antagonism mobilized hematopoietic stem cells (HSCs) with the ability to engraft and repopulate blood cells. Pre-treatment of donor HSCs with FTY720 increased homing toward SDF-1 and improved engraftment in marrow. FTY720-coated bone allografts coupled with systemic administration of VPC01091 enhanced bone allograft integration and new bone formation in bone defects. MSCs pre-treated with FTY720 exhibited increased migration toward SDF-1, a CXCR4+ ligand. The results show that S1P is a very powerful role player in pharmacological marrow-derived stem cell mobilization and recruitment.

27 Claims, 40 Drawing Sheets

(56) References Cited

OTHER PUBLICATIONS

Miron, V. E., et al., "FTY720 Modulates Human Oligodendrocyte Progenitor Process Extension and Survival", Annals of Neurology, vol. 63, No. 1, Jan. 2008, 61-71.

Kucia, M., et al., "Trafficking of Normal Stem Cells and Metastasis of Cancer Stem Cells Involve Similar Mechanisms: Pivotal Rose of the SDF-1-CXCR4 Axis", Stem Cells 2005:23:879-894.

Ryser, M.F., et al., "S1P1 overexpression stimulates S1P-dependent chemotaxis of human CD34+ hematopoietic progenitor cells but strongly inhibits SDF-1/CSCR4-dependent migration and in vivo living", Molecular Immunology 46 (2008) 166-171.

Honig, S.M., et al., "FTY720 stimulates multidrug transporter-and cysteinyl leukotriene-dependent T cell chemotaxis to lymph nodes", The Journal of Clinical Investigtion, Mar. 2003, vol. 111, No. 5, 627-637.

Seitz, G., et al., "The Role of Sphingosine 1-Phosphate Receptors in the Trafficking of Hematopoietic Progenitor Cells", Ann. N.Y. Acad. Sci. 1044: 84-89 (2005).

Myat Lin Oo, et al., "Immunosuppressive and Anti-angiogenic Sphingosine 1-Phosphate Receptor 1 Agonists Induce Ubiquitinylation and Proteasomal Degradation of the Receptor", Journal of Biological Chemistry, vol. 282, No. 12, Mar. 23, 2007, 9082-9089.

Paganessi, L.A., et al., "Effective mobilization of hematopoietic progenitor cells in G-CSF mobilization defective CD 26 −/− mice through AMD3100-induced disruption of the CSCL12-CXCR4 axis", Experimental Hematology 2011:39:384-390.

Song, C., "CXCR4 and matrix metalloproteinase-2 are involved in mesenchymal stromal cell homing and engraftment to tumors", Cytotherapy, 2010: Early Online, 1-13. Epub Online Dec. 20, 2010.

Laschke, M.W., et al., "Endothelial progenitor cells contribute to the vascularization of endometriotic lesions", Abstract, Am J Pathol. Jan. 2011:178(1):442-50. Epub Dec. 23, 2010.

Kim, Ha-Yon, et al., "The CXCR4 Antagonist AMD3100 Has Dual Effects on Survival and Proliferation of Myeloma Cells In Vitro", Cancer Res. Treatment 2010:42(4):225-234, Epub. Dec. 31, 2010.

Singh, V.K., et al., "Mobilized progenitor cells as a bridging therapy for radiation casualties: A brief review of tocopherol succinate-based approaches", Int. Immunopharmacol (2011), doi:10.1016/j.intimp.2011.01.017, 1-6.

Gouwy, M., et al., "CXCR4 and CCR5 ligands cooperate in monocyte and lymphocute migration and in inhibition of dual-tropic (R5/X4) HIV-1 infection", Eur. J. Immunol. 2011. 41: 1-11.

* cited by examiner

| | Inflammatory Monocytes | Anti-Inflammatory Monocytes | EPC-derived Endothelial Cells | Hematopoietic Stem Cells |
|---|---|---|---|---|
| Lin1 | + | + | + | - |
| C-kit | - | - | - | + |
| Sca-1 | - | - | Low | + |
| CD45 | + | + | + | - |
| CD11B | + | + | + | - |
| CD105 | - | - | + | - |
| CX3CR1 | Low | High | High | - |
| Ly6C | High | Low | - | - |

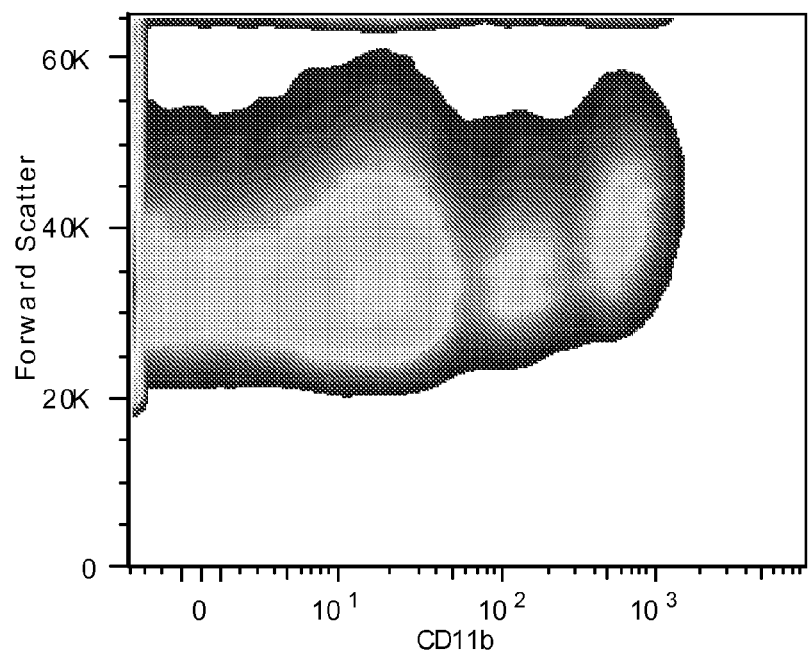
Figure 6C2
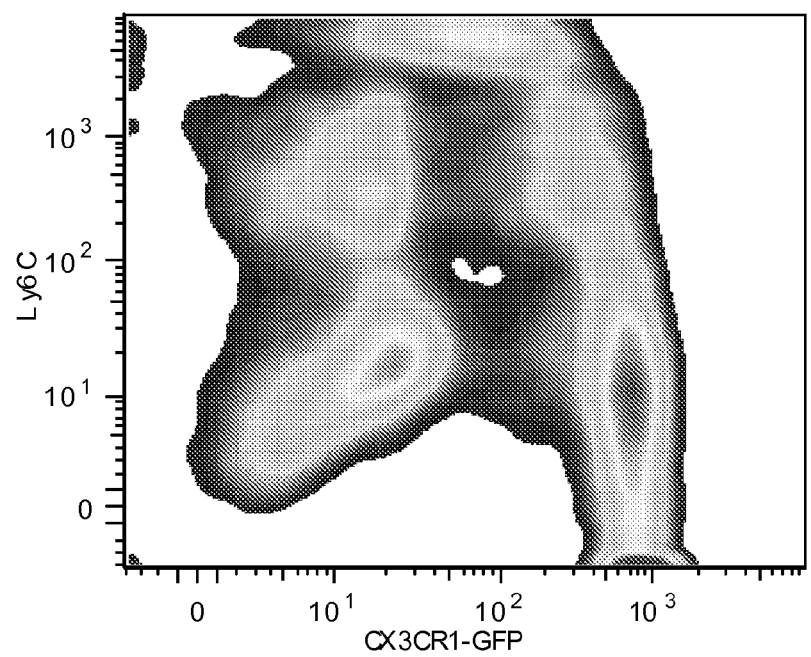
Figure 6C3

Figure 6C4
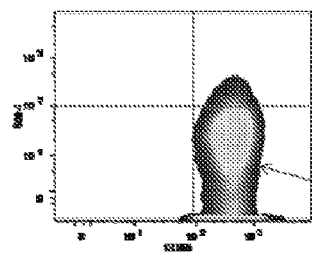
PM: Plain Media, AM: Anti-inflammatory monocyte, IM: Inflammatory monocyte, EPC-EC: Endothelial progenitor cell-derived endothelial cell
Figure 6D
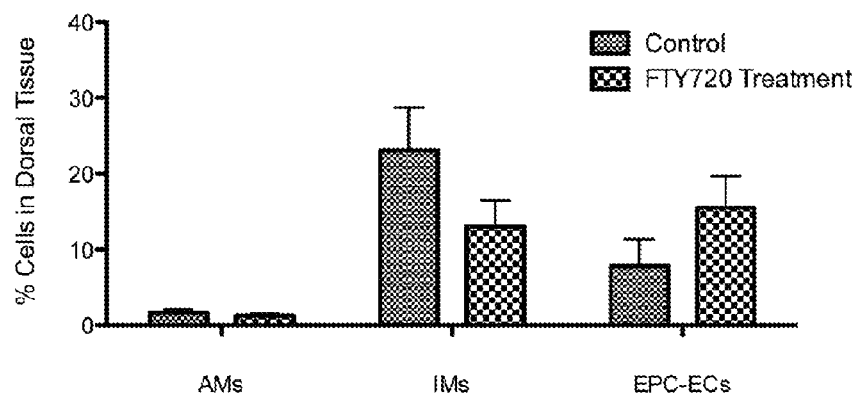

A

B

C

D

E

F

A

B

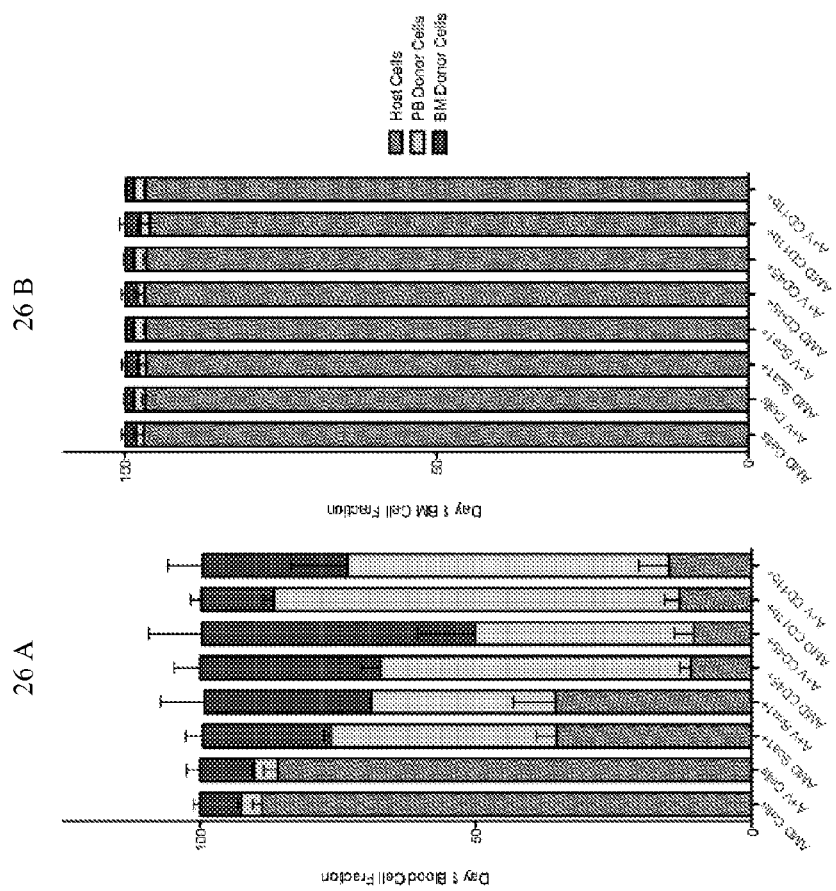
Figure 26 (A and B)

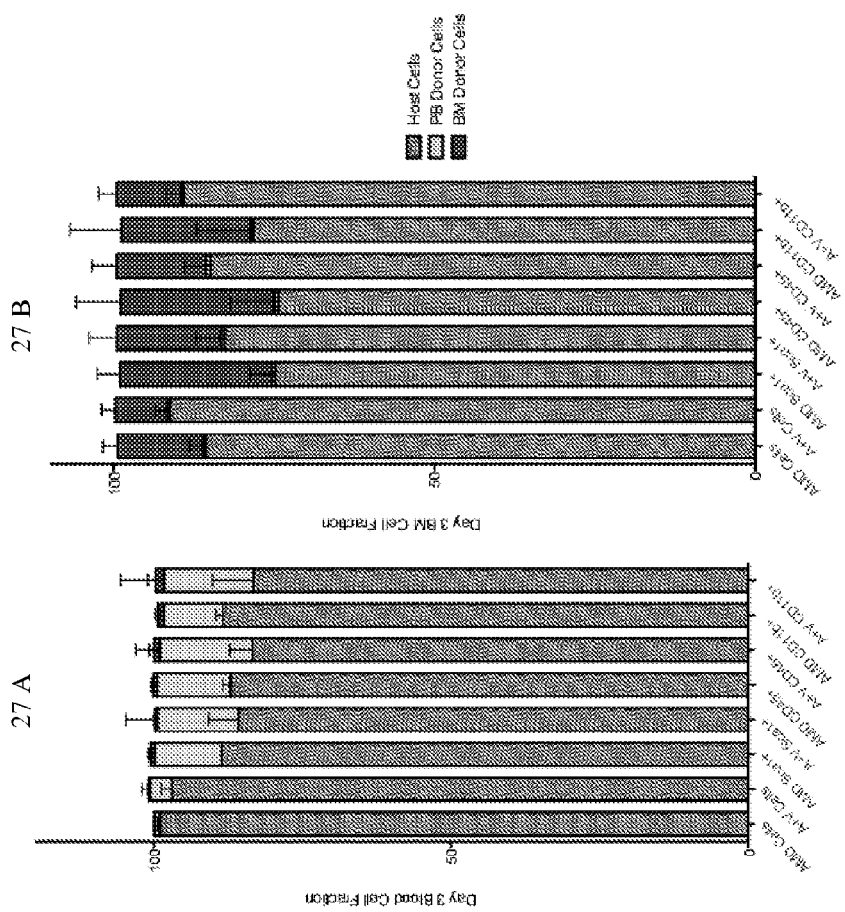
Figure 27 (A and B)

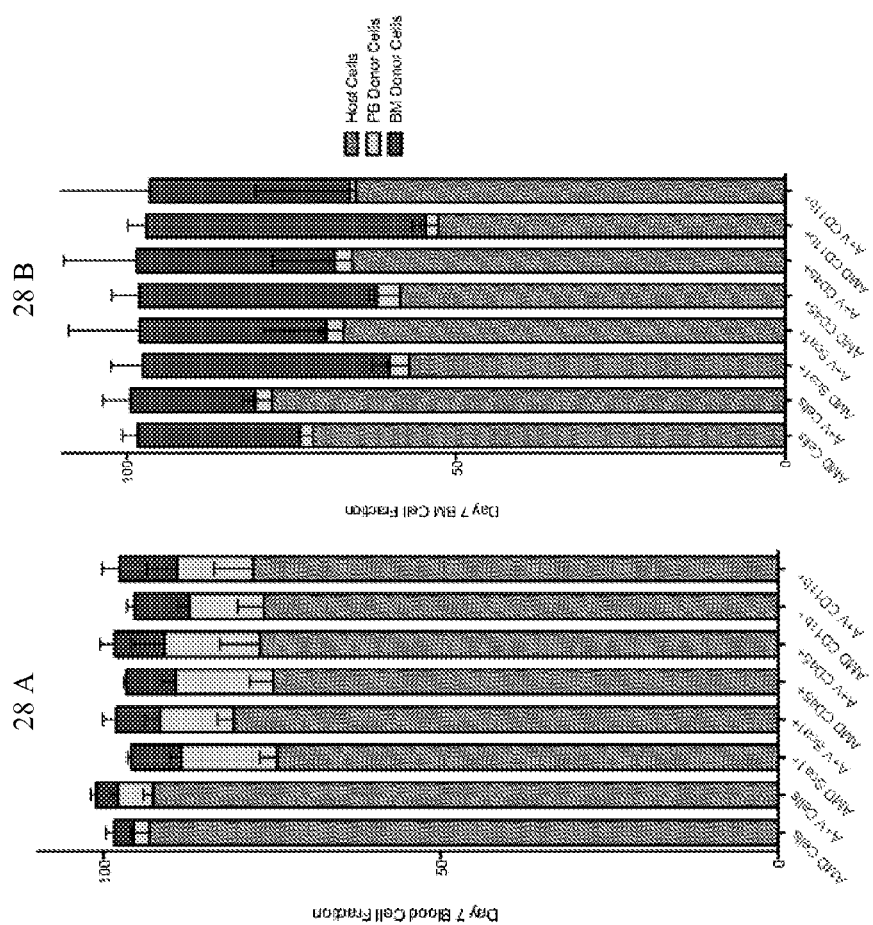
Figure 28 (A & B)

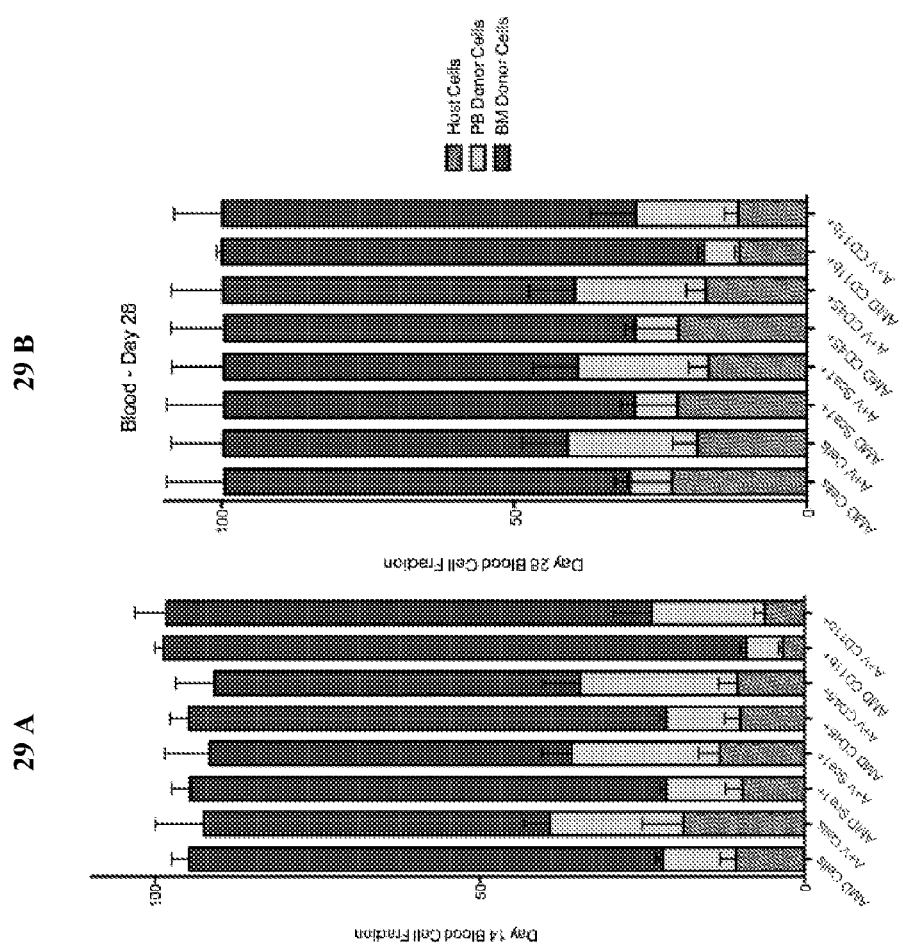
Figure 29 (A & B)

COMPOSITIONS AND METHODS FOR TISSUE ENGINEERING AND CELL BASED THERAPIES

CLAIM OF PRIORITY

This application is a U.S. National Stage Filing under 35 U.S.C. 371 from International Patent Application Serial No. PCT/US2012/029369, filed Mar. 16, 2012, and published on Sep. 27, 2012 as WO 2012/129073 A1, which claims the benefit of priority to U.S. Provisional Patent Application No. 61/454,169, filed Mar. 18, 2011, and which claims the benefit of priority to U.S. Provisional Patent Application No. 61/547,357, filed Oct. 14, 2011, the contents of each of which are hereby incorporated by reference in their entireties.

STATEMENT REGARDING FEDERALLY SPONSORED RESEARCH OR DEVELOPMENT

This invention was made with government support under Grant Nos. 1R01DE019935-01 and 1R01AR056445-01A2 awarded by the National Institutes of Health. The government has certain rights in the invention.

BACKGROUND

S1P Receptor Targeted Drugs

S1P is an autocrine and paracrine signaling small molecule that impacts proliferation, survival and migration of endothelial cells, mural cells (i.e. vascular smooth muscle cells and pericytes), osteoblasts, and osteoblastic precursors through a family of high-affinity G protein-coupled receptors (S1P1-5). Selectively targeting a subset of S1P receptors with agonists and antagonist compounds (with longer bioactive half-lives than native S1P in vivo), one can control different biological responses. For example, recent reports suggest selective activation of $S1P_1$ and $S1P_3$ receptors via a synthetic analog of S1P, FTY720, promotes the recirculation of osteoclast precursor monocytes from the bone surface, an effect that ameliorates bone loss in models of postmenopausal osteoporosis. Furthermore, FTY720 treatment demonstrates enhanced CXCR4-mediated migration of endothelial progenitor cells and homing of bone marrow progenitors in hindlimb ischemia models. Recent discoveries of smooth muscle cell phenotype regulation in large arteries suggest possible synergies between $S1P_1$ receptors and S1P3 receptors, both targets of FTY720. Specifically, daily injections of $S1P_1/S1P_3$ antagonist (VPC44116) significantly decreased smooth muscle proliferation and migration. Thus, FTY720 as a single bioactive factor has multiple cellular targets making it an attractive molecule for strategies to improve graft-host integration where multiple biological processes can be simultaneously augmented to address a central limitation, poor vascularization.

It has been shown that sustained release of FTY720 from two-dimensional biodegradable films (1:200 wt/wt) of 50:50 poly-lactic-co-glycolic acid (PLAGA) in the mouse dorsal skinfold window chamber promotes formation of new arterioles and structural enlargement of existing arterioles. This pattern of FTY720-induced microvascular remodeling increases the number and diameter of microvessels, a therapeutic response that is critical for successful integration of allograft implants in vivo. In addition, implantation of 3D PLAGA scaffolds delivering FTY720 to critical size calvarial bone defects significantly increases osseous tissue ingrowth and the proportion of mature smooth muscle cell-invested microvessels within the bony defect.

The G-protein coupled signaling pathway of S1P receptors has been shown to enhance cell motility, proliferation, and survival due to S1P stimulation. S1P is secreted by several types of cells including mast cells, macrophages, platelets, and endothelial cells into the blood flow in nanomolar plasma concentrations. In areas of endothelial injury, a higher concentration of S1P is released by activated platelets to aid in wound healing. Thus, S1P is thought to possess significant angiogenic and arteriogenic properties including mural cell recruitment to newly-formed vessels and stimulation of SMC differentiation, proliferation, and migration. S1P also reduces oxygen and nutrient-deprived cell death.

Fingolimod (FTY720) is a synthetic compound that acts as an agonist of the $S1P_1$, $S1P_3$, $S1P_4$, and $S1P_5$ receptors when phosphorylated into FTY720P. Due to its structural similarity with S1P, FTY720 shares many of the effects of natural S1P and thus acts as S1P analog. FTY720 was shown to stimulate the angiogenic activity and neovascularization of cultured cells. Other studies have shown that FTY720 prolongs allograft survival by preventing perivascular inflammation associated with chronic transplant rejection. Additionally, due to FTY720's rapid initial adsorption and exceptionally long half-life of approximately 7 days, the blood concentration of FTY720 remains relatively stable after administration. Native S1P, on the other hand, is insoluble in aqueous solutions in the absence of a carrier protein and its half-life in blood is less than 1 hour. Therefore, FTY720 may be a more potent therapeutic agent than S1P. Another S1P analog, VPC01091, also interacts with S1P receptors, but has the unusual property of being an agonist for $S1P_1$ receptor and an antagonist for $S1P_3$ receptor.

Sphingosine-1-phosphate (S1P) has been demonstrated to induce many cellular effects, including those that result in platelet aggregation, cell proliferation, cell morphology, tumor-cell invasion, endothelial cell chemotaxis and endothelial cell in vitro angiogenesis. For these reasons, S1P receptors are good targets for therapeutic applications such as wound healing and tumor growth inhibition.

Sphingosine-1-phosphate signals cells in part via a set of G protein-coupled receptors named $S1P_1$, $S1P_2$, $S1P_3$, $S1P_4$, and $S1P_5$ (formerly Edg-1, Edg-5, Edg-3, Edg-6, and Edg-8, respectively). These receptors share 50-55% identical amino acids and cluster with three other receptors (LPA1, LPA2, and LPA3 (formerly Edg-2, Edg-4 and Edg-7)) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Biodegradation of S1P most likely proceeds via hydrolysis by ectophosphohydrolases, specifically the sphingosine 1-phosphate phosphohydrolases.

Angiogenesis

Orthopaedic regenerative medicine has focused on remodeling the microvascular network to prevent ischemia and aid in nutrient and oxygen delivery to sites of injury. An important process which has held great attention in the biomedical arena is angiogenesis. Angiogenesis refers to the growth of new blood vessels, specifically the sprouting of new capillaries from pre-existing vessels which produce new capillary networks. More than four billion dollars have been invested in research and development for angiogenesis based-medicines, establishing this field of study as one of the most heavily funded in history. Additionally, approximately 314 million patients in Western nations can benefit from angiogenesis-stimulating therapies. Hence, it is essential to understand this process and components involved.

In the initial stage of angiogenesis, diseased or injured tissues produce and release growth factors which diffuse into tissues within close proximity. Some of these factors include vascular endothelial growth factor (VEGF), platelet-derived growth factor (PDGF), epidermal growth factor, granulocyte colony-stimulating factor, hepatocyte growth factor, transforming growth factor alpha, and several others. These proteins then bind to and activate specific receptors on endothelial cells. Upon activation, signal pathways are initiated in the endothelial cells which facilitate the production of enzymes. These enzymes create dissolved holes in the basement membrane of existing blood vessels. Endothelial cells then begin to proliferate and subsequently migrate via the dissolved holes of the blood vessels. Next, adhesion molecules, or integrins ($\alpha v \beta 3$, $\alpha v \beta 5$), facilitate the pulling of new blood vessel sprouts forward. Additional enzymes, called matrix metalloproteinases (MMPs), are created to dissolve the tissue in front of the sprouting vessel tip. These MMPs ensure that as the vessel extends, the tissue is remodeled around the vessel. Blood vessel tubes then begin to form due to sprouting endothelial cells. Once formed, these individual tubes connect to existing blood vessels to create blood vessel loops which can circulate blood. To ensure these newly formed blood vessel tubes are stabilized and functional, smooth muscle cells and pericytes are recruited and provide structural support, essentially allowing blood flow to occur.

Three different processes may contribute to the growth of new blood vessels: vasculogenesis, arteriogenesis, and angiogenesis. Vasculogenesis is the primary process responsible for growth of new vasculature during embryonic development and may play a yet-undefined role in mature adult tissues. It is characterized by differentiation of pluripotent endothelial cell precursors (hemangioblasts or similar cells) into endothelial cells that go on to form primitive blood vessels. Subsequent recruitment of other vascular cell types completes the process of vessel formation. The occurrence of vasculogenesis in mature organisms remains an unsettled issue. It is thought to be unlikely that this process contributes substantially to the new vessel development that occurs spontaneously in response to ischemia or inflammation as a response to growth factor stimulation.

Arteriogenesis refers to the appearance of new arteries possessing a fully developed tunica media. The process may involve maturation of pre-existing collaterals or may reflect de novo formation of mature vessels. Examples of arteriogenesis include formation of angiographically visible collaterals in patients with advanced obstructive coronary or peripheral vascular disease. All vascular cell types, including smooth muscle cells and pericytes, are involved. Arteriogenesis is the preferred type of neovascularization for purposes of restoring myocardial perfusion. Native arterial collateralization is a complex process that involves multiple levels of stimulators, inhibitors, and modulators. Therefore, the discovery of a drug molecule that induces therapeutic arteriogenesis, including the self-propagating cascade of proliferation, migration, and chemotaxis would be useful.

Angiogenesis is the process responsible for formation of new vessels lacking developed media. Examples of angiogenesis include capillary proliferation in wound healing or along the border of myocardial infarction. Angiogenesis can be stimulated by a number of growth factors including fibroblast growth factor-2 (FGF-2) and vascular endothelial growth factor (VEGF). Further, insulin-like growth factor-I (IGF-I) can stimulate proliferation of these cells and can induce VEGF secretion. These growth factors appear to exert their effort directly on endothelial cells and reports indicate that these effects may be mediated through specific integrin molecules ($\alpha v \beta 3$ or $\alpha v \beta 5$).

The occurrence of both angiogenesis and arteriogenesis has been demonstrated conclusively in a variety of animal models, as well as in patients with coronary disease. Thus, insufficient angiogenesis may lead to tissue ischemia and failure. The recent discovery of novel angiogenic molecules has initiated efforts to improve tissue perfusion via therapeutic angiogenesis. However, rational design of novel treatment strategies and potential drugs mandates a better understanding of the molecular mechanisms of angiogenesis.

Hematopoietic Stem Cells

Hematopoietic stem cells are multipotent stem cells that give rise to all the blood cell types including human CD34+ stem cell. The CD34 molecule is a cluster of differentiation molecules present on certain cells within the human body. It is a cell surface glycoprotein and functions as a cell-cell adhesion factor. It may also mediate the attachment of stem cells to bone marrow extracellular matrix or directly to stromal cells. CD34 is also the name for the human gene that encodes the protein.

Cells expressing CD34 (CD34+ cell) are normally found in the umbilical cord and bone marrow as hematopoietic cells and tend to migrate from the blood stream to the bone marrow along a gradient of stromal derived factor-1 (SDF-1) where SDF-1 levels are high in the bone marrow and low in the peripheral blood. SDF-1 is a cytokine belonging to the chemokine family CXCL12. When a bone marrow transplant patient receives allogeneic UCB mononuclear cells via intravenous infusion, successful engraftment entails UCB stem cells taking up residence in the patient's bone marrow. A peripheral blood mononuclear cell is any blood cell having a round nucleus. Activation of the complement system in the transplant patient as part of the stress response elicited by chemoradiotherapy conditioning activates proteases in the marrow that reduce SDF-1 concentration. Low SDF-1 levels in the bone marrow tend to lessen homing and engraftment of allogeneic UCB CD34 stem cells. Because the numbers of CD34+ hematopoietic stem cells (HSC) in UCB is low, methods to enhance engraftment of this population of cells are needed. Non-embryonic UCB-derived stem cells are non-controversial (with approval by the Vatican and all religious groups), and offer the potential for "off the shelf" cell therapeutic products that are easier to obtain and faster to distribute than cumbersome individual adult directly-donated bone marrow and blood cells.

AMD3100 is a small-molecule CXCR4 chemokine antagonist known to enhance mobilization of stem cells for autologous transplantation in patients with non-Hodgkin's lymphoma (NHL) and multiple mycloma (MM). It is also used in some cases in conjunction with G-CSF administration, but must be administered at least several days later. AMD3100 is an inhibitor of the interaction between stromal cell-derived factor 1 (SDF-1) and its receptor CXCR4.

Limitations of current management of vascular disease include re-occlusion and diffuse small vessel disease. Prior evidence links the level of circulating marrow-derived HSC, characterized by expression of CD133 and CD34, with the occurrence of ischemic vascular events. Human HSC which express CD34 and CD133 surface markers have been shown in models of acute and chronic ischemia to augment blood flow and prevent myocardial necrosis There is emerging evidence of age-related diminution in the number and function of marrow-derived CD34/133+ HSC in response to ischemia.

Cellular and molecular mechanisms underlying homing to the marrow microenvironment, a key requirement for successful allogeneic transplantation, is incompletely characterized. Data acquired to date indicates that administration of required patient pre-conditioning with chemoradiotherapy prior to allogeneic donor HSC infusion causes a stress response, including S1P release from circulating red blood cells (RBC) in the peripheral blood; and simultaneous release of proteases in the marrow that diminish SDF-1 concentrations. These two biologic sequelae of the stress response in vivo normally maximize egress of HSC out of the marrow niche.

S1P has been shown by this group and others to act on human CD34+ HSC or murine Lineage 1−/Sca1+/c-kit+ (LSK) as a chemotactic factor in the peripheral blood, mediating egress of HSC from the marrow. Furthermore, activation of S1P receptors augments CXCR4-mediated signal transduction induced by SDF-1. These effects are most likely mediated by both the $S1P_1$ and $S1P_3$ receptors expressed on both primitive and committed CD34+ HSC. SDF-1 regulates the trafficking of HSC. SDF-1 is the ligand for CXCR4, which had been considered for many years as its only receptor. Thus, the SDF-1-CXCR4 axis has a unique and important biological role.

Polymers

Poly (D, L-lactic-co-glycolic acid) (PLAGA) and poly(3-hydroxybutrate-co-3-hydroxyvalerate) (PHBV) are biodegradable and biocompatible polymers commonly used for tissue-engineered scaffolds. One can tailor the degradation rate of these polymers by altering the ratio of each component in the polymer composition, thereby rendering them suitable drug-release devices for both local and systemic delivery.

PLAGA is an FDA-approved copolymer of polylactide (PLA) and polyglycolide (PGA). PLA is a hydrophobic material with a degradation time greater than 24 months, which allows for great drug delivery potential. Through metabolic pathways, PLA degrades to lactic acid. PGA is a hydrophilic material and degrades at a faster rate, typically between 6 and 12 months, resulting in the glycolic acid byproduct. The polyester PLAGA degrades through hydrolysis and exhibits bulk degradation, releasing the non-toxic byproducts lactic acid and glycolic acid. Because of these acidic byproducts, local pH changes must be considered during PLAGA degradation. When used as a drug-delivery vehicle, variables such as molecular weight (Mw), copolymer composition, and crystallinity influence polymer degradation and the corresponding drug release kinetics.

PHBV is a polyester copolymer of hydroxybutyrate and hydroxyvalerate with adjustable processing and mechanical properties. By altering the copolymer composition and Mw, one can modify properties of PHBV. The accumulation of degradation products β-hydroxybutyric acid and hydroxyvaleric acid can thus be controlled.

There is a long felt need in the art for compositions and methods to enhance wound healing, organ and tissue repair, and mobilization and recruitment of stem and progenitor cells. The present invention satisfies these needs.

SUMMARY OF THE INVENTION

The present invention provides compositions and methods useful for tissue engineering and cell based therapy applications. The present invention is based on the discovery described herein of the role of sphingosine 1-phosphate (S1P) and its receptors in recruiting and mobilizing cells, especially various kinds of stem and progenitor cells, while at the same time inhibiting the recruitment of inflammatory cells. The present invention is further based on the disclosure provided herein that $S1P_3$ expression on marrow-derived cells is essential for microvascular growth and remodeling.

The present invention further discloses compositions and methods for simultaneous regulation of S1P receptors, both positive and negative, as well as the chemokine receptor CXCR4. That is, concurrent pharmacological inhibition of CXCR4 and S1P receptors significantly mobilizes hematopoietic stem cells into circulation with the ability to engraft in the host and repopulate blood cells. In one aspect, the present invention provides compositions and methods to enhancement engraftment. In one aspect, the present invention provides compositions and methods useful for stimulating the repopulation of blood cells.

The present invention encompasses the use of combinations of regulators of the S1P receptors and CXCR4. In one aspect, the compounds are S1P agonists, and in another aspect, S1P antagonists. The present invention therefore encompasses the use of compounds such as FTY720, AMD3100, and VPC01091, and derivatives, analogs, and homologs thereof with the activities described herein.

In one aspect, the compound AMD3100 is useful in the practice of the present invention. AMD3100 has the structure:

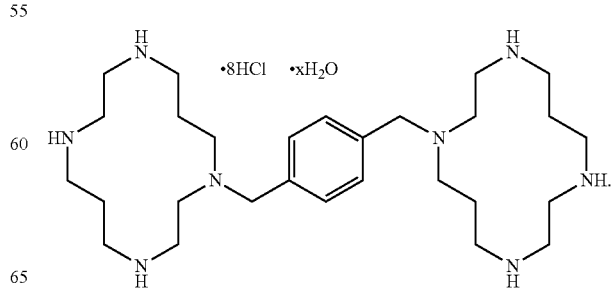

It has been shown, for example, that AMD3100 can mobilize hematopoietic stem and progenitor cells (Paganessi et al., Exp. Hematol., 2011, March; 39(3):384-90; Epub 2010 Dec. 17). AMD3100 is also known to be an antagonist of CXCR4 and is known to differentially regulate migration of bone marrow-derived mesenchymal stromal cells toward different tumor cells (Song and Li, Cytotherapy, 2011 May; 13(5):549-61. Epub 2010 Dec. 20). AMD3100 has other regulatory abilities as wall (sec, for example, Kim et al., Cancer Res Treat. 2010 December; 42(4):225-34. Epub 2010 Dec. 31 and Singh et al., Int. Immunopharmacol. 2011 July; 11(7):842-47. Epub 2011 Feb. 3). The present invention, therefore, encompasses the use of other compounds with CXCR4 modulatory activity.

The present invention encompasses the use of FTY720 (fingolimod), and active analogs thereof:

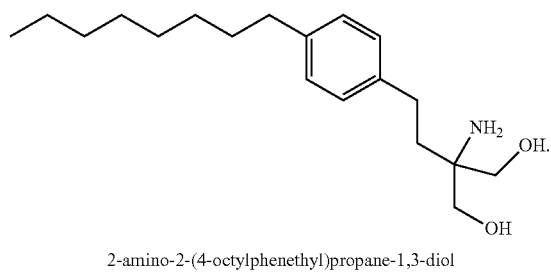 [SMILES: CCCCCCCCc1ccc(CCC(N)(CO)CO)cc1]

2-amino-2-(4-octylphenethyl)propane-1,3-diol

The immunomodulator FTY720, (2-amino-2-[2-(4-octylphenyl)ethyl]propane 1,3-diol), following phosphorylation, is an agonist at 4 of 5 S1P receptors. VPC01091 is an $S1P_1$ agonist, but an $S1P_3$ antagonist.

The present invention encompasses the use of compounds such as VPC01091 (1-amino-3-(4-octylphenyl)cyclopentyl) methanol), including all isomers and racemates, as well as analogs, derivatives and homologs thereof. The compound can be found in U.S. Pat. Nos. 7,754,703 and 8,008,286 and has the following structure:

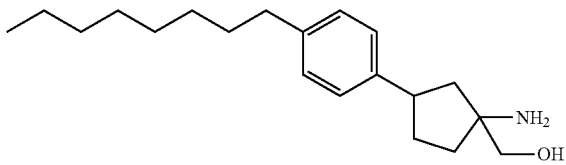 [SMILES: CCCCCCCCc1ccc(C2CCC(N)(CO)C2)cc1]

VPC01091.

VPC01091 has two chiral centers (the quaternary carbon and benzylic carbon that is part of the cyclopentyl ring) and thus four isomers (diastereomers) are conceivable. VPC01091 is a mixture of these four isomers but the relative amount of each isomer is not known, but available evidence indicates that the four isomers are present in about equal amounts. The individual isomers, A-D, have the formulas:

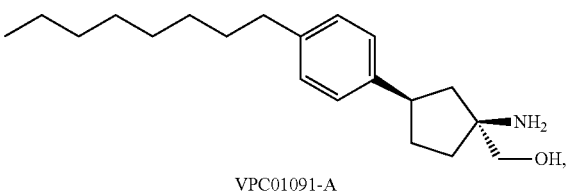

VPC01091-A

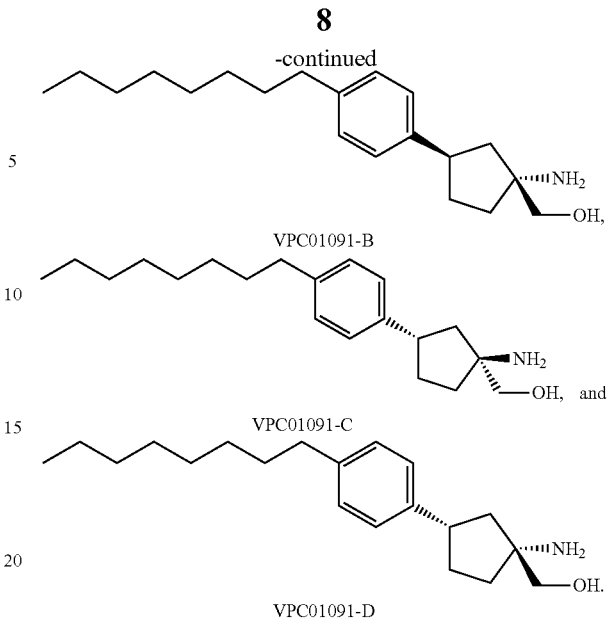

VPC01091-B

VPC01091-C

VPC01091-D

These compounds can be prepared as a mixture and separated by chromatography. Exemplary conditions for separation are as follows: Column: Chiralpak AD 4.6 mm ID×250 mm, Mobile Phase: Hex/EtOH/MeOH/DEA=95/2.5/2.5/0.03, Flow Rate: 1 mL/min, Detector: UV 220 nm, Column Temp: 40° C., or Column Temp: 25° C.

Another useful compound of the invention is VPC01211, having the structure:

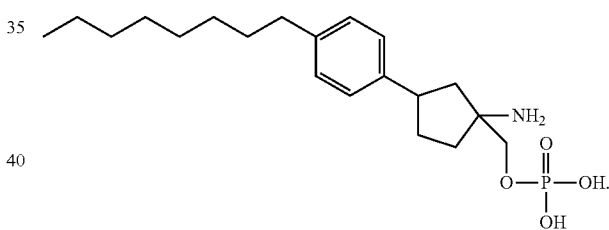

VPC01211 can be found in U.S. Pat. No. 8,008,286 (Lynch et al). Other useful compounds of U.S. Pat. No. 8,008,286 include VPC02162, VPC02164, VPC02004, VPC02007, VPC02031, VPC02033, VPC01289, VPC01292, VPC01220, VPC01222, VPC01212, and VPC01214.

Other useful compounds and methods that can be practiced with the methods of the invention can be found in Lynch et al. (U.S. Pat. No. 8,008,286), Botchwey et al. (WO 2010/118298) and Lynch et al. (U.S. Pat. No. 7,754,703), and other publications cited herein.

It is disclosed herein that FTY720 inhibits inflammatory cell infiltration and recruits stem/progenitor cells locally (See Example 1). It is disclosed herein that local $S1P_1/S1P_3$ activation prevents inflammatory cell recruitment and promotes microvascular remodeling through BMCs. It is also disclosed herein that FTY720 enhances tortuosity and vessel remodeling in ischemic environments and recruits CX3CR1+ cells to vessels.

The unexpected result is disclosed herein that concurrent pharmacological inhibition of CXCR4 and $S1P_3$ significantly mobilizes hematopoietic stem cells into circulation with the ability to engraft in the host and repopulate blood cells. Pre-treatment of a subject with FTY720 enhances this engraftment. Modulation of the S1P receptor-signaling axis may be a novel therapeutic strategy for the selective in situ mobilization and recruitment of stem cells for tissue engineering and stem cell based therapies. For example, it is disclosed in Example 1 that pre-sorted $CD45^+/CD11b^+/Ly6C^{low}/CX3CR1^{high}$ anti-inflammatory monocytes (AM) and $CD45^+/CD11b^+/Ly6C^{high}/CX3CR1^{low}$ inflammatory monocytes (IM), when pre-treated with FTY720, resulted in increased migration of AMs toward SDF-1, but decreased the migration of IMs toward SDF-1 and S1P. The recruitment of IMs into the in vivo tissue model was attenuated with local FTY720 application. Cells that are $CD45^|/CD11b^|/Ly6C^{high}/CX3CR1^{low}/CD105^|$ and have a decreasing expression of Sca1 (a progenitor cell marker) are consistent with endothelial progenitor derived endothelial cells (EPC-ECs). EPC-ECs were increased with FTY720 treatment, suggesting a FTY720-dependent recruitment and differentiation of EPCs in the microvasculature. Therefore, local FTY720 stimulation attenuates the infiltration of inflammatory cells and recruits regenerative stem cells. It is further disclosed herein that $S1P_3$ expression on marrow-derived cells is essential for microvascular growth and remodeling, that marrow-derived cells were recruited to sites of microvascular remodeling via $S1P_3$, and that when $S1P_3$ is selectively antagonized on marrow-derived cells there is impaired FTY720-induced microvascular remodeling.

It is further disclosed in Example 1 that concurrent CXCR4 and S1P antagonism promotes marrow cell (BMC) mobilization by abolishing an SDF-1 gradient, by demonstrating that VPC01091 leads to $S1P_3$ antagonism, which decreases the phosphorylation of CXCR4. This, in conjunction with the administration of AMD3100, functionally antagonizes CXCR4, removing the ability of BMCs to respond to SDF-1 gradients. These BMCs include, for example, any cells that express CXCR4 and reside in the bone marrow including $Lin1^-/Sca1^+/c$-kit mouse HSC and $CD11b^-/CD45^-/CD90^+/CD54^+/CD29^+$ rat mesenchymal stem cells (MSC) in our studies. The present application provides for the use of $S1P_3$ receptor antagonists to selectively mobilize stem cells without affecting their ability to engraft and FTY720 enhances SDF-1 homing. This method can be practiced using equivalent cells from other animals, including humans.

Example 2 discloses that S1P receptors modulate endogenous stem cell mobilization and homing to enhance healing, particularly bone healing. It is disclosed herein that pharmacological inhibition of $S1P_3$ receptor using VPC01091 significantly increased mobilization of bone marrow stromal cells into peripheral blood. This results in accelerated bone repair. This demonstrates the effectiveness of this treatment for enhancing wound healing. It is also disclosed that bone marrow stromal cells pre-treated with FTY720 exhibit increased migration toward SDF-1, a CXCR4+ ligand and critical component of the bone marrow niche. It is further disclosed that using FTY720-coated bone allografts coupled with systemic administration of VPC01091 enhances bone allograft integration and new bone formation in the defect region.

The present invention encompasses using $S1P_3$ receptor antagonists to mobilize BMSCs. The present invention further encompasses using $S1P_3$ receptor agonists to enhance stem cell recruitment. The present invention provides for simultaneous use of antagonists and agonists, as well as administration sequentially. Timing of sequential administration can be determined using known methods and as described herein.

In one embodiment, the effectiveness of FTY720, or similar compounds, to promote healing, using, for example, locally released FTY720, is enhanced by recruitment of bone marrow-derived stem cells by regulating the $S1P_3$ receptor. In one aspect, delivery of an $S1P_3$ antagonist stimulates the engagement of the push-pull mechanism of endogenous stem cells. In one aspect, the delivery is systemic. In one aspect, timing of delivery of the $S1P_3$ antagonist effects the amount of stimulation of engagement of the push-pull mechanism of endogenous stem cells. Therefore, the amount of stimulation can be controlled by adjusting the timing of delivery.

The present application further discloses that the rate of bone growth, even large defects, can be regulated and enhanced by administering a combination of S1P receptor specific compounds, agonists and/or antagonists, and that the administration can be timed for optimal effect. The present invention encompasses modulating S1P receptors to enhance stem cell mobilization and homing for bone regeneration.

The present application further discloses the unexpected result of the use of combination therapy comprising administering at least one CXCR4 antagonist and at least one $S1P_1$ agonist/$S1P_3$ antagonist as useful for stem and progenitor cell mobilization and engraftment. In one aspect, AMD3100 and VPC01091 are administered, and optionally FTY720. Timing of administration when two or more different compounds are used can be varied, including administering the compounds separately and administering multiple times. Effective analogs and derivates of these compounds can also be used. In on aspect, a combination of compounds antagonizing $S1P_3$ and CXCR4 enhances the number of stem cells in peripheral blood. In one aspect, the present invention provides for the pre-treatment of donor cells with VPC01091 or other compounds of the invention. Donor cells can include cells from peripheral blood, bone marrow, and umbilical cord blood. In one aspect, administration of a compound is local. In another aspect, administration of a compound can be done systemically.

In one embodiment, regulation of S1P receptor signaling by avoiding signaling on the CXCR4/SDF-1 axis is useful for mobilizing marrow-derived stem cells. In one aspect, the marrow-derived stem cells are mobilized into peripheral blood without affecting their ability to engraft in the host or at the repair site. In one aspect, FTY720 can be used to enhance cell migration toward SDF-1, and abolish chemotaxis toward S1P.

The present invention provides therapies that are better than those being used today. The combination of AMD3100 and VPC01091 as described herein, which can mobilize stem cells without affecting ability to engraft, can be used without the expensive and lengthy temporal process currently used. The current therapy regimen in use comprises administering G-CSF, followed days later by AMD3100. Therefore, the combination disclosed herein is better and quicker.

The present invention provides compositions and methods useful for increasing stem and progenitor cell mobilization, recruitment of cells, and engraftment of cells by using regulators of the $S1P_1$ receptor, $S1P_3$ receptor, and the CXCR4 receptor, alone or in combination. Example 3 discloses that antagonism of the $S1P_3$ receptor significantly increases mobilization of hematopoietic stem cells and that the combination treatment of using an antagonist of the $S1P_3$ receptor and an antagonist of the CXCR4 receptor can significantly increase hemopoietic stem cell mobilization and that activation of the S1P$_3$ receptor with FTY720 can inhibit the increase. Here, hematopoietic stem cells are defined, for example, as murine Lineage1⁻/Sca1⁻/c-kit⁺ cells and/or those cells that when plated on stem cell differentiative media or stromal cells for 6-14 days form colony forming units (CFUs) or cobblestones of multiple lineages. The invention includes the use of analogous cells from other animals. It is also disclosed herein that bone marrow stem cells can be mobilized utilizing the compositions and methods of the invention. The present application further discloses that the combination treatment of AMD3100 with VPC01091 is more effective than AMD3100 alone in mobilizing cells. The compositions and methods of the invention are also useful for enhancing engraftment.

The invention further encompasses the use of donor cells, which can be pre-treated using the various compounds of the invention and then administered to the subject or the cells can be administered to a subject who is then treated with one or more of the compounds of the invention. Donor cells may be derived from the host subject, from another subject, and from umbilical cord blood. Donor cells can also be isolated from blood or other sources. The compositions and methods of the invention are useful, for example, in enhancing cell engraftment and for achieving better transplant outcomes using therapies such as use of donor blood, bone marrow transplants, or use of umbilical cord blood. In one aspect, subjects treated using the compositions and methods of the invention have increased survival compared to subjects receive no treatment or conventional treatments.

In one aspect, a composition of the invention is a pharmaceutical composition. I composition of the invention can includes additional ingredients, including but not limited to additional therapeutic agents and optionally at least one purified antimicrobial agent. In one aspect, a composition of the invention comprising at least one polymer and at least one bioactive agent, such as VPC01091, AMD3100, or FTY720, and the composition can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof.

In one embodiment, the composition is administered to a subject using a method selected from the group consisting of directly, topically, subcutaneously, and parenterally. In one aspect, the composition is administered directly.

In one embodiment, the method enhances angiogenesis.

In one embodiment, the subject is human.

In one embodiment, the compositions and methods of the invention increase the structural integrity of a bone allograft-host bone interface and restore normal bone turnover and remodeling at a defect site. In one aspect, the allograft is pre-coated with a composition comprising FTY720. In one aspect, the composition comprising FTY720 is a polymer composition.

In one embodiment, the compositions and methods of the invention are useful for treating wounds. In one aspect, the wound is a wound or injury to a bone, including from surgery. In one aspect, the method enhances bone healing.

The present invention further provides kits useful for the practice of the invention. In one embodiment, the present invention provides a kit for administering a composition of the invention for treating a wound or for enhancing bone healing. In one aspect, the kit comprises a composition comprising a biologically compatible polymer and at least one S1P receptor selective agonist or antagonist, optionally at least one CXCR4 antagonist, optionally a pharmaceutically acceptable carrier, optionally at least one antimicrobial agent, optionally at least one additional therapeutic agent, an applicator, and an instructional material for the use thereof.

Enhancements of wound healing and bone healing or repair are described herein or are known in the art and include, but are not limited to, increases in bone density, increases in structural integrity of bone allograft-host bone interfaces, and increased deposition of bony tissue at bone allograft-host bone interfaces.

The compositions and methods of the invention are useful on various cell types, including, but not limited to, bone marrow cells, bone marrow-derived stem cells, hematopoietic stem cells, mesenchymal stem cells, progenitor cells, and umbilical cord blood cells. In one aspect, the cells are host cells. In one aspect, the progenitor cells are endothelial cells. The cells of the invention can be isolated or at least partially purified away from the population of cells in which they were obtained.

In one embodiment, a compound of the invention is administered to a subject at a dosage range of about 0.01 mg/kg to about 500 mg/kg per application. In one aspect, the dosage is about 0.1 to about 250 mg/kg. In another aspect, the dosage is about 1.0 to about 100 mg/kg. In yet another aspect, the dosage is about 5.0 to about 50 mg/kg. One of ordinary skill in the art will appreciate that depending on the disease or condition to be treated and on the age, health, and sex of the subject to be treated, that the dosage regimen can be varied. In one aspect, a compound is administered at least twice. In one aspect, at least two compounds are administered. In another aspect, at least three compounds are administered. In one aspect, a compound of the invention is administered at least once a week. In one aspect, a compound of the invention is administered at least once a day.

In one embodiment, when cells are to be administered to a subject the cells can be pre-treated with at least one compound of the invention. In one aspect, cells are pre-treated with a compound at a concentration of about 0.01 nM to about 500 nM. In another aspect, the cells are pre-treated with a compound at a concentration of about 0.1 to about 250 nM. In another aspect, the cells are pre-treated with a compound at a concentration of about 1.0 to about 100 nM. In another aspect, the cells are pre-treated with a compound at a concentration of about 5.0 to about 50 nM. In another aspect, the cells are pre-treated with a compound at a concentration of about 10.0 to about 25 nM. In one aspect, the cells are pre-treated with more than one compound before being administered to the subject.

Various aspects and embodiments of the invention are described in further detail below.

BRIEF DESCRIPTION OF THE DRAWINGS

FIG. 3A: Murine Dorsal Skinfold Window Chamber-1 mm poly(lactic-co-glycolic acid) PLAGA films loaded with S1P receptor compounds are placed within the window chamber as shown. Repeated measurements of the same vessel networks are recorded and quantified over a 7-day time course using intravital microscopy. FIG. 3B: Higher magnification of the chamber.

FIG. 4: Summary of Cell types and Antigens.

FIG. 7 (comprising FIGS. 7A-7C)

FIG. 8: $S1P_3$ Expression on Marrow-Derived Cells is Essential for Microvascular Growth and Remodeling.

FIG. 8A comprises eight panels.

FIGS. 10 (A-E): $S1P_3$ Antagonism Selectively Mobilizes Stem Cells Without Affecting Ability to Engraft and FTY720 Enhances SDF-1 Homing.

FIGS. 26 (A & B): Graphical illustrations that on Day 1 post transplantation most blood and bone marrow cells are still host-derived and have not died from irradiation. There were no significant differences in host concentration of donor-derived blood cells between the two groups. 26A—Blood cell fraction. 26B—BM cell fraction. Host cells, PB donor cells and BM donor cells were tested. Abscissa-AMD cells, A+V cells, AMD Sca1+, A+V Sca1+, AMD CD45+, A+V CD45+, AMD CD11b+, and A+V CD11b+.

FIGS. 27 (A & B): Graphical illustrations that on day 3 post transplantation the dominant cell types are still host-derived but animals with cells mobilized with "AMD3100+ VPC01091" show increased donor content. 27A—Blood cell fraction. 27B—BM cell fraction. Host cells, PB donor cells and BM donor cells were tested. Abscissa—AMD cells, A+V cells, AMD Sca1+, A+V Sca1+, AMD CD45+, A+V CD45+, AMD CD11b+, and A+V CD11b+.

FIGS. 28 (A & B): Graphical illustrations that on day 7 post transplantation the dominant cell types are still host-derived but animals with cells mobilized with AMD3100+ VPC01091 show increased donor content. 28A—Blood cell fraction. 28B—BM cell fraction. Host cells, PB donor cells and BM donor cells were tested. Abscissa—AMD cells, A+V cells, AMD Sca1+, A+V Sca1+, AMD CD45+, A+V CD45+, AMD CD11b+, and A+V CD11b+.

FIGS. 29 (A & B): Graphical illustrations that on day 14 and 28 post transplantation most of the host-derived cells have died and the peripheral blood donor and bone marrow competitive transplant cells are dominant. There are significant increases in GFP+ donor cell chimerism in mice that received cells from mice mobilized with AMD3100+ VPC01091. 29A—Blood cell fraction. 29B—BM cell fraction. Host cells, PB donor cells and BM donor cells were tested. Abscissa—AMD cells, A+V cells, AMD Sca1+, A+V Sca1+, AMD CD45+, A+V CD45+, AMD CD11b+, and A+V CD11b+.

DETAILED DESCRIPTION

Abbreviations and Acronyms

Figure 1:
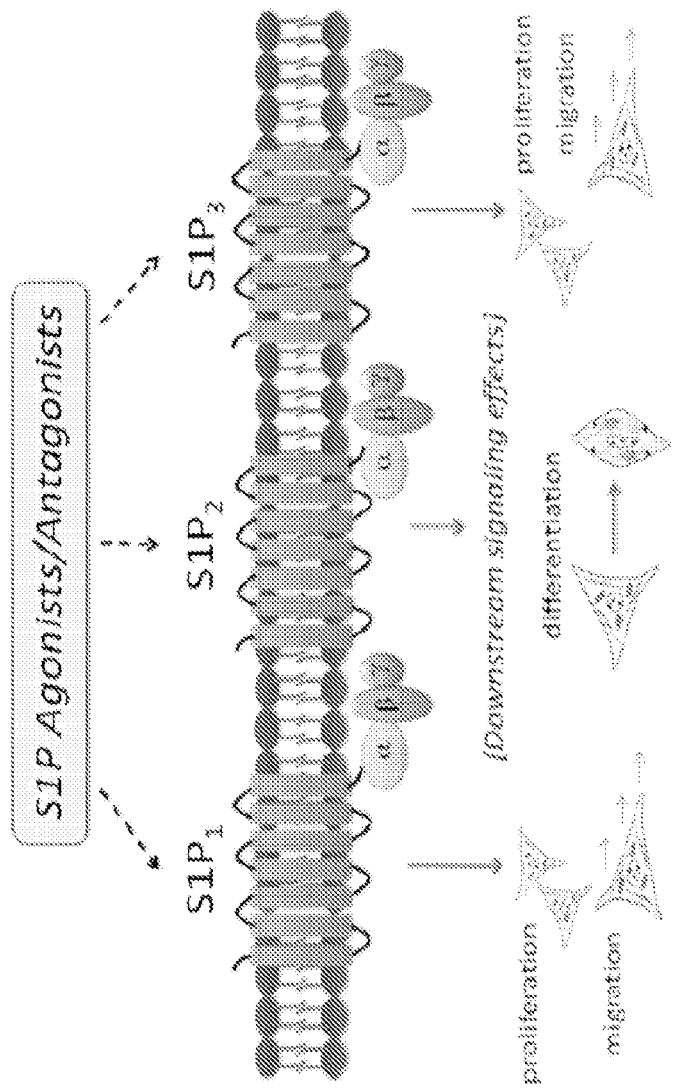
FIG. 1: Schematic illustrating selective activation of S1P receptors 1, 2, & 3 in vivo sand some of their downstream effects. S1P signaling is mediated by a family of G protein coupled receptors, S1P1-S1P5. Endothelial Cells (ECs), vascular Smooth Muscle Cells (vSMCs) and BMCs express S1P receptors 1, 3, and 2, in order of decreasing abundance.
Figure 2:
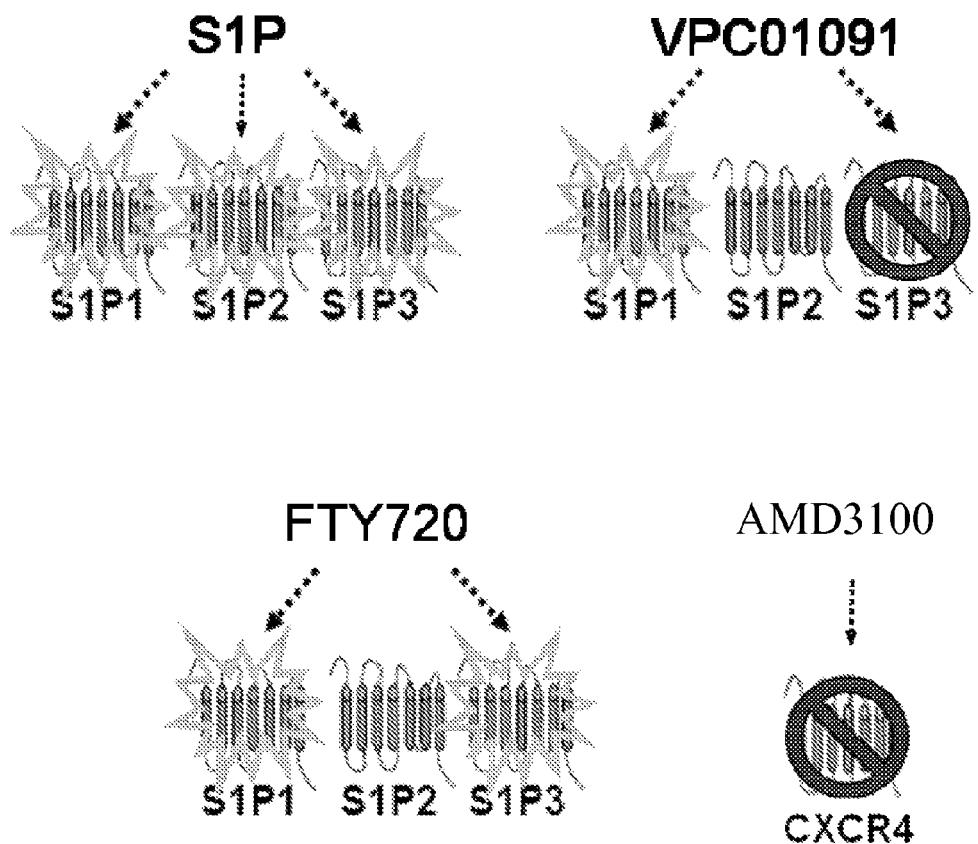
FIG. 2: Schematic illustrating selective S1P receptor agonists and antagonists permit interrogation of physiological roles of S1P receptors. Various S1P receptor-targeted compounds and AMD3100 and their receptor-specific activity. Green starburst=agonist activity; red 'no' symbol=antagonist activity.

AM—anti-inflammatory monocytes
AMD3100—also referred to as Plerixafor and Mozobil
ASCT—autologous stem cell transplantation
BM—bone marrow
BMP-2—bone morphogenetic protein 2
BMC—bone marrow-derived cell
BMSC—bone marrow stem cells
BSA—bovine serum albumin
C—coated
CFU—colony forming unit
C/L—coated-loaded DMEM—Dulbecco's modified Eagle's medium
EC—endothelial cell
ECM—extracellular matrix
EPC—endothelial progenitor cell
EPC-EC—endothelial progenitor derived endothelial cell
ES—embryonic stem cell
FACS—fluorescent activated cell sorting
FAF—fatty acid free
FBS—fetal bovine serum
FG—fibrinogen
FGF—fibroblast growth factor
FN—fibronectin
FTY720—fingolimod
gf—growth factor (also referred to as "GF")
GPCR—G-protein coupled receptor
GVHD—graft vs. host disease
H&E—hematoxylin and eosin
HL—Hodgkins Lymphoma
HSC—hematopoietic stem cell
HS—human serum (also referred to as HmS herein)
HSA—human serum albumin
IL-1β—interleukin-1 beta
IGF-1—insulin-like growth factor 1
IM—inflammatory monocytes
MMP—matrix metalloprotease
MSC—mesenchymal stem cell
PBMC—peripheral blood mononuclear cell
PDGF—platelet-derived growth factor
PHBV—polyhydroxybutyrate-co-valerate
PLA—polylactide
PLAGA—poly(lactic-co-glycolic acid)
S1P—sphingosine-1-phosphate
SBF—simulated body fluid
SCGF-β—stem cell growth factor-β
SDF-1—stromal derived factor 1
SMA—smooth muscle α-actin
SMC—smooth muscle cell
TBI—total body irradiation
TNFα—tumor necrosis factor alpha
U—unloaded
UCB—umbilical cord blood
UCS—ultimate competitive strength
ULA—ultra low attachment tissue culture plate
VEGF—Vascular endothelial growth factor
vSMC—vascular smooth muscle cell
WT—wild type Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element. The term "abluminal" refers to something being directed away from the lumen of a tubular structure, i.e., a blood vessel.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease or disorder, including, but not limited to, pain and inflammation.

The term "adult" as used herein, is meant to refer to any non-embryonic or non-juvenile subject. For example the term "adult adipose tissue stem cell," refers to an adipose stem cell, other than that obtained from an embryo or juvenile subject.

As used herein, an "agonist" is a composition of matter which, when administered to a mammal such as a human, enhances or extends a biological activity attributable to the level or presence of a target compound or molecule of interest in the subject.

A disease or disorder is "alleviated" if the severity of a symptom of the disease, condition, or disorder, or the frequency with which such a symptom is experienced by a subject, or both, are reduced.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

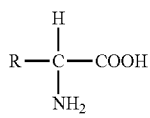

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

"Angiogenesis-associated" disease or disorder refers to a disease or disorder associated with aberrant angiogenesis or a disease or disorder reliant on angiogenesis. Changes in microvessel density are encompassed within the term "angiogenesis-associated."

An "antagonist" is a composition of matter which when administered to a mammal such as a human, inhibits a biological activity attributable to the level or presence of a compound or molecule of interest in the subject.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "autologous", as used herein, refers to something that occurs naturally and normally in a certain type of tissue or in a specific structure of the body. In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbccco's Modified Eagle's Medium, Ham's F12, Eagle's Medium, RPMI, AR8, etc., to which other ingredients may be added. The term docs not exclude media which have been prepared or are intended for specific uses, but which upon modification can be used for other cell types, etc.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system.

The term "biological sample," as used herein, refers to samples obtained from a living organism, including skin, hair, tissue, blood, plasma, cells, sweat, and urine.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year.

As used herein "burn" or "burns" refer to any detectable injury to tissue caused by energy applied to the tissue. The terms "burn" or "burns" further refer to any burning, or charring of the tissue, including thermal burns caused by contact with flames, hot liquids, hot surfaces, and other sources of high heat as well as steam, chemical burns, radiation, and electrical burns. First degree burns show redness; second-degree burns show vesication; third degree burns show necrosis through the entire skin. Burns of the first and second degree are partial-thickness burns, those of the third degree are full-thickness burns.

The phrases "cell culture medium," "culture medium" (plural "media" in each case) and "medium formulation" refer to a nutritive solution for cultivating cells and may be used interchangeably.

The term "clearance", as used herein refers to the physiological process of removing a compound or molecule, such as by diffusion, exfoliation, removal via the bloodstream, and excretion in urine, or via sweat or other fluid.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

A "compound," as used herein, refers to any type of substance or agent that is commonly considered a drug, or a candidate for use as a drug, combinations, and mixtures of the above, as well as polypeptides and antibodies of the invention.

"Cytokine", as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

By "CXCR4 antagonist" is meant a compound which inhibits CXCR4 activity, either directly or indirectly, such as by inhibiting the interaction of CXCR4 with SDF-1.

The term "decreased blood flow", as used herein, refers to a decrease in blood flow at a site of injury, disease, or disorder, and includes, but is not limited, a decrease in flow rate, an increase in stasis, and an increase in sludging in the vessels.

The term "delivery vehicle" refers to any kind of device or material, which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The terms "direct" and "local" administration are used interchangeably herein.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect.

The terms "enhancing bone repair" or "enhancing bone healing" as used herein refer to methods of speeding up or inducing better bone repair or grafting using compounds and coatings of the invention, relative to the speed or amount of bone repair that occurs without administration of compounds and coatings of the invention. These enhancements are described herein or are known in the art and include, but are not limited to, increased allograft vascularization, increases in bone density, increases in structural integrity of bone allograft-host bone interfaces, and increased deposition of bony tissue at bone allograft-host bone interfaces. Repair or healing can be enhanced directly or indirectly.

The term "feeder cells" as used herein refers to cells of one type that are co-cultured with cells of a second type, to provide an environment in which the cells of the second type can be maintained, and perhaps proliferate. The feeder cells can be from a different species than the cells they are supporting. Feeder cells can be non-lethally irradiated or treated to prevent their proliferation prior to being co-cultured to ensure to that they do not proliferate and mingle with the cells which they are feeding. The terms, "feeder cells", "feeders," and "feeder layers" are used interchangeably herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" molecule is a molecule in a form in which it exhibits a property or activity by which it is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Growth factors useful in the present invention include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity".

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "improved blood flow," as used herein, refers to increased blood flow in a subject being treated according to the methods of the invention compared with the flow in a subject with an otherwise identical injury or condition not being treated according to the methods of the invention. Improved flow is determined by methods such as those described herein and can include less stasis, less sludging, or a combination of both, in the subject being treated compared with the untreated subject.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit", as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block".

"Inhibiting decreased blood flow" as described herein, refers to any method or technique which inhibits the decrease in blood flow or associated changes in blood flow following injury, or where decreased blood flow is associated with a disease or disorder, particularly thermal injury. Methods of measuring blood flow are described herein. Inhibition can be direct or indirect.

The term "inhibitor" as used herein, refers to any compound or agent, the application of which results in the inhibition of a process or function of interest, including, but not limited to, differentiation and activity Inhibition can be inferred if there is a reduction in the activity or function of interest.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, "injury" generally refers to damage, harm, or hurt; usually applied to damage inflicted on the body by an external force.

As used herein, an "instructional material" includes a publication, a recording, a diagram, or any other medium of expression, which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container, which contains the identified compound invention, or be shipped together with a container, which contains the identified compound. Alternatively, the instructional material may be shipped separately from the container with the intention that the instructional material and the compound be used cooperatively by the recipient.

Used interchangeably herein are the terms "isolate" and "select".

The term "isolated", when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays, which distinguish cell types.

An "isolated nucleic acid" refers to a nucleic acid segment or fragment, which has been separated from sequences, which flank it in a naturally occurring state, e.g., a DNA fragment that has been removed from the sequences, which are normally adjacent to the fragment, e.g., the sequences adjacent to the fragment in a genome in which it naturally occurs. The term also applies to nucleic acids, which have been substantially purified, from other components, which naturally accompany the nucleic acid, e.g., RNA or DNA, or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, Antibodies, a Laboratory Manual, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to either a molecule that joins two other molecules covalently or non-covalently, e.g., through ionic or hydrogen bonds or van der Waals interactions.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "musculoskeletal" as used herein encompasses the general broad meaning of the term, i.e., an organ system that gives a subject the ability to physically move, by using the muscles and skeletal system. Apart from locomotion, the skeleton also lends support and protects internal organs. Musculoskeletal diseases include, but are not limited to, diseases of the muscles and their associated ligaments, and other connective tissue and of the bones and cartilage viewed collectively. Musculoskeletal disorders include, for example, problems such as low back pain, joint injuries and repetitive strain injuries of various sorts.

"Osteogenesis" as used herein refers to bone growth, bone remodeling, and repair of bone due to injury or disease.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The term "prevent," as used herein, means to stop something from happening, or taking advance measures against something possible or probable from happening. In the context of medicine, "prevention" generally refers to action taken to decrease the chance of getting a disease or condition.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. A "significant detectable level" is an amount of contaminate that would be visible in the presented data and would need to be addressed/explained during analysis of the forensic evidence.

A "reversibly implantable" device is one which may be inserted (e.g. surgically or by insertion into a natural orifice of the animal) into the body of an animal and thereafter removed without great harm to the health of the animal.

As used herein, an "S1P modulating agent" refers a compound or composition that is capable of inducing a detectable change in S1P receptor activity in vivo or in vitro (e.g., at least 10% increase or decrease in S1P activity as measured by a given assay such as the bioassay described in the Examples). "S1P receptor," as used herein, refers to all of the S1P receptor subtypes (for example, the S1P receptors $S1P_1$, $S1P_2$, $S1P_3$, $S1P_4$, and $S1P_5$), unless the specific subtype is indicated.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, "scaffold" refers to a supporting framework, such as one for bone or tissue growth, either in vivo or in vitro.

As used herein, the term "secondary antibody" refers to an antibody that binds to the constant region of another antibody (the primary antibody).

The term "skin," as used herein, refers to the commonly used definition of skin, e.g., the epidermis and dermis, and the cells, glands, mucosa, and connective tissue which comprise the skin.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

By the term "specifically binds," as used herein, is meant a molecule which recognizes and binds a specific molecule, but does not substantially recognize or bind other molecules in a sample, or it means binding between two or more molecules as in part of a cellular regulatory process, where said molecules do not substantially recognize or bind other molecules in a sample.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of diagnosis or treatment is an animal, including a human. It also includes pets and livestock.

As used herein, a "subject in need thereof" is a patient, animal, mammal, or human, who will benefit from the method of this invention.

A "surface active agent" or "surfactant" is a substance that has the ability to reduce the surface tension of materials and enable penetration into and through materials.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "thermal injury" is used interchangeably with "thermal burn" herein.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "tissue injury-associated decreased blood flow", as used herein, refers to the decrease in blood flow which occurs following an injury, such as a wound, a fracture, a surgical procedure, or a thermal injury. The decrease in blood flow includes, but is not limited to, decreased volume, rate, stasis, or sludging. One of ordinary skill in the art will appreciate that there are multiple parameters which can be used as measures or signs of decreased blood flow, as well as multiple techniques to determine decreased blood flow.

The term "topical application," as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous."

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

As used herein "wound" or "wounds" may refer to any detectable break in the tissues of the body, such as injury to skin or to an injury or damage, or to a damaged site associated with a disease or disorder. As used herein, the term "wound" relates to a physical tear, break, or rupture to a tissue or cell layer. A wound may occur by any physical insult, including a surgical procedure or as a result of a disease, disorder condition. Although the terms "wound" and "injury" are not always defined exactly the same way, the use of one term herein, such as "injury", is not meant to exclude the meaning of the other term.

CHEMICAL DEFINITIONS

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from two to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term ($C_5$-$C_8$ alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

As used herein, the term "optionally substituted" refers to from zero to four substituents, wherein the substituents are each independently selected. Each of the independently selected substituents may be the same or different than other substituents.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

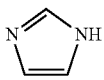

is understood to represent a mixture of the structures:

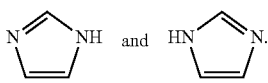

The terminology used herein is for the purpose of describing the particular versions or embodiments only, and is not intended to limit the scope of the present invention. All publications mentioned herein are incorporated by reference in their entirety.

EMBODIMENTS

In one embodiment, the present invention encompasses the use of plerixafor, alone or in combination with other agents. Plerixafor (AMD3100; Mozobil, Genzyme) is a small-molecule CXCR4 chemokine antagonist known to enhance mobilization of stem cells for autologous transplantation in patients with non-Hodgkin's lymphoma (NHL) and multiple myeloma (MM). It is also used in some cases in conjunction with G-CSF administration, but must be administered at least several days later. Plerixafor (AMD3100) is an inhibitor of the interaction between stromal cell-derived factor 1 (SDF-1) and its receptor CXCR4.

Plerixafor (chemical name-1,1'-[1,4-phenylenebis(methylene)]bis-1,4,8,11-tetraazacyclotetradecane octahydrochloride) is a macrocyclic compound and a bicyclam derivative and has the following structure:

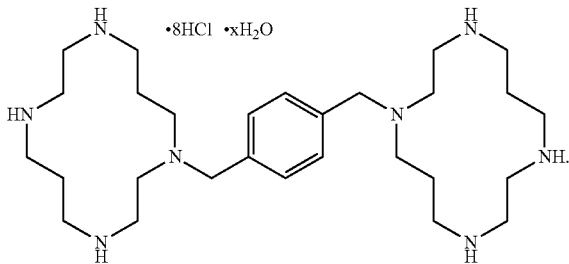 [SMILES: c1cc(CN2CCCNCCNCCCNCC2)ccc1CN1CCCNCCNCCCNCC1 ; "·8HCl"]

It is a strong base; all eight nitrogen atoms accept protons readily. The two macrocyclic rings form chelate complexes with bivalent metal ions, especially zinc, copper and nickel, as well as cobalt and rhodium. The biologically active form of plerixafor is its zinc complex. In the form of its zinc complex, plerixafor acts as an antagonist (or perhaps more accurately a partial agonist) of the alpha chemokine receptor CXCR4 and an allosteric agonist of CXCR7. The CXCR4 alpha-chemokine receptor and one of its ligands, SDF-1, are important in hemopoietic stem cell homing to the bone marrow and in hematopoietic stem cell quiescence. The in vivo effect of plerixafor with regard to ubiquitin, the alternative endogenous ligand of CXCR4, is unknown. Plerixafor has been found to be a strong inducer of mobilization of hematopoietic stem cells from the bone marrow to the bloodstream as peripheral blood stem cells. MacFarland et al., U.S. Pat. No. 6,365,583, described use of AMD3100 to enhance WBCs. AMD3100 was patented (U.S. Pat. No. 5,021,409, Murrer et al.) in 1991.

The compositions and methods can be used to regulate cell mobilization, recruitment, and migration to an ischemic tissue and/or a site of vascular tissue injury or other injury or site requiring cell mobilization, recruitment, and migration to enhance healing or engraftment.

Other compounds are useful in the practice of the invention. Some are analogs or derivatives of FTY720. For example, useful compounds can be found in U.S. Pat. Nos. 8,008,286 and 7,754,703. For example, '703 provides a compound having the formula:

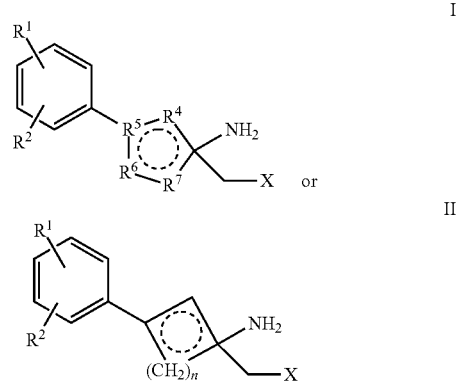

wherein $R^4$ and $R^7$ are independently CH, or $CH_2$; $R^5$ is C, CH, or N, $R^6$ is CH, $CH_2$, O, S or $NR^3$; wherein $R^3$ is hydrogen, or an ($C_1$-$C_{10}$) alkyl group;

X is selected from hydroxyl, phosphate, phosphonate, alpha-substituted phosphonate;

$R^1$ is selected from the group consisting of hydrogen, halo, trifluoromethyl, ($C_1$-$C_{10}$) alkyl, ($C_1$-$C_{10}$) alkyl substituted with halo, hydroxy-, ($C_1$-$C_{10}$) alkoxy, or cyano; and $R^2$ is selected from the group consisting of ($C_1$-$C_{20}$)alkyl, cycloalkyl substituted alkyl, ($C_2$-$C_{20}$)alkenyl, ($C_2$-$C_{20}$) alkynyl, aryl, alkyl substituted aryl, arylalkyl and aryl substituted arylalkyl; wherein one or more of the carbon atoms in the $R^2$ groups can be independently replaced with non-peroxide oxygen, sulfur or $NR^B$; wherein $R^8$ is hydrogen, or an ($C_1$-$C_{10}$) alkyl group;

wherein the alkyl, alkenyl, and alkynyl groups in $R^2$ are optionally substituted with oxo; n is 0, 1, 2 or 3; and ⌬ represents 1, 2, or 3, optional double bonds; or a pharmaceutically acceptable salt or ester thereof.

A specific compound of the invention of formula (II) is VPC01091, where X is OH, $R^1$ is hydrogen, $R^2$ is octane ($C_8H_{17}$), n is 2, and the $R^2$ group is in the para position on the phenyl ring. The formula is:

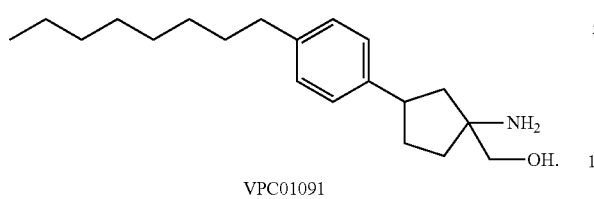
VPC01091

A specific compound of the invention of formula (II) is VPC02162, where X is OH, $R^1$ is hydrogen, $R^2$ is octane ($C_8H_{17}$), n is 2, and the $R^2$ group is in the meta position on the phenyl ring. The formula is:

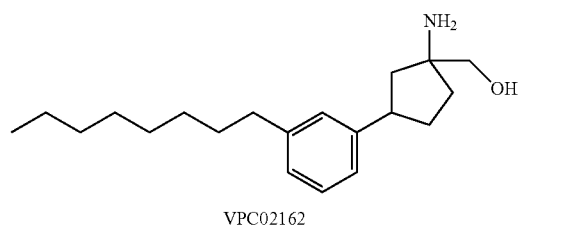 [SMILES: CCCCCCCCc1cccc(C2CCC(N)(CO)C2)c1]
VPC02162

The invention of '703 also includes the following isomers:

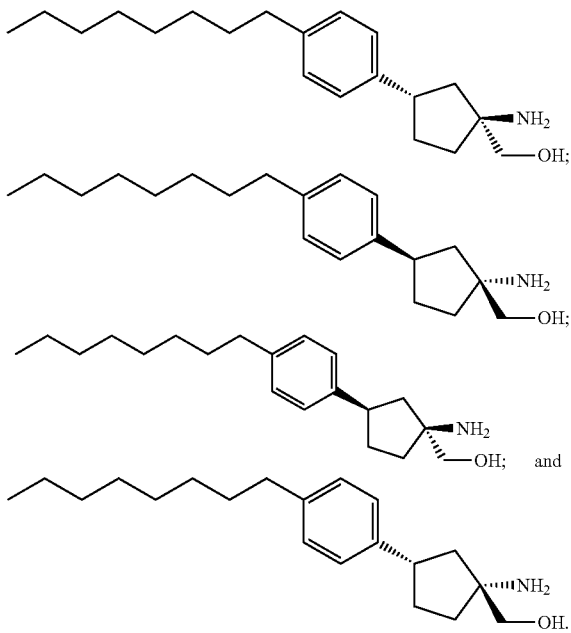

These compounds can be prepared as a mixture and separated by chromatography. Suitable conditions for separation are as follows: Column: Chiralpak AD 4.6 mm ID×250 mm; Mobile Phase: Hex/EtOH/MeOH/DEA=95/2.5/2.5/0.03; Flow Rate: 1 mL/min; Detector: UV 220 nm; Column Temp: 40° C.; or Column Temp: 25° C. After separation, it was found that two isomers were not phosphorylated by the SPHK2 enzyme in vitro. However, when phosphorylated prior to testing the phosphorylated compounds were found to be active agonists of the S1P receptors.

'703 further provides VPC01211:

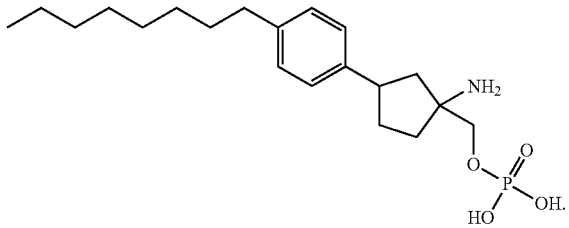 [SMILES: CCCCCCCCc1ccc(C2CCC(N)(COP(=O)(O)O)C2)cc1]

'703 further provides VPC02164:

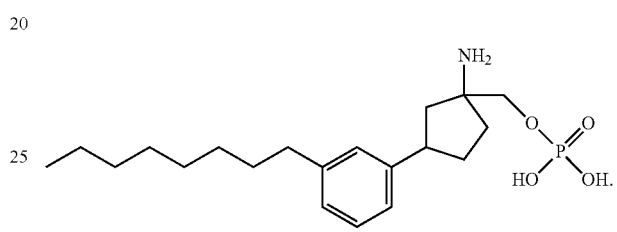

Additional examples of compounds of the invention that include heteroatoms (e.g., N, S, O) and/or double bonds in the cycloalkyl ring include the structures below:

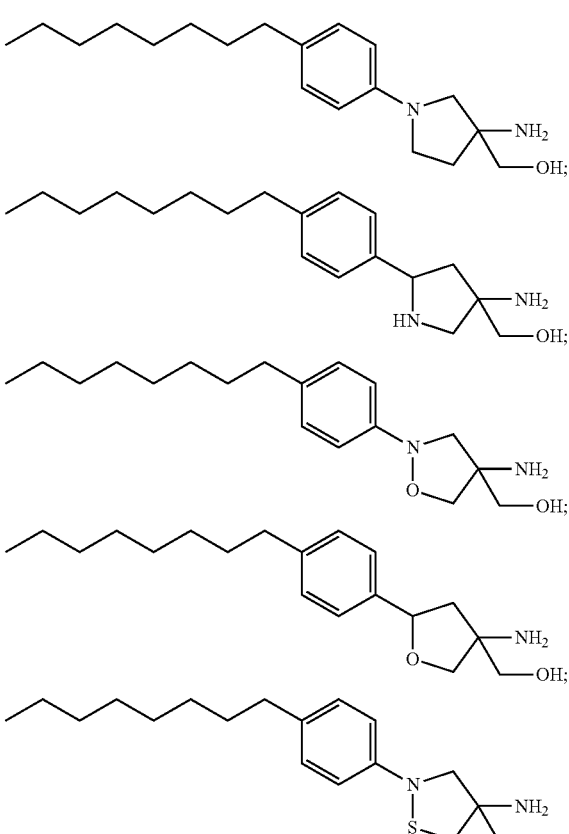

-continued

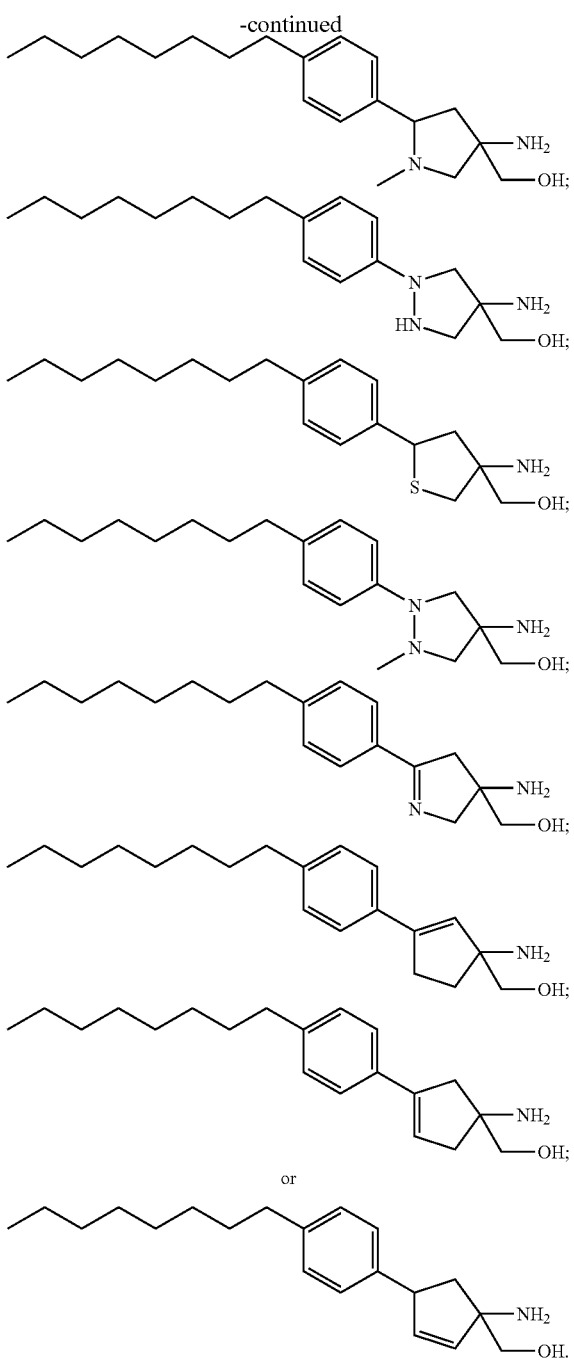

'703 further provided esters of the compounds of formula (I) or formula (II), where the formation of the ester can convert the compounds to pro-drugs to enhance administration, e.g., increase oral availability. In addition, the invention also provides pharmaceutically acceptable salts of the compounds of formula (I) or formula (II). Further, the invention provide all possible isomers of the structures described by formula (I) or formula (II), noting that when n is one (cyclobutane) the compound is symmetric and lacks chiral centers, but cis and trans forms exist.

In some embodiments, compounds of the invention are applied locally. In one aspect, they are administered or delivered in a polymer. The present invention provides for the use of bioactive polymer compositions for the compositions and methods of the invention, including, but not limited to, the polymers PLAGA and PHBV and bioactive molecules including, but not limited to, FTY720 and S1P, and biologically active analogs and derivatives thereof. These polymers are biocompatible and biodegradable.

The present application discloses the ability of FTY720, locally released from thin biomaterial surfaces, to improve allograft vascularization, mechanical integrity, osseous remodeling, and ultimately incorporation at the host-graft interface. Specifically, devitalized bone allografts were coated with a thin polymer coating of FDA-approved 50:50 poly (lactic-co-glycolic acid) (PLAGA) encapsulated with bioactive FTY720.

The present invention provides compositions and methods useful for enhancing bone and wound healing, comprising administering a composition containing a biocompatible polymer and at least one compound having S1P receptor selective activity, or biologically active derivatives and analogs thereof. In one aspect, the activity is agonist activity. In another aspect, the activity is antagonist activity.

In one embodiment, the invention encompasses administering an effective amount of to a wound or defect in a subject in need thereof.

In one aspect, the method stimulates healing of a bone allograft.

In one aspect, the polymer of the invention is PLAGA or PHBV.

In one aspect, the composition comprising a polymer and at least one S1P receptor selective agonist or antagonist is coated on a bone allograft and the bone allograft is inserted into the bony defect. In one aspect, the agonist is FTY720, or a derivative or analog thereof.

In one aspect, PLAGA is a 50:50 or 85:15 mixture of the 72.3 kDa and 123.6 kDa forms.

In one aspect, PLAGA is mixed with methylene chloride to form a PLAGA:methylene chloride solution. In one aspect, PLAGA is mixed with methylene chloride at weight to volume ratios of 1:10, 1:12, or 1:14. In one aspect, FTY720 or a biologically active derivative or analog thereof is added to the PLAGA:methylene chloride solution. In one aspect, FTY720 or a biologically active derivative or analog thereof is added to said PLAGA:methylene chloride solution at a ratio of about 1:200 weight:weight.

The present invention can also be practiced with other effective polymers, and one of ordinary skill in the art will appreciate how to choose and use those suitable effective polymers.

The polymer composition comprising at least one bioactive agent, including, but not limited to the bioactive agent FTY720 and active derivatives and analogs thereof, can be applied to materials other than bone graft material as exemplified herein. The structure of S1P is provided below.

Sphingosine 1-phosphate (S1P)

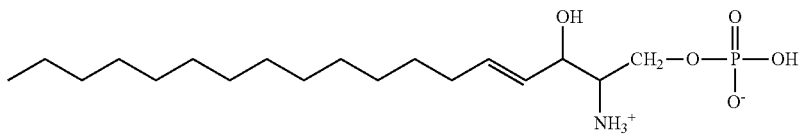 [SMILES: CCCCCCCCCCCCC/C=C/C(O)C([NH3+])COP(=O)([O-])O]

In one aspect, FTY720, or biologically active derivatives and analogs thereof are phosphorylated. In one aspect, other S1P receptor agonists which stimulate the same activity as FTY720 are used. In one aspect, the compound is in the form of a salt or an ester.

Support for other known compounds that are biologically active analogs and derivatives of S1P and FTY720 and their synthesis is available in the art and can be found, for example, in U.S. Pat. Nos. 7,241,790, 7,560,477, and 7,638,637, in U.S. patent application Ser. Nos. 12/179,816, 12/470,011, 12/470,017, 12/189,010, and 12/470,009, and in PCT Pat. App. WO US/2009/023854.

Injuries, Wounds, Diseases, and Disorders

A subject having a site of injury or wound, or in some cases a disease or disorder, may be susceptible to decreased blood flow at that site and therefore be in need of treatment. In one aspect, the decreased blood flow is in microvessels. These conditions may typically arise from many types of injury including trauma, surgery, and trauma to the skin and/or exposed soft tissue, resulting in an inflammatory reaction and decreased blood flow, particularly in the microvasculature. The types of injuries, disease, and disorders encompassed by the methods of the invention therefore include, bone trauma, diseases, and disorders, burns, chronic wounds, and surgical procedures such as microvascular surgery, skin flaps and skin grafts, and tissue injury resulting from, for example, a burn, scrape, cut, incision, laceration, ulcer, body piercing, bite wound, trauma, stab wound, gunshot wound, surgical wound, stretch injury, crush wound, compression wound, fracture, sprain, strain, stroke, infarction, aneurysm, herniation, ischemia, fistula, dislocation, radiation, cell, tissue or organ grafting and transplantation, injuries sustained during medical procedures, or cancer.

Such injuries include, but are not limited to, bone injury, skin injury, muscle injury, brain injury, eye injury, or spinal cord injury. Tissue injury can include joint injury, back injury, heart injury, vascular system injury, soft tissue injury, cartilage injury, lymphatic system injury, tendon injury, ligament injury, or abdominal injury.

While it is important to treat any condition in which the potential for cell or tissue damage exists immediately (e.g., an acute wound), it is essential that certain conditions be treated before they become chronic conditions. Chronic diseases are a challenge to the patient, the health care professional, and to the health care system. They significantly impair the quality of life for millions of people in the United States. Intensive treatment is required with a high cost to society in terms of lost productivity and health care dollars. The management of chronic diseases can place an enormous strain on health care resources. Diseases or conditions, for example, wounds that were once acute but have progressed to chronic often do so because the diseases cannot be controlled or treated with known therapies. Therefore, there is a need for improved therapies for treating chronic diseases and conditions characterized by cell and tissue damage.

Other non-limiting examples of wounds suitable for treatment in accordance with the present disclosure include trauma, fractures, animal bites, arterial disease, insect stings and bites, bone infections, compromised skin/muscle grafts, gangrene, skin tears or lacerations, surgical incisions, including slow or non-healing surgical wounds, and post-operation infections. It is understood, that the listed wounds are non-limiting and that only a portion of wounds suitable for treatment in accordance with the present disclosure are listed herein.

Additional Therapeutic Agents and Ingredients

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (0 cytokines; (g) hormones; and (h) combinations thereof.

The types of drugs and specific drugs within categories which are encompassed within the invention are intended to be non-limiting examples.

In one embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart). Antimicrobial agents useful for the invention include those directed against the spectra of gram positive organisms, gram negative organisms, fungi, and viruses.

The present invention provides for the use of anesthetics. According to the topical anesthetic embodiment of the present invention, in one aspect, suitable local anesthetic agents having a melting point of 30° to 70° C. are prilocalne, tetracaine, butanilcaine, trimecaine, benzocaine, lidocaine, bupivocaine, dibucaine, mepivocaine, and etidocaine.

The present invention further encompasses the use of at least two anesthetics.

The local anesthetic composition of the present invention may further comprise suitable additives, such a pigment, a dye, an anti-oxidant, a stabilizer or a fragrance provided that addition of such an additive does not destroy the single phase of the anesthetic composition.

In one aspect, the hydrated local anesthetic mixture is prepared by melting the local anesthetic with the higher melting point of the two, followed by addition of the other local anesthetic, under vigorous mechanical mixing, such as trituration or grinding. A milky viscous liquid is formed, at which point, the surfactant is added with more mechanical mixing. Mixing of the surfactant produces a milky liquid of somewhat lower viscosity. Finally, the balance of water is added under vigorous mechanical mixing. The material can then be transferred to an air tight container, after which a clear composition is obtained after about 60 minutes at room temperature.

Alternatively, the hydrated local anesthetic mixture can be prepared by first melting the lower melting local anesthetic, followed by addition of the other local anesthetic along with vigorous mechanical mixing, then addition of the surfactant and water as above. However, when the lower melting local anesthetic is melted first, the storage time needed to obtain the single-phase composition, increases from about 1 hour to about 72 hours. Accordingly, the former method is preferred.

One of ordinary skill in the art will appreciate that there are multiple suitable surfactants useful for preparing the hydrated topical anesthetic of the present invention. For example, single-phase hydrated topical anesthetics can be prepared from anionic, cationic, or non-ionic surfactants.

Several embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Antimicrobial agents include, but are not limited to:

silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine.

Analgesic:

Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antihypertensive:

Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Eeadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Tierynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Anti-inflammatory: Alclofenac; Alclometasone Dipropionate; Algestone Acetonide; Alpha Amylase; Ameinafal; Ameinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Growth Factors

In one embodiment, an effective amount of at least one growth factor, cytokine, hormone, or extracellular matrix compound or protein useful for enhancing wound healing is administered as part of the composition. In another aspect, one or more growth factors are administered separately from the polymer:S1P receptor agonist composition. In one aspect, a combination of these agents is used. In one aspect, growth factors useful in the practice of the invention include, but are not limited to, EGF, PDGF, GCSF, IL6, IL8, IL10, MCP1, MCP2, Tissue Factor, FGFb, KGF, VEGF, PDGF, MMP1, MMP9, TIMP1, TIMP2, TGFβ, interferons, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into, or included as an additive within, a composition comprising compounds of the present invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18. Embodiments involving amino acids, peptides, polypeptides, and proteins may include any type of such molecules of any size and complexity as well as combinations of such molecules.

Pharmaceutical Compositions and Delivery Form

The formulations of the invention may be prepared in a variety of forms known in the art, such as liquids, aerosols, or gels, if not used in a polymer composition, or the active ingredient can be added to the polymer solution. Topical administration of the present formulation can be performed by, for example, hand, mechanically (e.g., extrusion and spray delivery) or as a component of a dressing (e.g., gauze or other wound covering). The administration of the formulation directly by hand or as described herein to a tissue or surface, such as an allograft, is preformed to achieve a therapeutic coating, which may be uniform, alone or in combination with an overlying dressing.

Delivery of the bioactive ingredients is not limited to the polymers described herein, but also includes, but is not limited to, hydrogels, PEG, polysaccharides, alginate, chitosan, and lipid coatings.

In one embodiment, the administration of the formulation mechanically is performed by using a device that physically pushes the composition onto a tissue or biomaterial surface to achieve a therapeutic coating, which may be uniform, alone or in combination with an overlying dressing. In one aspect, the material, such as an allograft, is bathed in the solution.

In another embodiment, the formulation can be sprayed onto a tissue or biomaterial surface to achieve a therapeutic coating, which may be uniform, alone or in combination with an overlying dressing. When part of a dressing, the formulation is applied to achieve a therapeutic coating of the surface, which may be uniform.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 70% (w/w) active ingredient, although the concentration of the active ingredient may be as high as the solubility limit of the active ingredient in the solvent. Formulations for topical administration may further comprise one or more of the additional ingredients described herein.

Those of ordinary skill in the art will be able to identify readily those pharmaceutical agents that have utility with the present invention. Those of ordinary skill in the art will also recognize numerous other compounds that fall within the categories and that are useful according to the invention for treating injuries where reduced blood flow occurs.

The invention encompasses the preparation and use of compositions useful for treatment of various skin related injuries, trauma, diseases, disorders, or conditions described herein, including burns, wounds, surgical incisions, etc. The invention also encompasses other injuries, trauma, associated diseases, and disorders other than those of the skin, including, but not limited to, gum diseases and disorders. Such a composition may consist of the polymer and the active ingredient alone, in a form suitable for administration to a subject or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art.

An obstacle for topical administration of pharmaceuticals to the skin is the stratum corneum layer of the epidermis. The stratum corneum is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance, which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The compounds of the invention may be administered to, for example, a cell, a tissue, or a subject by any of several methods described herein and by others which are known to those of skill in the art.

The relative amounts of the active ingredient, the pharmaceutically acceptable carrier, and any additional ingredients in a pharmaceutical composition of the invention will vary, depending upon the identity, sex, age, size, and condition of the subject treated and further depending upon the route by which the composition is to be administered.

In addition to the active ingredient, a composition of the invention may further comprise one or more additional pharmaceutically active or therapeutic agents. Particularly contemplated additional agents include anti-emetics and scavengers such as cyanide and cyanate scavengers.

Controlled- or sustained-release formulations of a composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Additionally, formulations for topical administration may include liquids, ointments, lotions, creams, gels (e.g., poloxamer gel), drops, suppositories, sprays, aerosols, and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical composition may be optionally combined with other ingredients such as moisturizers, cosmetic adjuvants, antioxidants, chelating agents, bleaching agents, tyrosinase inhibitors, and other known depigmentation agents, surfactants, foaming agents, conditioners, humectants, wetting agents, emulsifying agents, fragrances, viscosifiers, buffering agents, preservatives, sunscreens, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

The present invention encompasses biologically active analogs, homologs, derivatives, and modifications of the compounds of the invention. Methods for the preparation of such compounds are known in the art.

Liquid derivatives and natural extracts made directly from biological sources may be employed in the compositions of this invention in a concentration (w/w) from about 1 to about 99%. Fractions of natural extracts and protease inhibitors may have a different preferred rage, from about 0.01% to about 20% and, more preferably, from about 1% to about 10% of the composition. Of course, mixtures of the active agents of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea, and combinations thereof. A particularly preferred preservative is a combination of about 0.5% to 2.0% benzyl alcohol and 0.05% to 0.5% sorbic acid.

The composition may include an antioxidant and a chelating agent which inhibit the degradation of the compound for use in the invention in the aqueous gel formulation. Preferred antioxidants for some compounds are BHT, BHA, alphatocopherol, and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are preferred antioxidant and chelating agent respectively for some compounds, other suitable and equivalent antioxidants and chelating agents may be substituted therefor as would be known to those skilled in the art.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Other components such as preservatives, antioxidants, surfactants, absorption enhancers, viscosity enhancers or film forming polymers, bulking agents, diluents, coloring agents, flavoring agents, pH modifiers, sweeteners or taste-masking agents may also be incorporated into the composition. Suitable coloring agents include red, black, and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

Absorption enhancers for use in accordance with the present invention include, for example, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin. In certain preferred embodiments wherein an absorption enhancer is included in the formulation, the absorption enhancer is included in an amount of from about 0.001% to about 10% by weight of the formulation, preferably in an amount of about 0.01% to about 5% by weight of the formulation.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Generally, compositions may be administered systemically, for example, orally, parenterally, intravenous, or topically in dosage unit formulations containing conventional nontoxic pharmaceutically acceptable carriers, adjuvants, and vehicles as desired, or may be locally administered by means such as, but not limited to, injection, implantation, grafting, topical application, or parenterally. A means of administering cells may include, but is not limited to, infusion. Systemically may also include, for example, by a pump, by an intravenous line, or by bolus injection. Bolus injection can include subcutaneous, intramuscular, or intraperitoneal routes. The phrases "systemic administration" or "administered systemically" as used herein mean the administration of a compound(s) of the invention, composition, drug or other material, such that it enters the subject's system and, thus, is subject to metabolism and other like processes, for example, subcutaneous administration.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

The pharmaceutical compositions of the invention can be administered in any suitable formulation, by any suitable means, and by any suitable route of administration. Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Topical administration of compositions of the invention may include transdermal application. Transdermal application can be performed either passively or using iontophoresis or electroporation.

Compositions of the invention may be applied using transdermal patches. Transdermal patches are adhesive backed patches laced with an effective amount of compounds of the invention. The pressure-sensitive adhesive of the matrix will normally be a solution of polyacrylate, a silicone, or polyisobutylene (PIB). Such adhesives are well known in the transdermal art. See, for instance, the Handbook of Pressure Sensitive Adhesive Technology, 2nd Edition (1989) Van Nostrand, Reinhold.

Pressure sensitive solution polyacrylate adhesives for transdermal patches are made by copolymerizing one or more acrylate monomers ("acrylate" is intended to include both acrylates and methacrylates), one or more modifying monomers, and one or more functional group-containing monomers in an organic solvent. The acrylate monomers used to make these polymers are normally alkyl acrylates of 4-17 carbon atoms, with 2-ethylhexyl acrylate, butyl acrylate, and isooctyl acrylate being preferred. Modifying monomers are typically included to alter the Tg of the polymer. Such monomers as vinyl acetate, ethyl acrylate and methacrylate, and methyl methacrylate are useful for this purpose. The functional group-containing monomer provides sites for crosslinking. The functional groups of these monomers are preferably carboxyl, hydroxy or combinations thereof. Examples of monomers that provide such groups are acrylic acid, methacrylic acid and hydroxy-containing monomers such as hydroxyethyl acrylate. The polyacrylate adhesives are preferably crosslinked using a crosslinking agent to improve their physical properties, (e.g., creep and shear resistance). The crosslinking density should be low since high degrees of crosslinking may affect the adhesive properties of the copolymer adversely. Examples of crosslinking agents are disclosed in U.S. Pat. No. 5,393,529. Solution polyacrylate pressure sensitive adhesives are commercially available under tradenames such as GELVA™ and DURO-TAK™ from 3M.

Polyisobutylene adhesives are mixtures of high molecular weight (HMW) PIB and low molecular weight (LMW) PIB. Such mixtures are described in the art, e.g., PCT/US91/02516. The molecular weight of the HMW PIB will usually be in the range of about 700,000 to 2,000,000 Da, whereas that of the LMW PIB will typically range between 35,000 to 60,000. The molecular weights referred to herein are weight average molecular weight. The weight ratio of HMW PIB to LMW PIB in the adhesive will normally range between 1:1 to 1:10. The PIB adhesive will also normally include a tackifier such as polybutene oil and high Tg, low molecular weight aliphatic resins such as the ESCOREZ™ resins available from Exxon Chemical. Polyisobutylene polymers are available commercially under the tradename VISTANEX™ from Exxon Chemical.

The silicone adhesives that may be used in forming the matrix are typically high molecular weight polydimethyl siloxanes or polydimethyldiphenyl siloxanes. Formulations of silicone adhesives that are useful in transdermal patches are described in U.S. Pat. Nos. 5,232,702, 4,906,169, and 4,951,622.

The present invention provides a system for the direct application of compounds of the invention, including additional therapeutic agents such as anesthetic agents, by iontophoresis for the treatment of decreased blood flow and concurrent pain associated with injuries, diseases, and disorders. While many compounds may be useful with the invention, as will be discussed below, it is particularly useful for the delivery of anesthetic agents such as lidocaine, bupivicaine, ropivicaine, and mepivicaine to damaged skin.

In one embodiment, the methods of the invention provide a patch device with a donor or delivery chamber that is designed to be applied directly over an injury, incision, or wound site and utilizes an electric field to stimulate delivery of the active compound or additional therapeutic agents(s). The patch is sterilized so that risk of infection is minimal. Additionally, the system delivers medication in a constant manner over an extended period of time. Generally, such time periods are at least 30 minutes and may extend to as many as 96 hours.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute about 50% to about 99.9% (w/w) of the composition, and the active ingredient may constitute about 0.1% to about 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to about 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as about 0.1% (w/w) and as much as about 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, comprise about 0.1% to about 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and may further comprise one or more of the additional ingredients described herein. Additionally, the formulation taken orally can be prepared as a pharmaceutical composition, including, but not limited to, a paste, a gel, a toothpaste, a mouthwash, a solution, an oral rinse, a suspension, an ointment, a cream, and a coating.

A pharmaceutical composition of the invention may be prepared, packaged, or sold in a formulation suitable for ophthalmic administration. Such formulations may, for example, be in the form of eye drops including, for example, a 0.1% to 1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention may be prepared, packaged, or sold in a formulation suitable for intramucosal administration. The present invention provides for intramucosal administration of compounds to allow passage or absorption of the compounds across mucosa. Such type of administration is useful for absorption orally (gingival, sublingual, buccal, etc.), rectally, vaginally, pulmonary, nasally, etc.

In some aspects, sublingual administration has an advantage for active ingredients, as well as additional therapeutic agents, which in some cases, when given orally, are subject to a substantial first pass metabolism and enzymatic degradation through the liver, resulting in rapid metabolization and a loss of therapeutic activity related to the activity of the liver enzymes that convert the molecule into inactive metabolites, or the activity of which is decreased because of this bioconversion.

In some cases, a sublingual route of administration is capable of producing a rapid onset of action due to the considerable permeability and vascularization of the buccal mucosa. Moreover, sublingual administration can also allow the administration of active ingredients which are not normally absorbed at the level of the stomach mucosa or digestive mucosa after oral administration, or alternatively which are partially or completely degraded in acidic medium after ingestion of, for example, a tablet.

The compounds of the invention can be prepared in a formulation or pharmaceutical composition appropriate for administration that allows or enhances absorption across mucosa. Mucosal absorption enhancers include, but are not limited to, a bile salt, fatty acid, surfactant, or alcohol. In specific embodiments, the permeation enhancer can be sodium cholate, sodium dodecyl sulphate, sodium deoxycholate, taurodeoxycholate, sodium glycocholate, dimethylsulfoxide, or ethanol. In a further embodiment, a compound of the invention can be formulated with a mucosal penetration enhancer to facilitate delivery of the compound. The formulation can also be prepared with pH optimized for solubility, drug stability, and absorption through mucosa such as nasal mucosa, oral mucosa, vaginal mucosa, respiratory, and intestinal mucosa.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compounds include polyol compounds, such as oligo-, di- and monosaccharides such as sucrose, mannitol, lactose, L-arabinose, D-erythrose, D-ribose, D-xylose, D-mannose, D-galactose, lactulose, cellobiose, gentibiose, glycerin, and polyethylene glycol. Other examples of hydrophilic low molecular weight compounds useful as carriers within the invention include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

When a controlled-release pharmaceutical preparation of the present invention further contains a hydrophilic base, many options are available for inclusion. Hydrophilic polymers such as a polyethylene glycol and polyvinyl pyrrolidone, sugar alcohols such as D-sorbitol and xylitol, saccharides such as sucrose, maltose, lactulose, D-fructose, dextran, and glucose, surfactants such as polyoxyethylene-hydrogenated castor oil, polyoxyethylene polyoxypropylene glycol, and polyoxyethylene sorbitan higher fatty acid esters, salts such as sodium chloride and magnesium chloride, organic acids such as citric acid and tartaric acid, amino acids such as glycine, beta-alanine, and lysine hydrochloride, and aminosaccharides such as meglumine are given as examples of the hydrophilic base. Polyethylene glycol, sucrose, and polyvinyl pyrrolidone are preferred and polyethylene glycol are further preferred. One or a combination of two or more hydrophilic bases can be used in the present invention.

The present invention contemplates pulmonary, nasal, or oral administration through an inhaler. In one embodiment, delivery from an inhaler can be a metered dose.

An inhaler is a device for patient self-administration of at least one compound of the invention comprising a spray inhaler (e.g., a nasal, oral, or pulmonary spray inhaler) containing an aerosol spray formulation of at least one compound of the invention and a pharmaceutically acceptable dispersant. In one aspect, the device is metered to disperse an amount of the aerosol formulation by forming a spray that contains a dose of at least one compound of the invention effective to treat a disease or disorder encompassed by the invention. The dispersant may be a surfactant, such as, but not limited to, polyoxyethylene fatty acid esters, polyoxyethylene fatty acid alcohols, and polyoxyethylene sorbitan fatty acid esters. Phospholipid-based surfactants also may be used.

In other embodiments, the aerosol formulation is provided as a dry powder aerosol formulation in which a compound of the invention is present as a finely divided powder. The dry powder formulation can further comprise a bulking agent, such as, but not limited to, lactose, sorbitol, sucrose, and mannitol.

In another specific embodiment, the aerosol formulation is a liquid aerosol formulation further comprising a pharmaceutically acceptable diluent, such as, but not limited to, sterile water, saline, buffered saline and dextrose solution.

In further embodiments, the aerosol formulation further comprises at least one additional compound of the invention in a concentration such that the metered amount of the aerosol formulation dispersed by the device contains a dose of the additional compound in a metered amount that is effective to ameliorate the symptoms of disease or disorder disclosed herein when used in combination with at least a first or second compound of the invention.

Compounds of the invention will be prepared in a formulation or pharmaceutical composition appropriate for nasal administration. In a further embodiment, the compounds of the invention can be formulated with a mucosal penetration enhancer to facilitate delivery of the drug. The formulation can also be prepared with pH optimized for solubility, drug stability, absorption through nasal mucosa, and other considerations.

Capsules, blisters, and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

For administration by inhalation, the compounds for use according to the methods of the invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the drugs and a suitable powder base such as lactose or starch.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference. Typically, dosages of the compounds of the invention which may be administered to an animal, preferably a human, range in amount from about 1.0 µg to about 100 g per kilogram of body weight of the animal. The precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compounds may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The composites of the bioactive coating or it constituents of the present invention can be used as a vehicle for the in situ delivery of biologically active agents. The biologically active agents incorporated into, or included as an additive within, the composite of the subject invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composite or cell suspension into a subject to promote subsequent integration and healing processes. The active agents include, but are not limited to, antifungal agents, antibacterial agents, anti-viral agents, anti-parasitic agents, growth factors, angiogenic factors, anesthetics, mucopolysaccharides, metals, cells, and other wound healing agents. Because the processing conditions can be relatively benign (physiological temperature and pH), live cells can be incorporated into the composite during its formation, or subsequently allowed to infiltrate the composite through tissue engineering techniques.

Compositions comprising the compounds and bioactive coatings of the invention can be employed in any suitable manner to facilitate the growth and differentiation of the desired tissue. In other embodiments, the structure is implanted within the host animal directly at the site in which it is desired to grow the tissue or structure. In still another embodiment, the composition can be engrafted onto a host, where it will grow and mature until ready for use. Thereafter, the mature structure (or anlage) is excised from the host and implanted into the host, as appropriate.

Methods for measuring bone and wound healing are known in the art and include various cellular, molecular, biochemical, and histological techniques.

In accordance with one embodiment of the invention, compositions comprising cells and compounds of the invention are used to enhance bone and wound healing, and/or treat patients having deficient bone and wound healing.

Existing bone and wound healing formulations can also be used as pharmaceutically acceptable carriers for the procedures described herein.

The compositions and bioactive coatings and ingredients of the present invention may be administered to a subject alone or in admixture with a composition useful in the repair of bones and wounds and other defects. Such compositions include, but are not limited to bone morphogenetic proteins, hydroxyapatite/tricalcium phosphate particles (HA/TCP), gelatin, poly-L-lysine, and collagen.

Injuries, wounds and defects to which the present inventive method is useful in promoting healing, but are not limited to, broken or defective bones, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, diabetic lesions, or tangential wounds. The method need not achieve complete healing of the wound or defect; it is sufficient for the method to promote any degree of wound healing or correction of the defect. In this respect, the method can be employed alone or as an adjunct to other methods for healing wounded tissue.

In one embodiment, the compositions, bioactive agents and coatings and methods of the invention are useful for disease therapy, tissue repair, transplantation, and treatment of organ, tissue, or cellular debilitation.

The compositions of the present invention can be used as a vehicle for the in situ delivery of biologically active agents. The biologically active agents incorporated into, or included as an additive within, the composite of the subject invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composite or cell suspension into a subject to promote subsequent integration and healing processes. The active agents include, but are not limited to, antifungal agents, antibacterial agents, anti-viral agents, anti-parasitic agents, growth factors, angiogenic factors, anesthetics, mucopolysaccharides, metals, cells, and other wound healing agents. Because the processing conditions can be relatively benign (physiological temperature and pH), live cells can be incorporated into the composite during its formation, or subsequently allowed to infiltrate the composite through tissue engineering techniques.

Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present invention. Other implantable media and devices can be used for delivery of the compounds and bioactive coatings of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The compounds of the present invention can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

In one embodiment, a composition of the invention is administered locally by injection. Compositions may further comprise cells. Compositions can be further combined with known drugs, and in one embodiment, the drugs are bound to the bioactive coating material. These compositions can also be prepared in the form of an implantable device that can be molded to a desired shape. In one embodiment, a graft construct is prepared comprising a biocompatible matrix and one or more cells of the present invention, wherein the matrix is formed in a shape to fill a gap or space created by the removal of a tumor, injured, or diseased tissue.

Compositions comprising bioactive coatings or materials of the invention can be employed in any suitable manner to facilitate the healing, growth, and differentiation of the desired tissue. For example, the composition can be constructed using three-dimensional or stereotactic modeling techniques. To direct the growth and differentiation of the desired structure, the composition can be cultured ex vivo in a bioreactor or incubator, as appropriate. In other embodiments, the structure is implanted within the host animal directly at the site in which it is desired to grow the tissue or structure. In still another embodiment, the composition can be engrafted onto a host, where it will grow and mature until ready for use. Thereafter, the mature structure (or anlage) is excised from the host and implanted into the host, as appropriate.

Matrices suitable for inclusion into the composition can be derived from various sources. As discussed above, the cells, matrices, and compositions of the invention can be used in tissue engineering and regeneration. Thus, the invention pertains to an implantable structure (i.e., an implant) incorporating any of these inventive features. The exact nature of the implant will vary according to the intended use. The implant can be, or comprise, as described, mature or immature tissue. Thus, for example, one type of implant can be a bone implant, comprising a population of the inventive cells that are undergoing (or are primed for) osteoblastic, adipose, chondrogenic, or osteoclastic differentiation, optionally seeded within a matrix material. Such an implant can be applied or engrafted to encourage the generation or regeneration of mature bone or other tissue within the subject.

One of ordinary skill in the art would appreciate that there are other carriers useful for delivering the compositions and compounds of the invention. Such carriers include, but are not limited to, calcium phosphate, hydroxyapatite, and synthetic or natural polymers such as collagen or collagen fragments in soluble or aggregated forms. In one aspect, such carriers serve to deliver the compositions, coatings, as well as organ, tissue, or cells to a location or to several locations. In another aspect, the compositions and compounds can be delivered either through systemic administration or by implantation. Implantation can be into one site or into several sites.

As indicated above, cells can be seeded onto and/or within the organic/inorganic composites of the present invention. Likewise, tissues such as bone or cartilage can be associated with the composites prior to implantation within a patient. Examples of such cells include, but are not limited to, bone cells (such as osteoclasts, osteoblasts, and osteocytes), blood cells, epithelial cells, neural cells (e.g., neurons, astrocytes, and oligodendrocytes), and dental cells (odontoblasts and ameloblasts). Seeded cells can be autogenic, allogenic, or xenogeneic. Seeded cells can be encapsulated or non-encapsulated.

Other agents or compounds that can be incorporated into the composite of the subject invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins and other biologically active compounds that can be incorporated into, or included as an additive within, a composition comprising the bioactive coatings of the invention of the present invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, enzymes, or combinations and biologically active fragments thereof. Other proteins associated with other parts of human or other mammalian anatomy can be incorporated or included as an additive, include proteins associated with cartilage, such as chondrocalcining protein, proteins associated with dentin, such as phosphoryin, glycoproteins and other Gla proteins, or proteins associated with enamel, such as amelogenin and enamelin. Agents incorporated into the composition of the present invention may or may not facilitate or enhance osteoinduction. Adjuvants that diminish an immune response can also be used in conjunction with the composite of the subject invention.

In one embodiment, the biologically active agents or compounds can first be encapsulated into microcapsules, microspheres, microparticles, microfibers, reinforcing fibers and the like to facilitate mixing and achieving controlled, extended, delayed and/or sustained release and combined with the cells of the invention. Encapsulating the biologically active agent can also protect the agent against degradation during formation of the composite of the invention.

In another embodiment of the invention, the biologically active agent is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

The peptides useful in the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride, or an "active ester" group such as hydroxybenzotriazole or pentafluorophenly esters.

Examples of solid phase peptide synthesis methods include the BOC method which utilized tert-butyloxycarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($—NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamic, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function. Conservative amino acid substitutions typically include substitutions within the following groups:
glycine, alanine;
valine, isoleucine, leucine;

aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The invention also includes a kit comprising the composition of the invention and an instructional material which describes administering or using the composition. In another embodiment, this kit comprises a (preferably sterile) solvent suitable for dissolving or suspending the composition of the invention prior to administering the composition. Optionally, at least one growth factor and/or antimicrobial agent may be included in the kit. The present invention should be construed to include kits for improving vascular flow, stimulating angiogenesis, and for bone and wound healing. The invention includes a kit comprising a stimulator of angiogenesis or a compound identified in the invention, a standard, and an instructional material which describes administering the inhibitor or a composition comprising the stimulator. This should be construed to include other embodiments of kits that are known to those skilled in the art, such as a kit comprising a standard and a (preferably sterile) solvent suitable for dissolving or suspending the composition of the invention prior to administering the compound to a cell or an animal. Preferably, the animal is a mammal. More preferably, the mammal is a human.

In accordance with the present invention, as described above or as discussed in the Examples below, there can be employed conventional chemical, cellular, histochemical, biochemical, molecular biology, microbiology, recombinant DNA, and clinical techniques which are known to those of skill in the art. Such techniques are explained fully in the literature. See for example, Sambrook et al., 1989 Molecular Cloning—a Laboratory Manual, Cold Spring Harbor Press; Glover, (1985) DNA Cloning: a Practical Approach; Gait, (1984) Oligonucleotide Synthesis; Harlow et al., 1988 Antibodies—a Laboratory Manual, Cold Spring Harbor Press; Roc et al., 1996 DNA Isolation and Sequencing: Essential Techniques, John Wiley; and Ausubel et al., 1995 Current Protocols in Molecular Biology, Greene Publishing.

The present invention may be embodied in other specific forms without departing from the spirit or essential attributes thereof. This invention encompasses all combinations of the different aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

The presence of adult multipotent "stem" cells has been demonstrated in a large number of tissues, for example the bone marrow, blood, liver, muscle, the nervous system, and in adipose tissue. Adult "stem" cells, which in theory are capable of infinite self-renewal, have great cell plasticity, i.e., the ability to differentiate into tissues other than those for which it was believed they were destined. The properties of said cells, which are similar to those of embryonic stem cells (ES), open up considerable therapeutic perspectives especially as their use does not pose the problems of compatibility and ethics, encountered with ES cells.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

Such cell therapy methods encompass the use of the cells and compositions of this invention in combination with growth factors or chemokines such as those inducting proliferation, lineage-commitment, or genes or proteins of interest. Treatment methods may include providing stem or appropriate precursor cells directly for transplantation where the tissue is regenerated in vivo or recreating the desired tissue in vitro and then providing the tissue to the affected subject, or methods and compositions to recruit cells of interest.

In one aspect, a cell type useful for treatment and/or recruitment, includes, but is not limited to, a cell selected from the group consisting of stem cells, pluripotent stem cells, committed stem cells, embryonic stem cells, adult stem cells, bone marrow stem cells, bone marrow-derived stem cells, adipose stem cells, mesenchymal stem cells, umbilical cord stem cells, dura mater stem cells, precursor cells, differentiated cells, osteoblasts, osteoclasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons.

In one aspect, the cell is a human cell.

Additional techniques and methods useful for the practice of the invention can be found in U.S. patent application Ser. No. 11/313,188, U.S. patent application Ser. No. 11/800,086, U.S. Pat. App. Pub. US 2007/0270844 A1, U.S. patent application Ser. No. 11/339,781, U.S. patent application Ser. No. 11/361,906, and U.S. patent application Ser. No. 11/598,900

The examples provided throughout his application are non-inclusive unless otherwise stated. They include but are not limited to the recited examples.

EXAMPLES

Example 1

Methods

Figure 3:
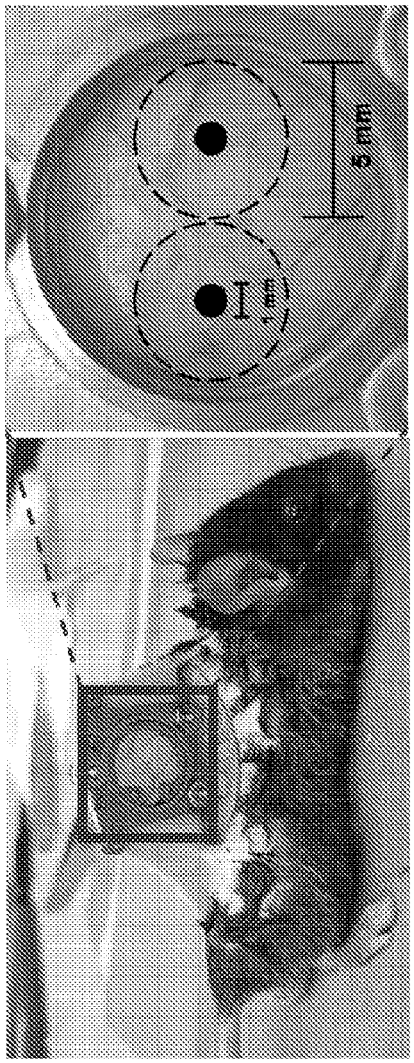
FIG. 3, comprising A and B, demonstrates the murine dorsal skinfold window chamber model.

Murine Dorsal Skinfold Window Chamber 1 mm poly(lactic-co-glycolic acid) PLAGA films loaded with S1P receptor compounds are placed within the window chamber as shown. Repeated measurements of the same vessel networks are recorded and quantified over a 7-day time course using intravital microscopy. (FIG. 3).

BMC Mobilization & Colony Forming Unit Assay

Pharmacological compounds (5 mg/kg) were used to mobilize cells from the bone marrow in wild type and $S1P_3^{-/-}$ mice. Peripheral blood was harvested and plated on Methocult stem cell clonogenic media for CFU assays after 6 days.

Models with CX3CR1-eGFP Mice

Figure 5:
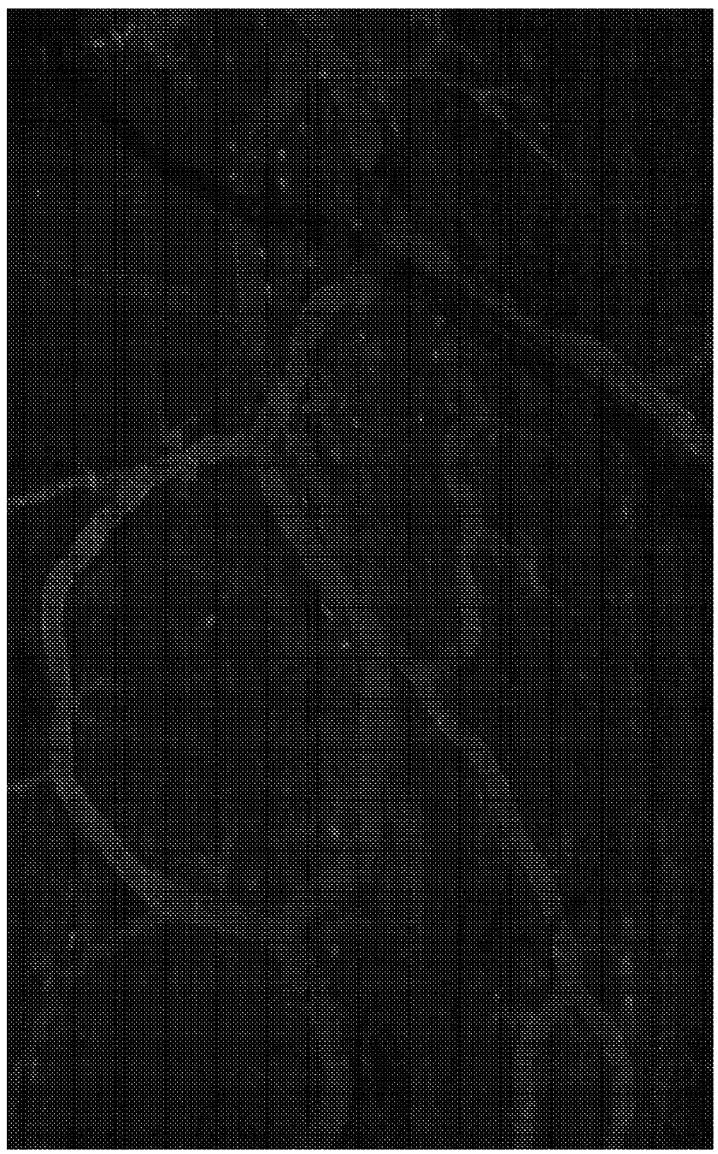
FIG. 5: Confocal microscopic image used to assess CX3CR1 expression in spinotrapezius muscle. Transgenic CX3CR1-eGFP, where 95% of the GFP content is on monocytes and macrophages; the higher CX3CR1 content being on anti-inflammatory monocytes, were used. Green is GFP-labeled CX3CR1 (fractalkine receptor) and red is smooth muscle actin (SMA).

Backpacks were implanted with PLAGA films and collagenase was used to digest dorsal tissue directly around the implants after 3 days to create single cell suspensions. Flow cytometry was used to assess cellular content. A feeder artery to the spinotrapezius muscle was ligated, creating an ischemic environment, and confocal microscopy on whole-mounted tissue was used to assess CX3CR1 expression in the muscle (FIG. 5).

FACS and Migration

Whole bone marrow cells were harvested from C57Bl/6 mice tibiae. They were pre-labeled with antibodies against Lineage 1, Sca1, and c-kit and the LSK subset were sorted, serum starved, and plated at equal concentration after pre-treatment with FTY720. Migration toward media, SDF1, and S1P was calculated.

Bone Marrow Transplant

WT mice were irradiated & reconstituted with mobilized peripheral blood cells from GFP+ mice. After varying amounts of time, blood was collected via the retro-orbital sinus and bone marrow was harvested to assess chimerism over time.

Results

Figure 6A:
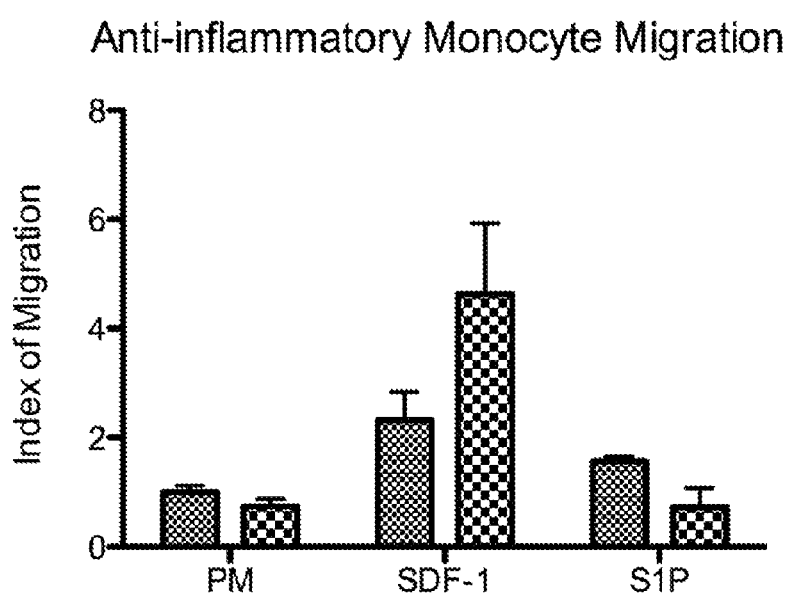
FIGS. 6 (A-D): FTY720 Inhibits Inflammatory Cell Infiltration and Recruits Stem/progenitor Cells Locally A1) FTY720 regulates inflammation and stem cell recruitment locally. $CD45^+/CD11b^-/Ly6C^{low}/CX3CR1^{high}$ anti-inflammatory monocytes (AM) and $CD45^+/CD11b^+/Ly6C^{high}/CX3CR1^{low}$ inflammatory monocytes (IM) (6C) were sorted from mouse marrow. FTY720 pre-treatment increased the migration of AMs towards SDF-1 (6A) but decreased the migration of IMs towards SDF-1 and S1P (6B). In vivo, from tissue treated with PLAGA implants in the murine dorsal skinfold window chamber, the recruitment of IMs to dorsal tissue was attenuated with local FTY720 application (6D). Cells that are $CD45^+/CD11b^+/Ly6C^{high}/CX3CR1^{low}/CD105^+$ and have a decreasing expression of Sca1 (a progenitor cell marker) are consistent with endothelial progenitor derived endothelial cells (EPC-ECs). EPC-ECs were increased with FTY720 treatment, suggesting a FTY720-dependent recruitment and differentiation of EPCs in the dorsal microvasculature.
Figure 6B:
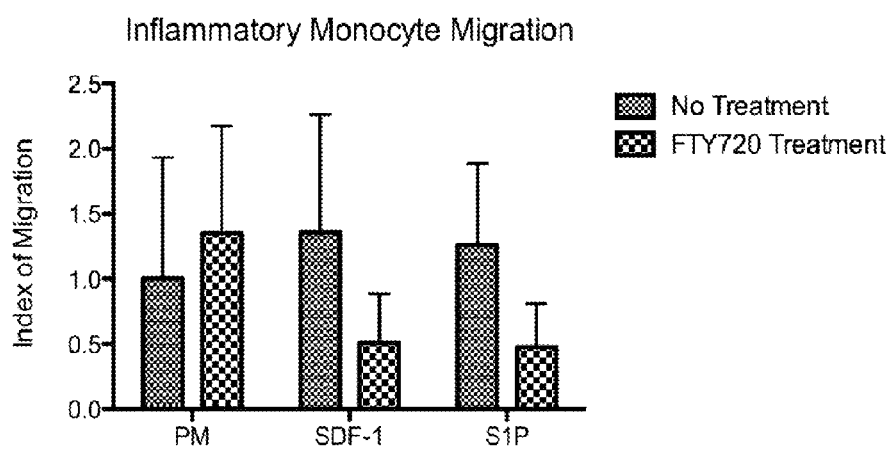
Figure 6B:
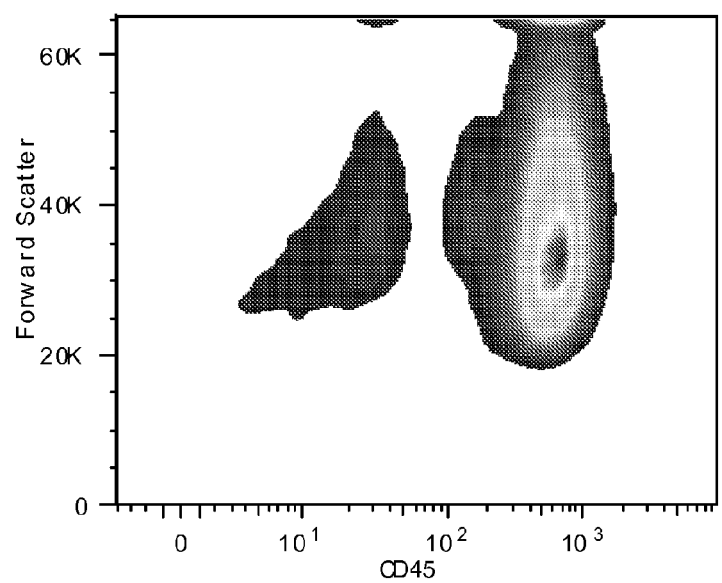

FTY720 Inhibits Inflammatory Cell Infiltration and Recruits Stem/Progenitor Cells Locally $CD45^+/CD11b^+/Ly6C^{low}/CX3CR1^{high}$ anti-inflammatory monocytes (AM) and $CD45^+/CD11b^+/Ly6C^{high}/CX3CR1^{low}$ inflammatory monocytes (IM) (FIG. 6C) were sorted from mouse marrow. FTY720 pre-treatment increased the migration of AMs towards SDF-1 (FIG. 6A) but decreased the migration of IMs towards SDF-1 and S1P (B). In vivo, in tissue from the murine dorsal skinfold window chamber, the recruitment of IMs to dorsal tissue was attenuated with local FTY720 application from PLAGA films (FIG. 6D). Cells that are $CD45^+/CD11b^+/Ly6C^{high}/CX3CR1^{low}/CD105^+$ and have a decreasing expression of Sca1 (a progenitor cell marker) are consistent with endothelial progenitor derived endothelial cells (EPC-ECs). EPC-ECs were increased with FTY720 treatment, suggesting a FTY720-dependent recruitment and differentiation of EPCs in the dorsal microvasculature. Local FTY720 stimulation attenuates the infiltration of inflammatory cells and recruits regenerative stem cells. (See FIGS. 3-6).

FTY720 Recruits CX3CR1+ Cells to Remodeling Vessels

Figure 7A:
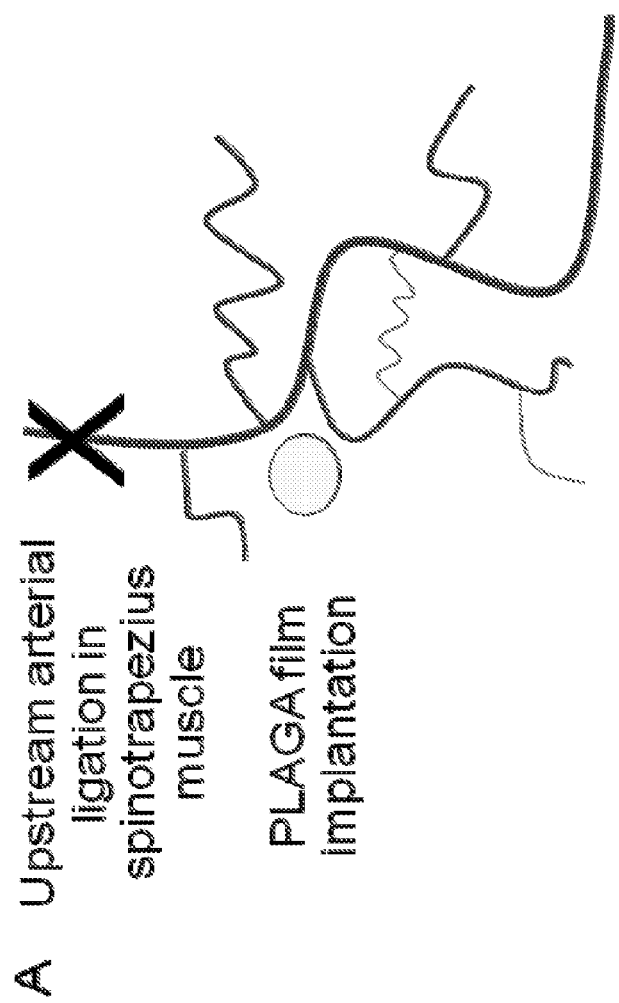
FIG. 7A: Schematic representation of arterial ligation and PLAGA film implantation in spinotrapezius muscle.
Figure 7B:
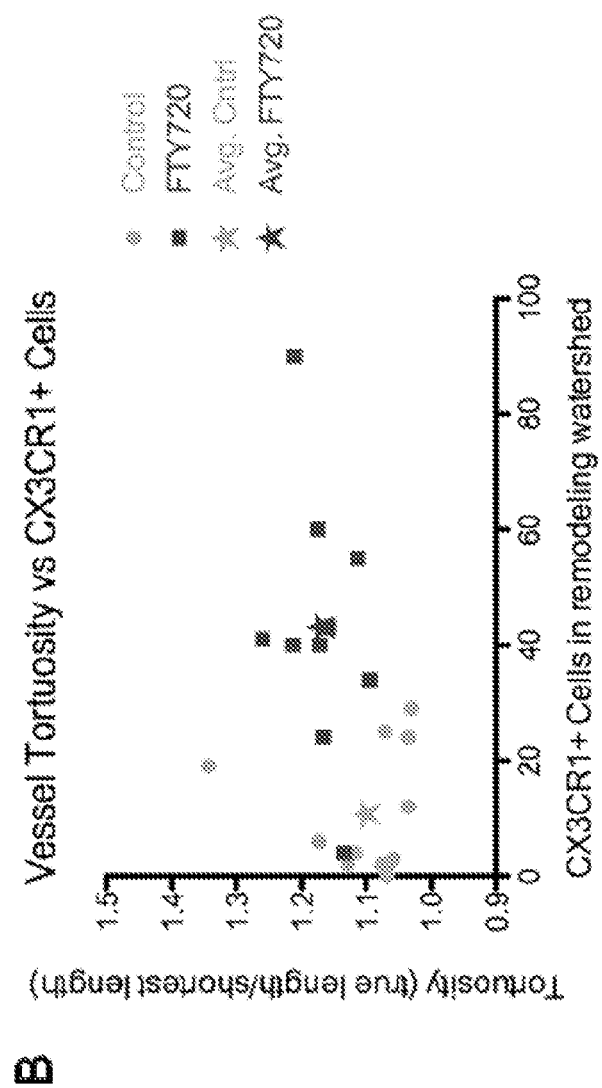
FIG. 7B: Graphically illustrates treatment of cells with FTY720 and vessel tortuosity versus CX3CR1+ cells.
Figure 7C:
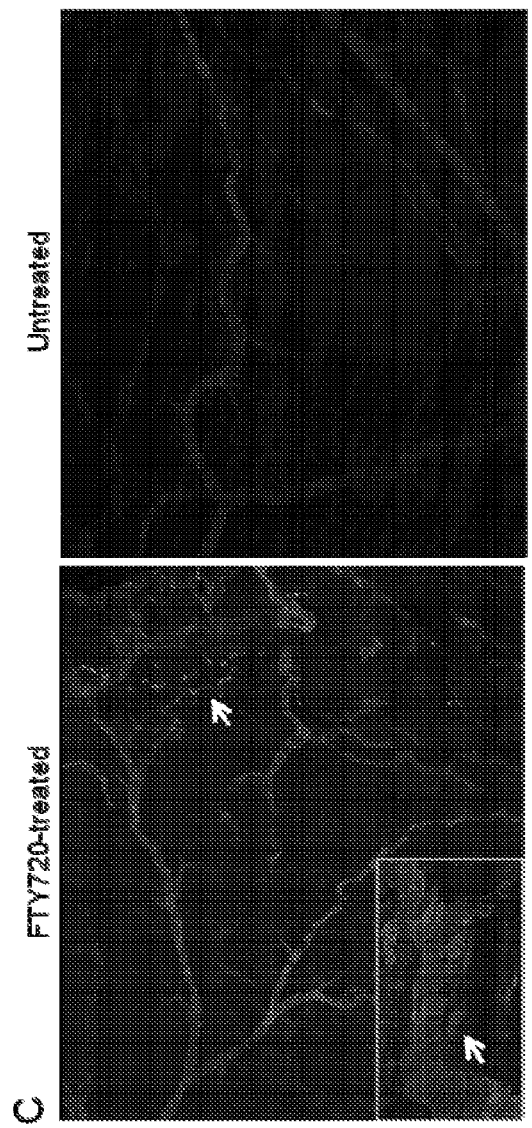
FIG. 7C, comprising right and left panels, demonstrates micrographically that FTY720 recruits CX3CR1+ cells. FTY720-induces remodeling in ischemic muscle (left panel) and promotes tortuosity of vessels as well as recruitment of vessel-associated CX3CR1+ cells (arrows); Right Panel—control.

FTY720-induces remodeling in ischemic muscle and promotes tortuosity of vessels as well as recruitment of vessel-associated CX3CR1+ cells (FIGS. 7A-7C; arrows).

Figure 8A:
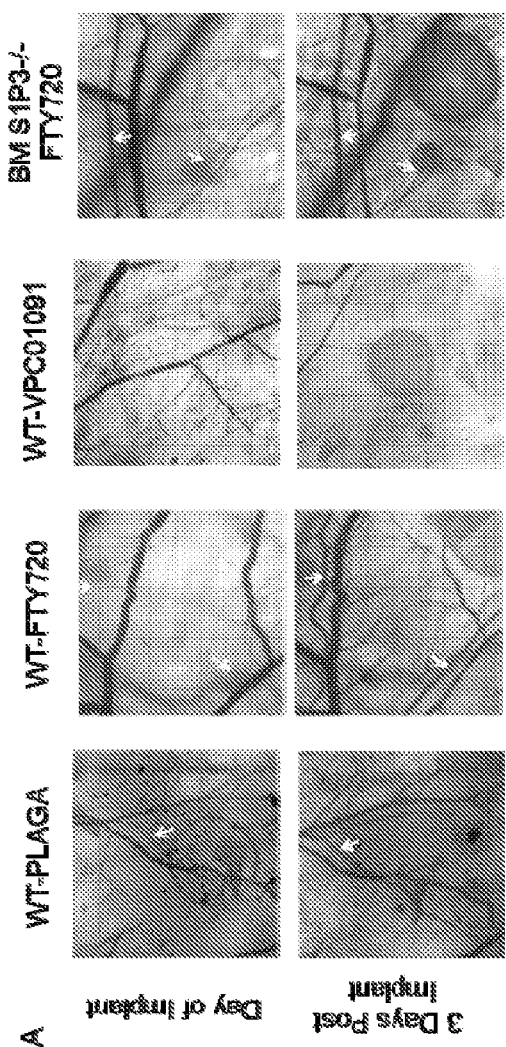
FIG. 8A, demonstrates with intravital microscopic images that marrow derived cells are recruited to sites of microvascular remodeling via $S1P_3$. Intravital images of dorsal microvasculature on day of polymer implantation and 3 days post-implantation. When $S1P_3$ is selectively antagonized on marrow-derived cells there is impaired FTY720-induced microvascular remodeling (A).

$S1P_3$ Expression on Marrow-Derived Cells is Essential for Microvascular Growth and Remodeling "FIG. 8A" demonstrates micrographically the results comparing the day of implant and 3 days post implant for WT-PLAGA, WT-FTY720, WT-VPC01091, and BMS $S1P_3-/-FTY720$. "FIG. 8B" illustrates vascular length density.

Figure 8B:
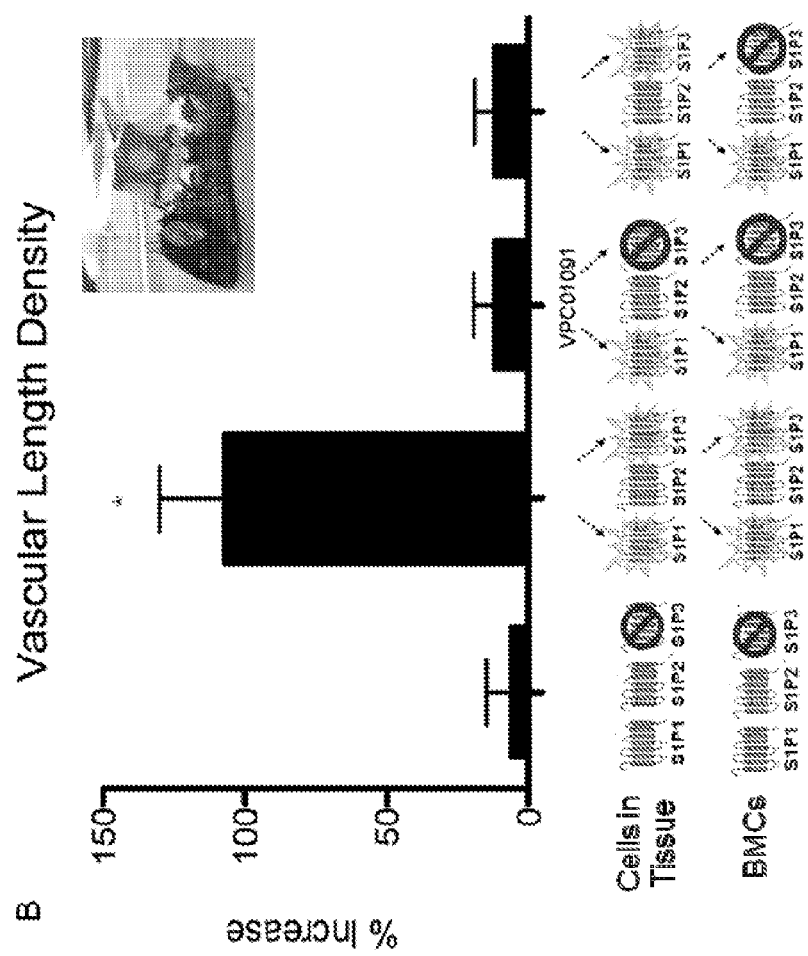
FIG. 8B: BMC $S1P_3$ expression is critical for vascular remodeling as demonstrated graphically (B).

Marrow derived cells were recruited to sites of microvascular remodeling via $S1P_3$ (FIG. 8A). Intravital images of dorsal microvasculature on day of polymer implantation and 3 days post-implantation. When $S1P_3$ is selectively antagonized on marrow-derived cells there is impaired FTY720-induced microvascular remodeling (8A), suggesting that $S1P_3$ mediates the recruitment of circulating marrow-derived cells to remodeling vessels. BMC $S1P_3$ expression is critical for vascular remodeling (FIG. 8B).

Proposed Mechanism—BMC Mobilization

Figure 9:
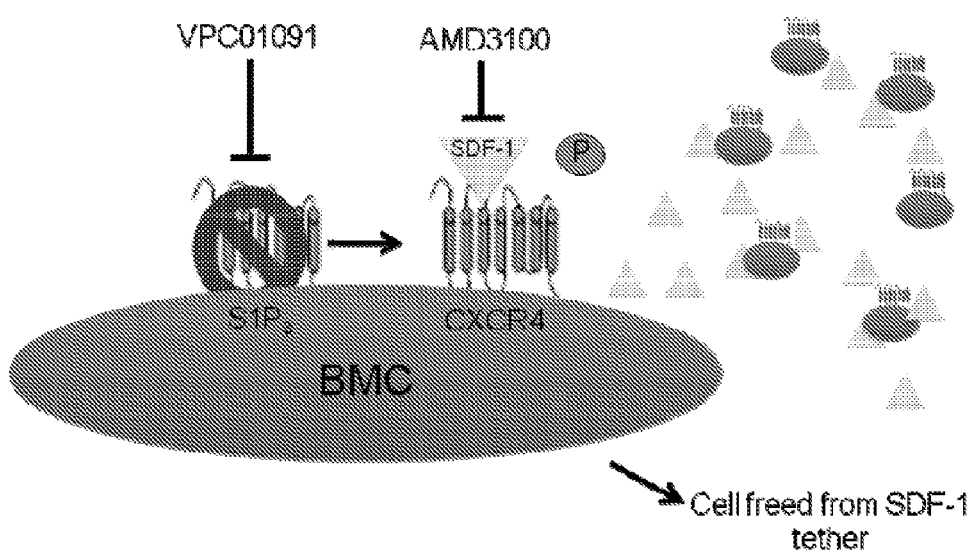
FIG. 9: Schematic of Proposed Mechanism for BMC Mobilization. Concurrent CXCR4 and $S1P_3$ receptor antagonism promotes marrow cell mobilization by abolishing SDF-1 gradient. VPC01091 leads to $S1P_3$ antagonism which decreases the phosphorylation of CXCR4. This, in conjunction with AMD3100, functionally antagonizes CXCR4, removing the ability of BMCs to respond to SDF-1 gradients. These BMCs are now capable of being mobilized into circulation.

Concurrent CXCR4 and antagonism promotes marrow cell mobilization by abolishing SDF-1 gradient. VPC01091 leads to $S1P_3$ antagonism which decreases the phosphorylation of CXCR4. This, in conjunction with AMD3100, functionally antagonizes CXCR4, removing the ability of BMCs to respond to SDF-1 gradients. These BMCs are now capable of being mobilized into circulation. See FIG. 9.

Figure 10A:
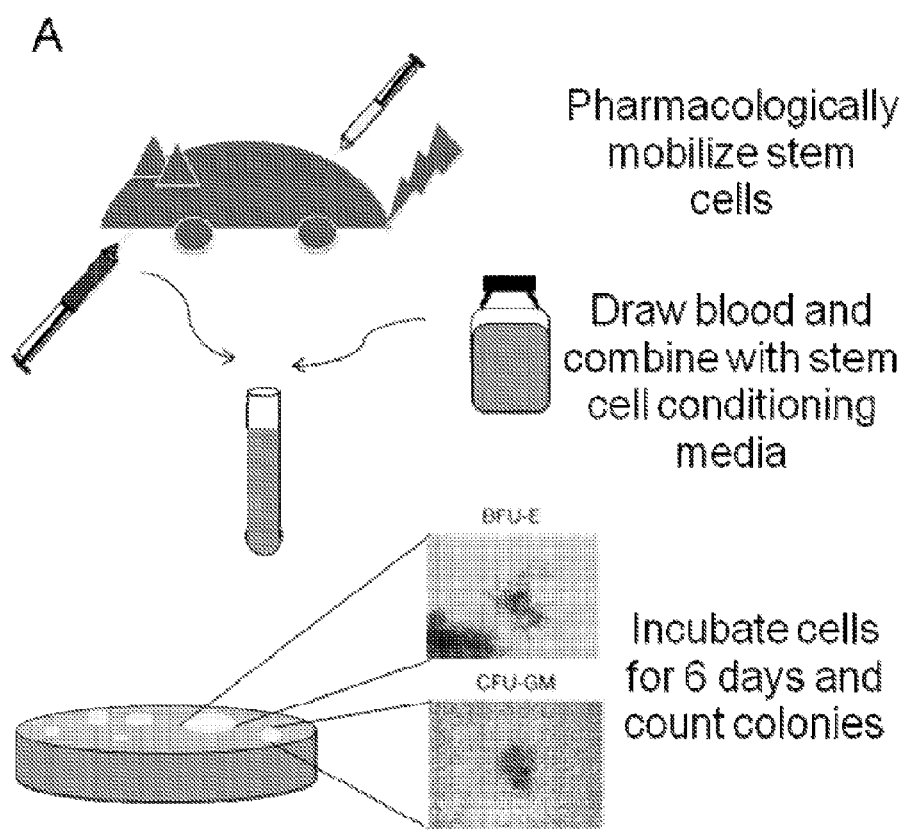
FIG. 10A: Schematic Protocol for Colony Forming Unit (CFU) stem cell mobilization assay (A).
Figure 10B:
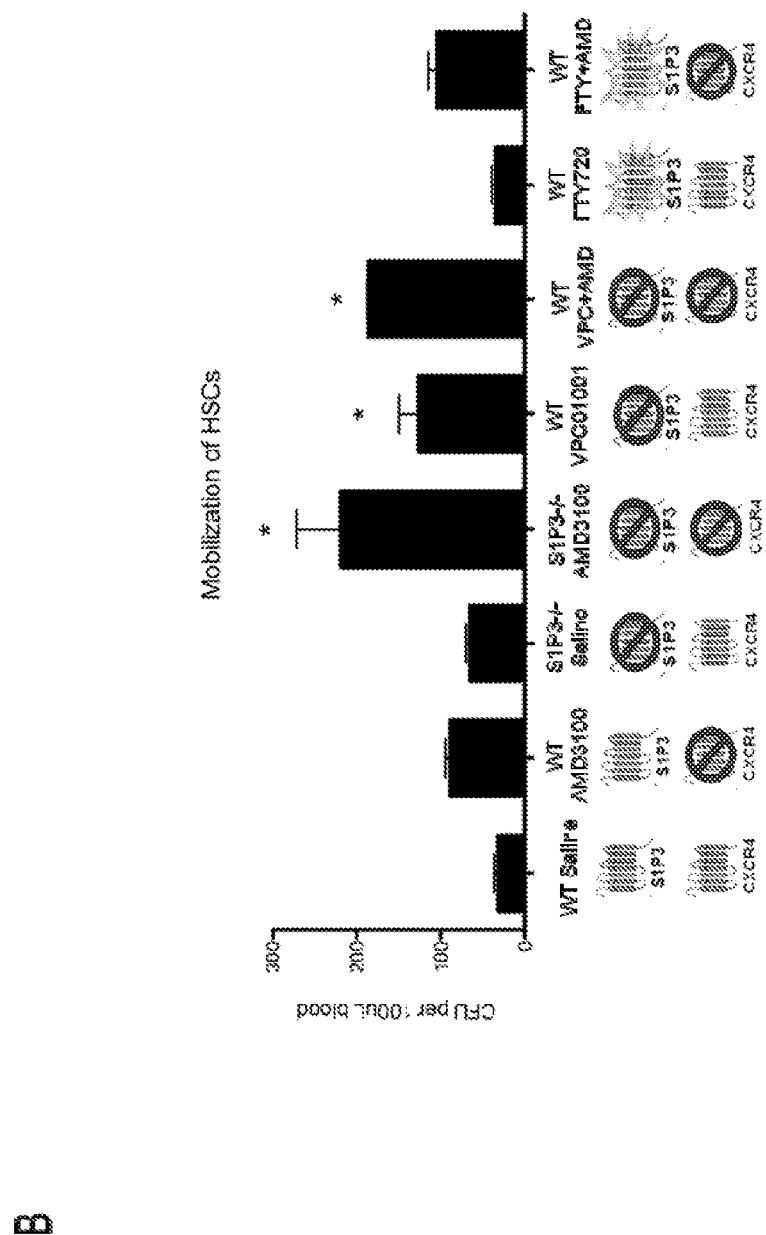
FIG. 10B: Mobilization of HSCs—Graphical illustration of number of CFUs after 6 days from 100 uL peripheral blood (B). Control, AMD3100, $S1P_3-/-$, VPC01091, FTY720, and combinations thereof.
Figure 10C:
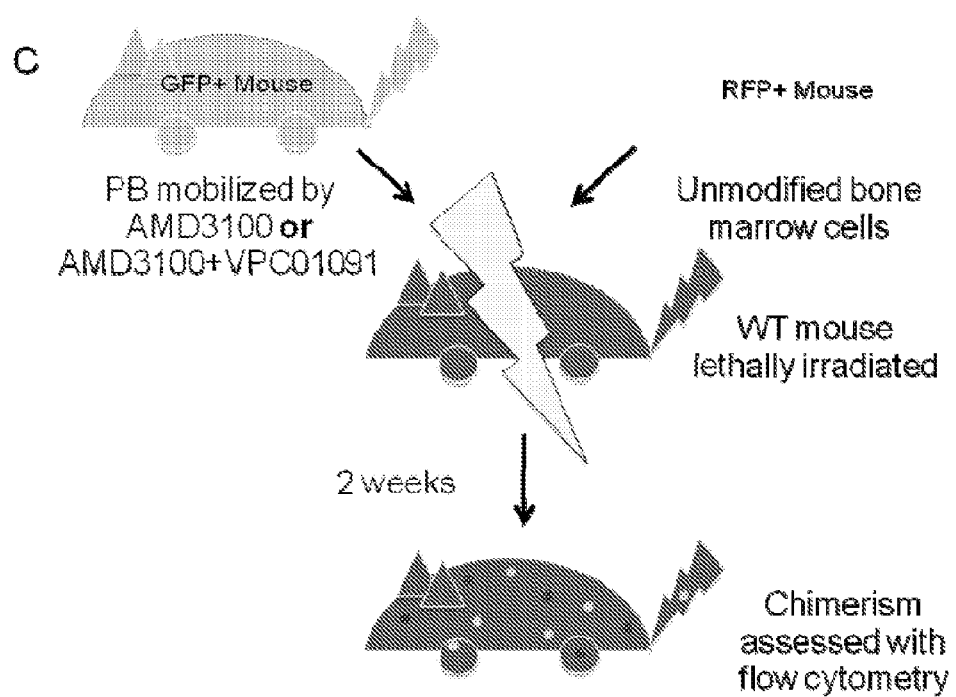
FIG. 10C: Schematic of bone marrow transplantation after with peripheral blood after lethal irradiation (C).
Figure 10D:
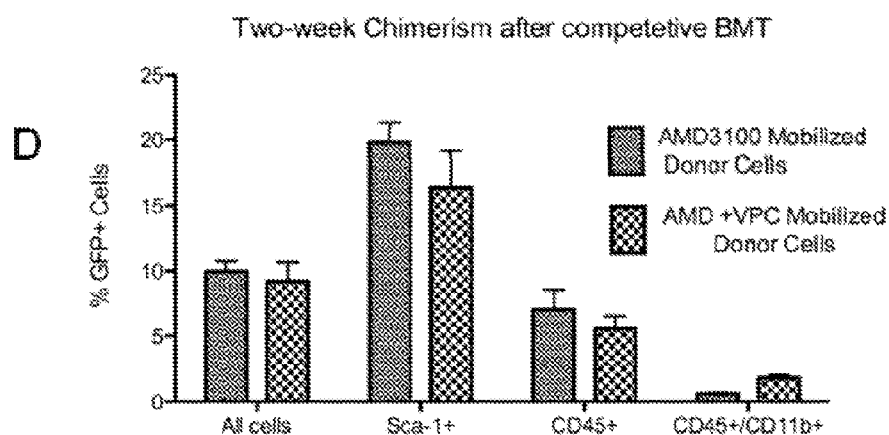
FIG. 10D: Two-week Chimerism after competitive BMT with equal numbers of mobilized cells: Graphical illustration that VPC01091 does not impair engraftment and repopulation efficiency in vivo (D).
Figure 10E:
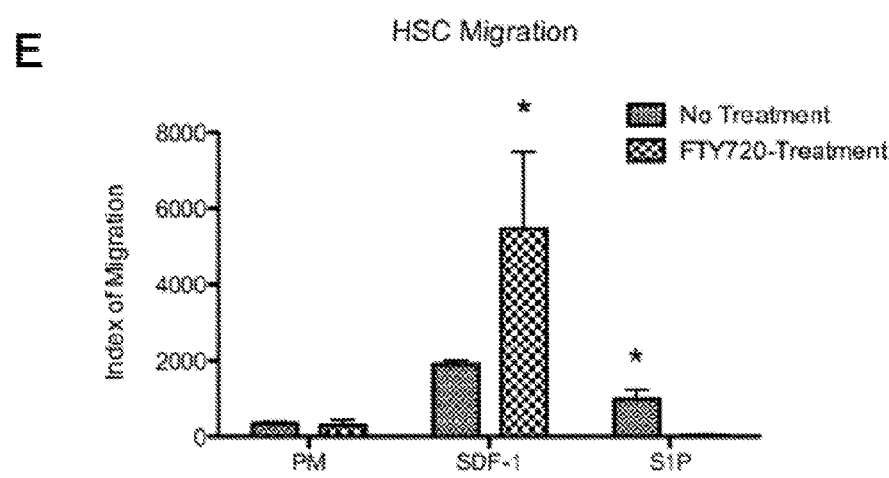
FIG. 10E: $Lineage1^-/Sca1^+/c-kit^+$ HSC Migration toward SDF-1 and S1P: Graphical illustration that FTY720 pretreatment improves homing to SDF-1 and abolishes S1P homing (E).

$S1P_3$ Antagonism Selectively Mobilizes Stem Cells without Affecting Ability to Engraft and FTY720 Enhances SDF-1 Homing The protocol for Colony Forming Unit (CFU) stem cell mobilization assay is schematically illustrated in FIG. 10A. The number of CFUs after 6 days from 100 uL peripheral blood is illustrated in FIG. 10B. The results of the study of mobilization of HSCs using various treatments are demonstrated in FIG. 10B. The protocol for bone marrow transplantation with peripheral blood after lethal irradiation is demonstrated in FIG. 10C. It can be seen in FIG. 10D that VPC01091 does not impair engraftment and repopulation efficiency in vivo. It can be seen in FIG. 10E that FTY720 pretreatment improves homing to SDF-1 and abolishes S1P homing.

Conclusions

It is disclosed herein that local $S1P_1/S1P_3$ activation prevents inflammatory cell recruitment and promotes microvascular remodeling through BMCs.

It is also disclosed herein that FTY720 enhances tortuosity and vessel remodeling in ischemic environments and recruits CX3CR1+ cells to vessels.

The unexpected result is disclosed herein that concurrent pharmacological inhibition of CXCR4 and $S1P_3$ receptors significantly mobilizes hematopoietic stem cells into circulation with the ability to engraft in the host and repopulate blood cells. FTY720-pre-treatment enhances this engraftment.

Modulation of the S1P receptor signaling axis may be a novel therapeutic strategy for the selective in situ mobilization and recruitment of stem cells for tissue engineering and stem cell based therapies.

Example 2

Sphingosine-1-Phosphate (S1P) Receptors Modulate Endogenous Stem Cell Mobilization and Homing for Bone Regeneration It is already known that coating allografts with FTY720, an $S1P_3$ agonist, increases the rate of critical size defect healing by enhancing homing of host-derived CXCR4+ stem/progenitor cells such as mesenchymal stem cells (MSCs). These experiments demonstrate that pharmacological inhibition of S1P$_3$ using VPC01091 significantly increases mobilization of BMSCs into peripheral blood resulting in accelerated bone repair in rat cranial defects. Additionally, MSCs pre-treated with FTY720 exhibit increased migration towards SDF-1, a CXCR4+ ligand and critical component of the bone marrow niche. These findings advocate the significant role of S1P$_3$ in stem cell chemotaxis. Additionally, treating animals with both FTY720 coated allografts locally and VPC01091 systematically is beneficial if controlled temporally. Without wishing to be bound by any particular theory, it is proposed herein that S1P$_3$ receptor antagonists aids in the mobilization of MSCs, while agonists of the same receptor are critical for stem cell recruitment. Thus, suggesting the presence of a push-pull mechanism that is dictated by S1P receptor specific small molecules.

Materials and Methods

Bone Defects 5 mm cranial defects were made in 36 nine weeks old Sprague Daley rats, which were divided into 4 groups (n=9). The rats were treated with a systemic dose of 1 mpk VPC01091, FTY720 coated semi-circular allograft, FTY720 coated semi-circular allograft+a systemic dose of 1 mpk VPC01091 or left untreated. VPC01091 was given the day after surgery and 3 weeks post-surgery. Hemavet (Drew Scientifics) was used to measure the concentrations of blood cells at days 0, week 1 and week 2 (n=6) (data not shown). The amount of bone regeneration was measured bi-weekly with microCT imaging (n=3-9). Flow cytometry was performed according to standard procedures on the tissue harvested from the defect sites at week 3 (n=3), and from peripheral blood at week 6 (n=3). Monoclonal antibodies (Invitrogen, Abeam) for rat CD45, CD11b, CD54, CD90 were used in both cases. Mason's Trichrome and H&E staining were done for done for all groups (n=3).

Methods for preparing bone allografts and for the use of polymer coatings to deliver compounds such as FTY720 are described in Int. Pat. Pub. No. WO 2010/118298 (Botchwey; published Oct. 14, 2010), Petrie Aronin et al. (Tissue Engineering, 2010, 16:6:1801; electronically published Mar. 1, 2010) and in Sefcik et al. (2008, Biomaterials, 29:2869).

Transwell Migration and Homing Studies

Bone marrow cells were collected from the tibia of Sprague Daley rats (Charles River), scrum starved for 2 hours, and the cell suspension at 2×10$^6$ cells/ml was pre-treated with serum-free medium, or 10 ng/ml FTY720-P (Cayman) for 30 minutes and then were re-suspended in serum-free DMEM (Invitrogen). 100 μl of the pre-treated cell suspension was added to the top of 5 μm transwell inserts (Costar) in a 24-well plate. The bottom of the wells contained 600 μl of serum-free DMEM or 12.5 nM SDF-1 (ProspecBio). The cells were incubated at 37° C. for 4 hours, and then the number of cells at the top and the bottom of the transwells were counted using an automatic cell counter. The cells that migrated toward SDF-1 after pre-treatment with FTY720-P were collected from the bottom of the transwells and treated with monoclonal antibodies to CD45, CD11b and CD90 prior to flow analysis. Flow cytometry was performed according to standard procedures and was analyzed on a 9 color CyAn flow cytometer.

Results

Figure 11A:
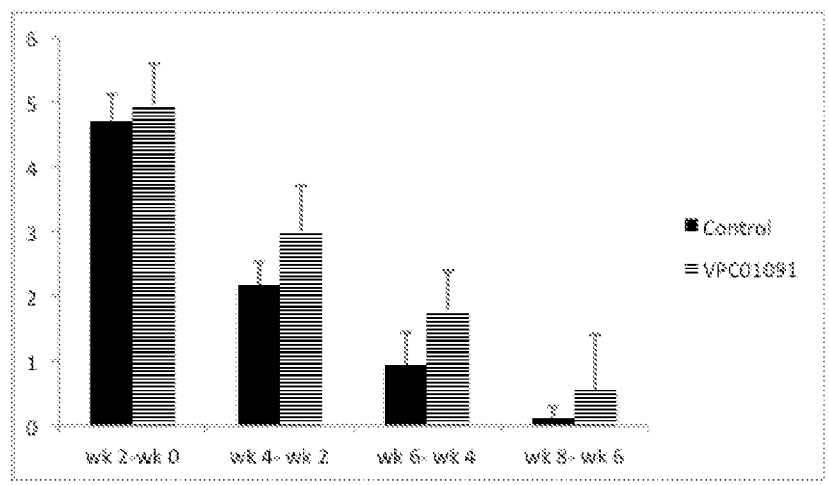
FIG. 11: Micro CT evaluation of bone growth and effect of FTY720 on MSC migration: 11A—Graphical illustration of control and 1 mg/kg VPC01091 treated critical size bone defects at various times; 11B—Graphical illustration of critical size boned defects at various times treated with FTY720-coated Allograft and FTY720-coated Allograft+1 mg/kg VPC01091. Ordinate represents Bone Volume in $mm^3$ Representative Images of control (11C) and VPC01091 (11D) treated groups. 11E—Graphic illustration showing that the total number of cells migrating toward SDF-1 significantly increased after being treated with FTY720-P. Cells were in plain medium or pre-treated with FTY720 and tested for migration toward SDF-1. Ordinate—Number of Migrated Cells. 11F—Graphic illustration demonstrating that a higher percentage of CD90+/CD45-/CD11b-cells migrates toward SDF-1 after pre-treatment with FTY720-P. Left bar—CD90+ CD11b-CD45-; Right bar-CD11b+ CD45+; Ordinate—Number of Cells.
Figure 11B:
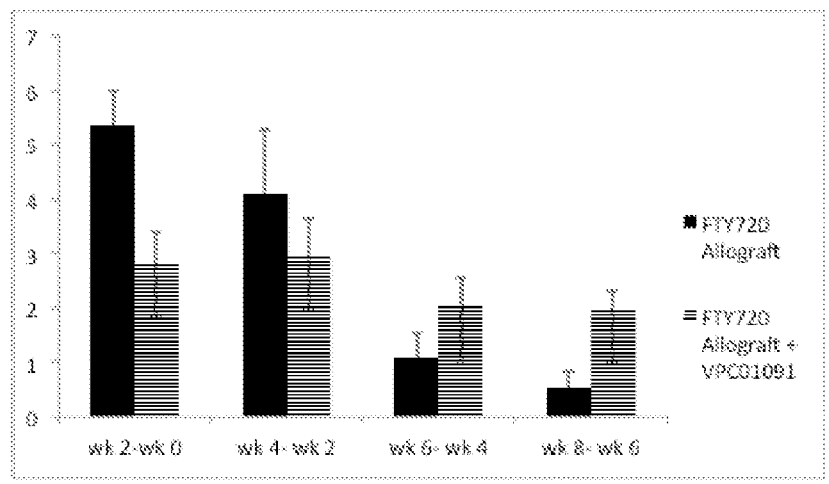
Figure 11C:
Figure 11D:
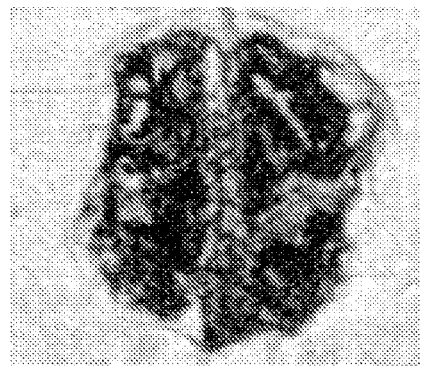
Figure 12A:
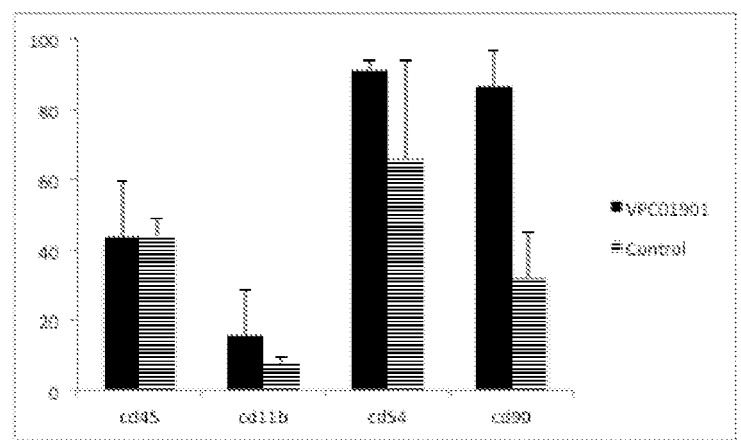
FIG. 12: Graphical illustrations of flow cytometric analysis of defect tissue at week 3 (A) and blood at week 6 (B). Black bars represent VPC01091 treatment and the horizontal lines represent Control groups. The abscissa indicates cd11b, cd45, cd54, and cd90 groups. The ordinate indicates the % of total cells that are positive for the different groups.
Figure 12B:
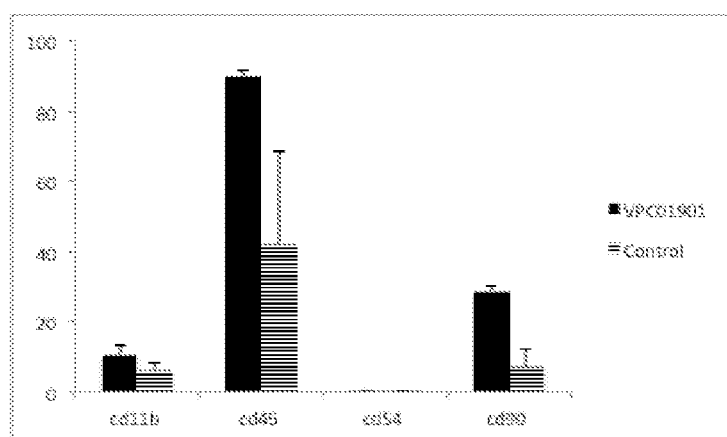

Treatment with systemic VPC01091 resulted in substantial bi-weekly increase in bone regeneration compared to the empty defect controls (FIGS. 11a, 11c, 11d). This group also showed an increase in the percentage of CD54 and CD90 positive cells (rats MSC markers) in the defect region at week 3 (FIG. 12a) and in the blood at week 6 (FIG. 12b). Animals treated with FTY720 allografts showed a temporal response to VPC01091. Initially, they showed lesser bone growth compared to just FTY720 treatment, but the trend reversed after week 4.

Figure 11E:
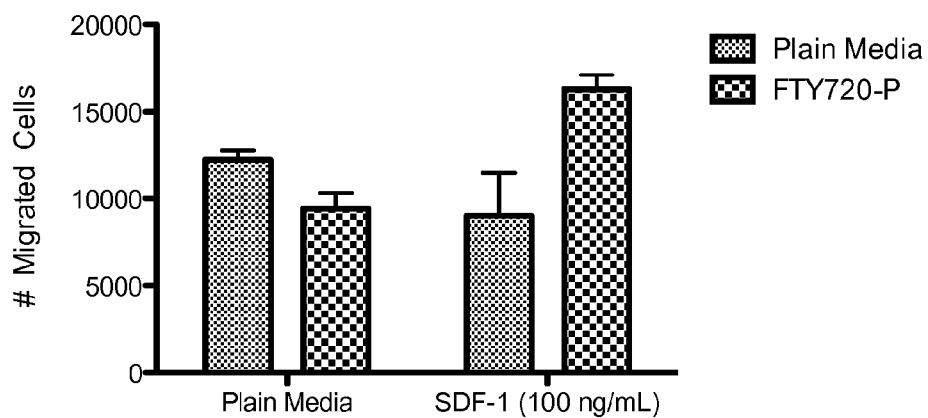
Figure 11F:
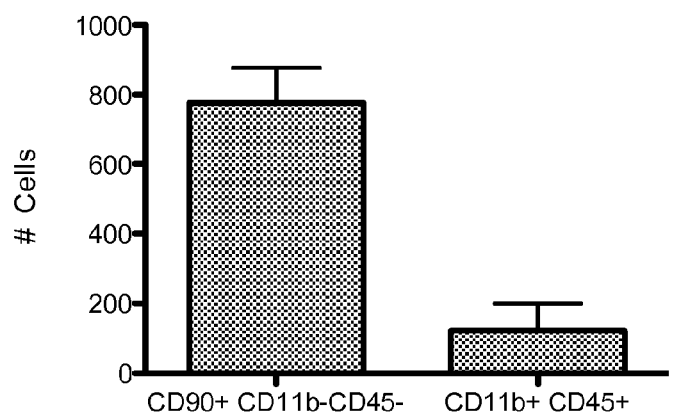

Transwell assays were conducted on BMCs treated with FTY720 to assess migration toward SDF-1 and it was found that a high percentage of the cells that migrated were mesenchymal stem cells. FIG. 11E shows that the total number of cells migrating toward SDF-1 significantly increased after being treated with FTY720-P. FIG. 11F shows that a higher percentage of CD90+; CD45−/CD11b− cells migrates toward SDF-1 after pre-treatment with FTY720-P. This suggests that FTY720 could recruit mesenchymal stem cells toward injury sites where SDF-1 concentrations are known to be high.

Discussion

These results indicate that a systemic treatment with VPC01091 will significantly accelerate bone regeneration in the absence of any local implant. However, the effectiveness of locally released FTY720 to promote healing requires recruitment of BMSCs via S1P$_3$, suggesting that the time of systemic delivery of a S1P$_3$ antagonist is crucial for the body to engage in this push-pull mechanism of endogenous stem cells. This manifests in the fact that the rate of increase in bone volume at later time points is the highest for the group treated with both FTY720 allograft and VPC01091 systemically. The presence of an increased number of MSCs both in the blood, and defect region tissue denotes that the cells required for bone healing are being mobilized into the blood, and recruited to the defect site as late as 6 weeks after injury. Thus, this study shows that the rate of bone growth in large defects can be controlled by a combination of S1P receptor specific small molecules in a time dependent manner. The recruitment of CXCR4+ stem/progenitor cells and enhancement of bone defect healing via neovascularization and osseous tissue in-growth can be achieved through selective targeting and activation of S1P receptors.

Significance

We propose the systemic use of an S1P$_3$ receptor antagonist, VPC01091, to mobilize endogenous stem cells in order to increase bone regeneration. Such endogenous stem cell therapy can be used to enhance bone regeneration in instances when there is substantial soft tissue damage and/or exogenous stem cell transplant is not feasible. This treatment can be used in conjunction with the other compounds and methods disclosed herein.

Endogenous stem cell therapies have been used in various other ailments like cardiovascular infarctions and can prove to be as effective in bone healing.

Example 3

Stem and Progenitor Cell Mobilization and Engraftment Via S1P$_3$ Receptor Signaling, S1P$_3$ Receptor Signaling, and Chemokine Receptor Signaling The human body has the ability to regenerate cells, repair tissues, and heal wounds through the differentiation and proliferation of multipotent stem cells. By applying the appropriate temporal and spatial molecular signals we can design strategies to recruit regenerative stem cells to sites of repair. Sphingosine 1-phosphate (S1P) is a pleiotropic, autocrine and paracrine signaling molecule that binds to a family of five high affinity G-coupled receptors ($S1P_1$-$S1P_5$) to direct a wide range of biological processes including marrow cell trafficking.

Materials and Methods

AMD3100 (Sigma) (a CXCR4 antagonist) and VPC01091 (an $S1P_1$ agonist/$S1P_3$ antagonist) were delivered at 5 mg/kg wt. intraperitoneally to C57BL/6 mice one hour before peripheral blood (PB) isolation. Stem cell content was analyzed with flow cytometry. PB was plated on Methocult stem cell differentiating media (Stem Cell Technologies) for 6 days and colony-forming units (CFU) were counted. Hematopoietic stem cells (HSC) were sorted from C57BL/6 marrow and pre-treated with 15 nM VPC01091 and assayed in transwell migration assays toward SDF-I and S1P. BMCs were pre-treated with AMD3100 and/or VPC01091 and seeded on FBMD-1 stromal cells to quantify engraftment. Wild type C57BL/6 mice were lethally irradiated and reconstituted with PB mobilized in GFP+ mice. Donor repopulation of blood cells was assessed for 12 weeks with flow cytometry. All flow cytometric analyses were performed with Sca-1, CD11b, CD45, c-kit and Lin1 (Ab-Cam, Biolegend).

Results

Figure 13:
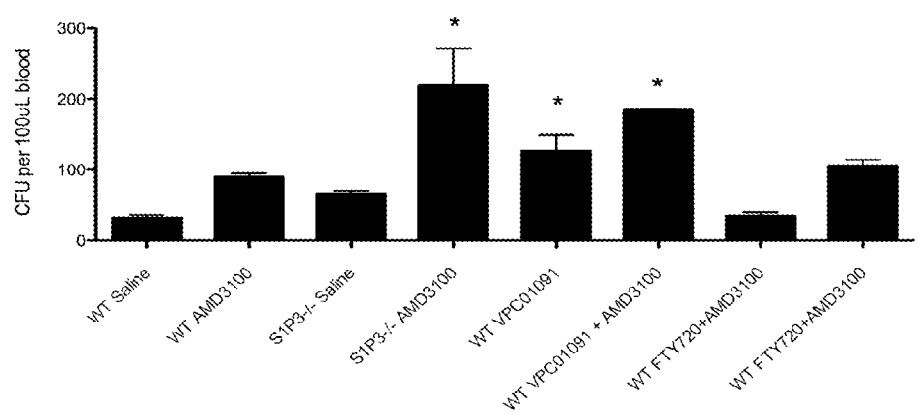
FIG. 13: Graphical illustration that antagonism of $S1P_3$ significantly enhances mobilization of HSCs. Concurrent $S1P_3$ and CXCR4 antagonism further increases the mobilization of HSCs. $S1P_3$ activation with FTY720 ($S1P_3$ agonist) inhibited this increase in HSC mobilization.

Concurrent pharmacological antagonism of $S1P_3$ and CXCR4 significantly enhanced the number of CFUs in PB compared to saline-treated mice (FIG. 13). VPC01091 pre-treatment desensitized Lin1$^-$/C-kit$^+$/Sca1$^+$ HSCs cells to a SDF-1 gradient but sensitized them towards S1P, which was also shown in cobblestone area-forming cell assays. Concurrent $S1P_3$ and CXCR4 antagonism further increases the mobilization of HSCs. $S1P_3$ activation with FTY720 ($S1P_3$ agonist) inhibited this increase in HSC mobilization, while antagonism of $S1P_3$ significantly enhances mobilization of HSC.

Figure 14:
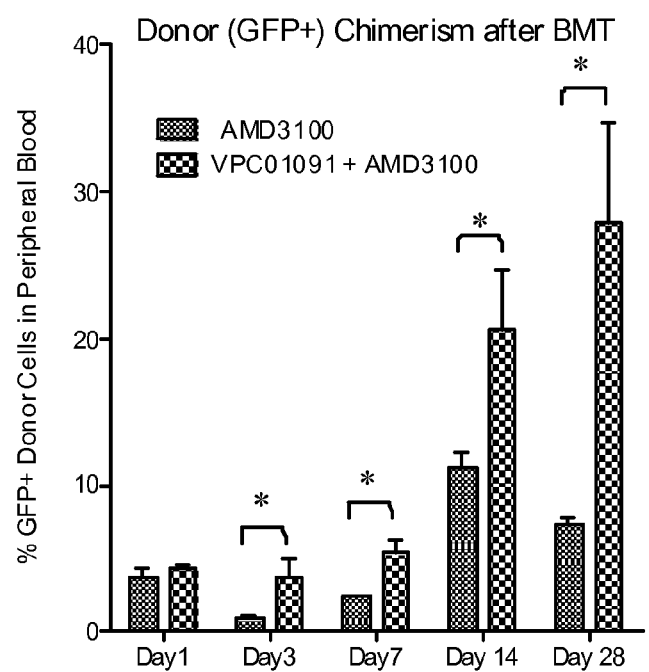
FIG. 14: Donor (GFP+) Chimerism after BMT—BMCs were mobilized in GFP+ with AMD3100 or VPC01091+ AMD3100 and equal volumes of blood were used to reconstitute irradiated mice. Up to two months after BMT, there is significantly increased chimerism after VPC01091-mobilization. Abscissa—Days 1, 3, 7, 14, and 28. Ordinate—% GFP+Donor Cells in Peripheral Blood.
Figure 15:
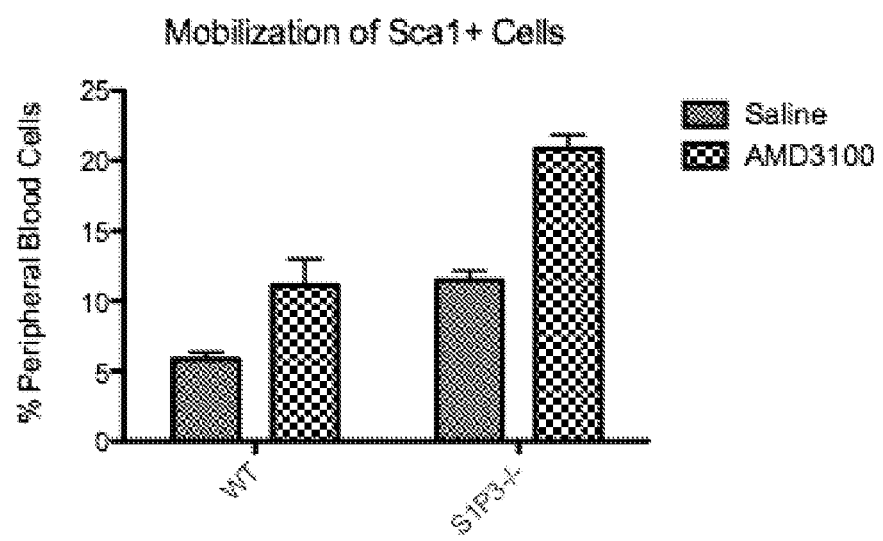
FIG. 15: Mobilization of Sca1+ Cells: Saline or 5 mg/kg weight AMD3100 in saline was injected intraperitoneally into WT C57Bl/6 mice or $S1P_3-/-$ mice. One hour after injection peripheral blood was harvested with a cardiac stick, RBCs were lysed with ammonium chloride and the WBC fraction was stained with antibodies against Sca1. AMD3100 significantly mobilized Sca1+ progenitor cells in wild type mice. $S1P_3-/-$ mice, without AMD3100 have significant increases in the basal number of circulating Sca1+ cells. AMD3100 also significantly enhances the mobilization of these cells in the $S1P_3-/-$ mice.
Figure 16:
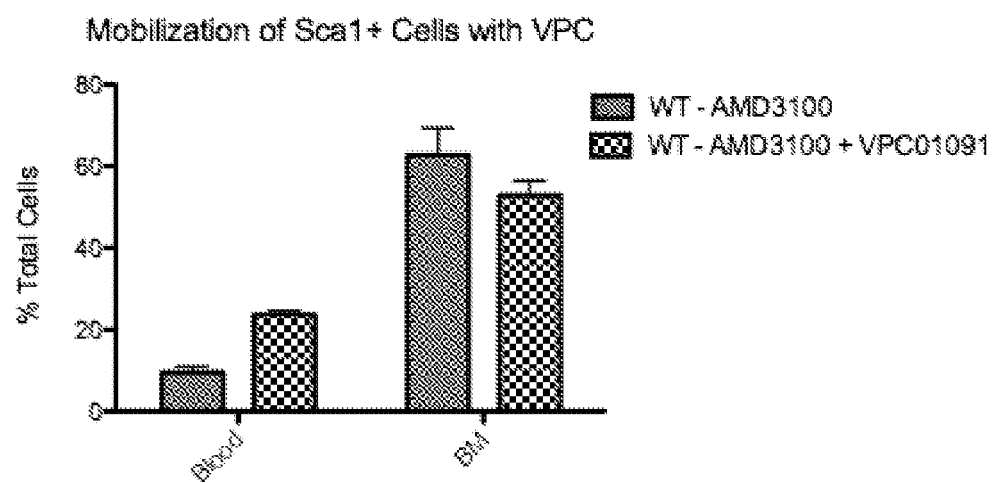
FIG. 16: Mobilization of Sca1+ Cells with VPC01091: 5 mg/kg VPC01091 or carrier was injected intraperitoneally and 30 minutes later 5 mg/kg weight AMD3100 in saline was injected intraperitoneally into WT C57Bl/6. One hour after AMD3100 injection peripheral blood or bone marrow was harvested, RBCs were lysed with ammonium chloride and cells were stained with antibodies against Sca1. AMD3100+ VPC01091 significantly mobilized Sca1+ progenitor cells into the blood above AMD3100 alone. Mice that received the combination also showed a decrease in BM percentage of Sca1+ cells corroborating that these cells are indeed mobilized from the bone marrow.

Mice repopulated with cells mobilized by VPC01091 do not lose their ability to engraft in the host and enhanced mobilization leads to enhanced chimerism (FIG. 14). BMCs were mobilized in GFP+ mice with AMD3100 or VPC01091+AMD3100 and equal volumes of blood were used to reconstitute irradiated mice. Up to two months after BMT, there was significantly increased chimerism in mice that received VPC01091+AMD3100-mobilized grafts. Studies were also done to demonstrate mobilization of Sca1+ cells (FIG. 15). Saline or 5 mg/kg weight AMD3100 in saline was injected intraperitoneally into WT C57Bl/6 mice or $S1P_3$-/- mice. One hour after injection peripheral blood was harvested with a cardiac stick, RBCs were lysed with ammonium chloride and the WBC fraction was stained with antibodies against Sca1. AMD3100 significantly mobilized Sca1+ progenitor cells in wild type mice. $S1P_3$-/- mice, without AMD3100 showed significant increases in the basal number of circulating Sca1+ cells. AMD3100 also significantly enhanced the mobilization of these cells in the $S1P_3$-/- mice. FIG. 16 demonstrates mobilization of Sca1+ Cells with VPC01091. 5 mg/kg VPC01091 or carrier was injected intraperitoneally and 30 minutes later 5 mg/kg weight AMD3100 in saline was injected intraperitoneally into WT C57Bl/6. One hour after AMD3100 injection peripheral blood or bone marrow was harvested, RBCs were lysed with ammonium chloride and cells were stained with antibodies against Sca1. AMD3100+ VPC01091 significantly mobilized Sca1+ progenitor cells into the blood above AMD3100 alone. Mice that received the combination also showed a decrease in BM percentage of Sca1+ cells corroborating that these cells are indeed mobilized from the bone marrow.

Figure 17:
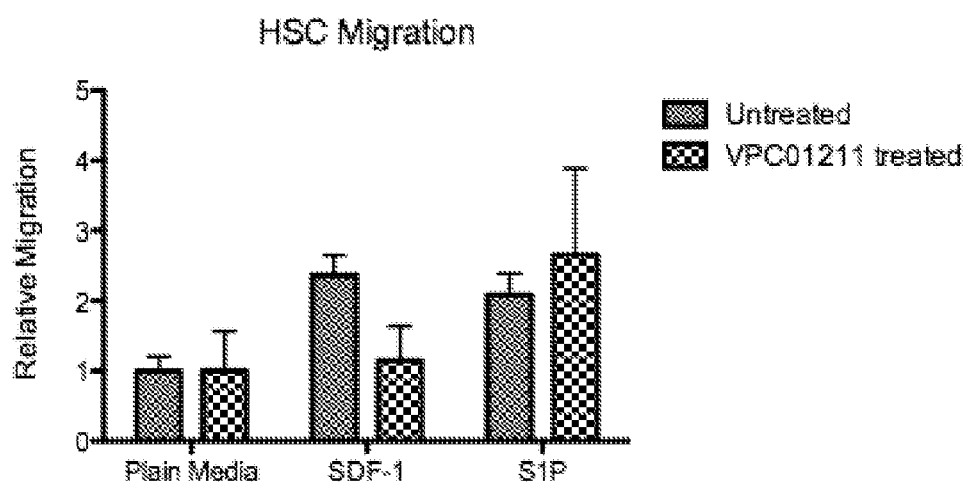
FIG. 17: HSC Migration: Lineage1−/Sca1+/c-kit+ (LSK) hematopoietic stem cells were sorted and serum starved for two hours. Cells were pre-treated with 15 nM VPC01211 or not and plated for transwell migration assays toward plain media, SDF-1 or S1P. VPC01211 pre-treatment abrogated migration towards SDF-1 but did not affect migration towards S1P. Not significant. p=0.0502.

Hematopoietic stem cell migration was also studied (FIG. 17). Lineage1-/Sca1+/c-kit+ (LSK) hematopoietic stem cells were sorted and serum starved for two hours. Cells were pre-treated with 15 nM VPC01211 or not and plated for transwell migration assays toward plain media, SDF-1 or S1P. VPC01211 pre-treatment abrogated migration toward SDF-1 but did not affect migration toward S1P.

Figure 18:
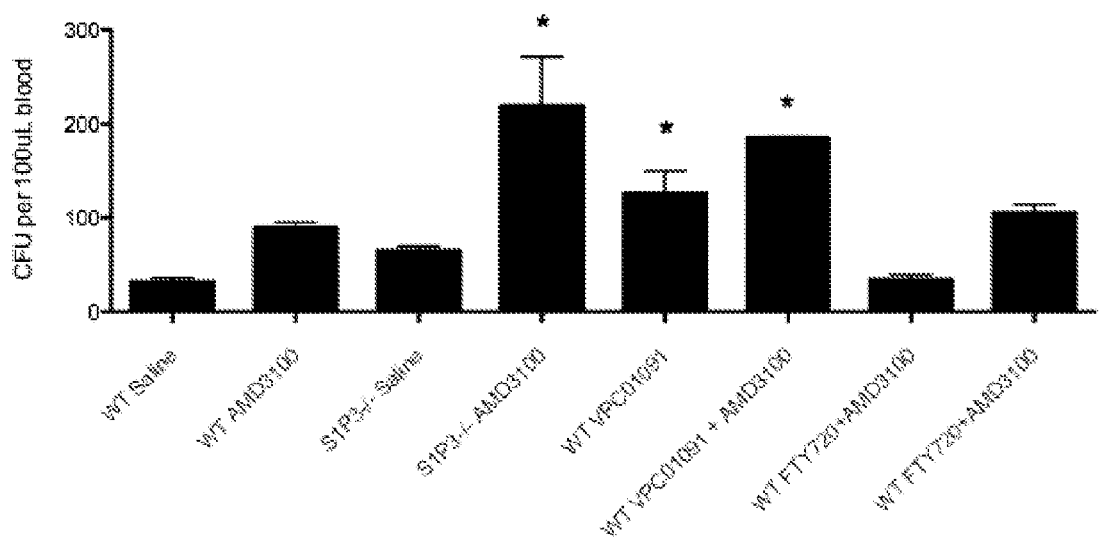
FIG. 18: WT C57Bl/6 mice received 5 mg/kg weight of various combinations of S1PR compounds and AMD3100. 100 μL blood was plated on methocult stem cell differentiative media and after 6 days colony forming units were quantified. $S1P_3$ inhibition pharmacologically, with VPC01091, significantly enhanced CFUs formed. AMD3100 in $S1P_3$−/− mice or with VPC01091 also significantly increased CFUs compared to WT Saline. Ordinate—CFU per 100 μA blood. *—statistical difference from control.
Figure 19:
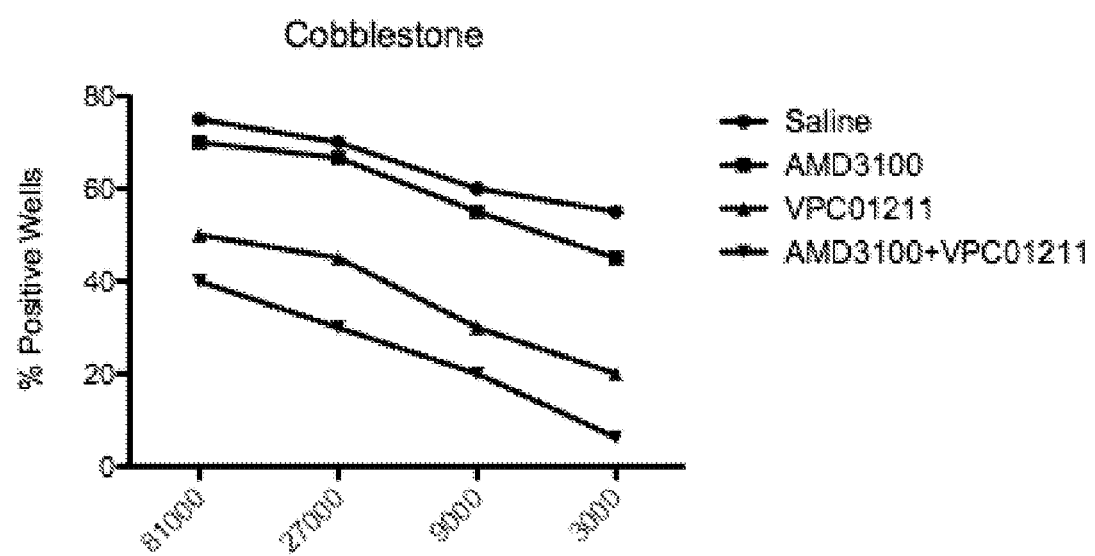
FIG. 19: Cobblestone: Whole BMCs were pre-treated with Saline, AMD3100, VPC01211 or "AMD3100+ VPC01211" for 30 minutes and plated on a bone marrow stromal cell layer of confluent FBMD-1 cells for cobblestone area-forming assays. Two hours after plating the treated BMCs they were washed to remove those cells which did not attach. The combination of drugs showed the least engraftment, suggesting that CXCR4 and $S1P_3$ inhibition would decrease affinity of cells for the bone marrow niche. VPC01211 alone showed less engraftment than AMD3100. Ordinate—% Positive Wells.

Animal studies (FIG. 18) showed the effects of combinations of S1P receptor regulators and chemokine receptor regulators. 100 μL blood was plated on methocult stem cell differentiation medium and after 6 days colony forming units were quantified. $S1P_3$ inhibition pharmacologically with VPC01091 significantly increased CFUs formed from peripheral blood. AMD3100 in S1P3-/- mice or with VPC01091 also significantly increased CFUs compared to WT Saline. In another study (FIG. 19) whole BMCs were pre-treated with either saline, AMD3100, VPC01211 or "AMD3100+VPC01211" for 30 minutes and plated on a bone marrow stromal cell layer for cobblestone area-forming cell assays. The combination of drugs showed the least adhesion, suggesting that CXCR4 and $S1P_3$ inhibition would decrease affinity of cells for the bone marrow niche. VPC01211 alone showed less engraftment than AMD3100.

Figure 20:
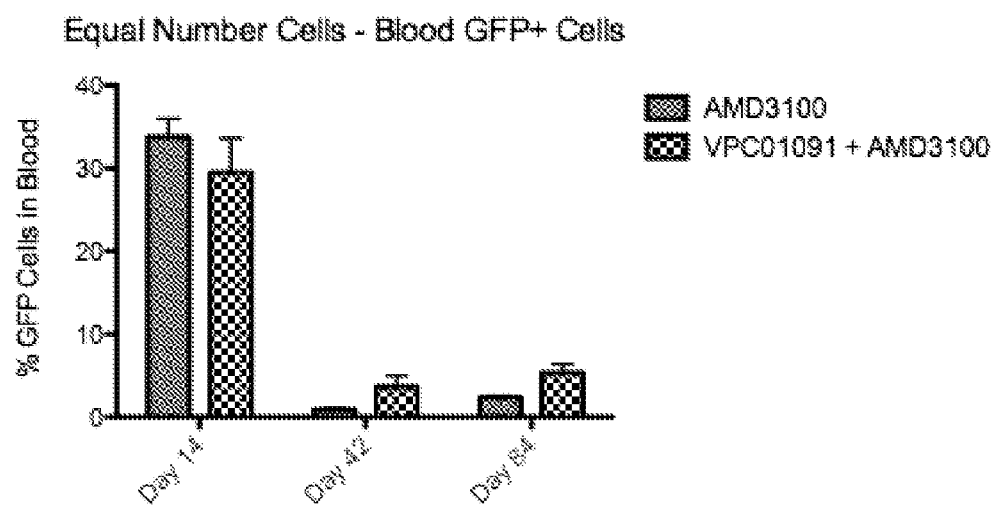
FIG. 20: Equal Number Cells—Blood GFP+ Cells: GFP+ mice received either AMD3100 alone or "VPC01091+ AMD3100" to mobilize stem cells and an equal number ($2 \times 10^6$ per mouse) of mobilized cells was used to reconstitute C57Bl/6 mice after lethal irradiation. Blood was drawn for 84 days to assess chimerism. The ability of donor cells to engraft was not impaired after VPC01091-induced mobilization compared to AMD3100 alone. n.s. Abscissa—days. Ordinate—% GFP Cells in Blood.

In another set of animal studies (FIG. 20), GFP+ mice received either AMD3100 alone or "VPC01091+AMD3100" to mobilize stem cells and an equal number ($2\times10^6$ per mouse) of mobilized cells was used to reconstitute C57Bl/6 mice after lethal irradiation. Blood was drawn for 84 days to assess chimerism. The ability of donor cells to engraft was not impaired after VPC01091-induced mobilization compared to AMD3100 alone. It was also demonstrated (FIG. 21) that there are no differences in donor GFP+/Sca1+/CD45+/CD11b+ peripheral blood content up to 84 days post transplant. Cells included—Host cells, PB Donor Cells and BM Donor cells and treatments AMD3100, A+V, AMD3100 Sca1+, A+V Sca1+, AMD3100 CD45+, A+V CD45+, AMD3100 CD11b+, and A+V CD11b+. Further studies (FIG. 22) showed that there was no difference in donor GFP+/Sca1+/CD45+/CD11b+ bone marrow content at 84 days post transplant. Cells tested included—Host cells, PB donor cells and BM donor cells were tested. Treatments included—AMD cells, A+V cells, AMD Sca1+, A+V Sca1+, AMD CD45+, A+V CD45+, AMD CD11b+, and A+V CD11b+.

Figure 21:
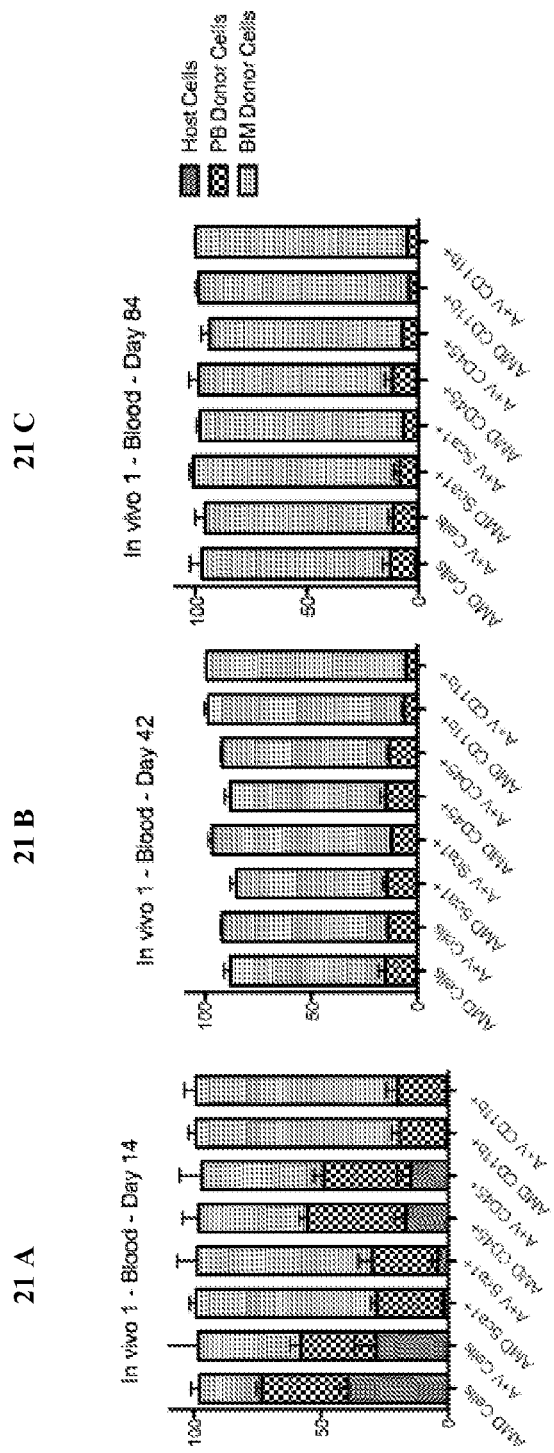
FIGS. 21 (A, B & C): Graphical illustration of no differences in donor GFP+/Sca1+/CD45+/CD11b+ peripheral blood content up to 84 days post transplant with equal numbers of cells. 21A—Day 14; 21B—Day 42; 21C—Day 84; Cells included—Host cells, PB Donor Cells and BM Donor cells; Abscissa—AMD cells, A+V cells, AMD Sca1+, A+V Sca1+, AMD CD45+, A+V CD45+, AMD CD11b+, and A+V CD11b+.
Figure 22:
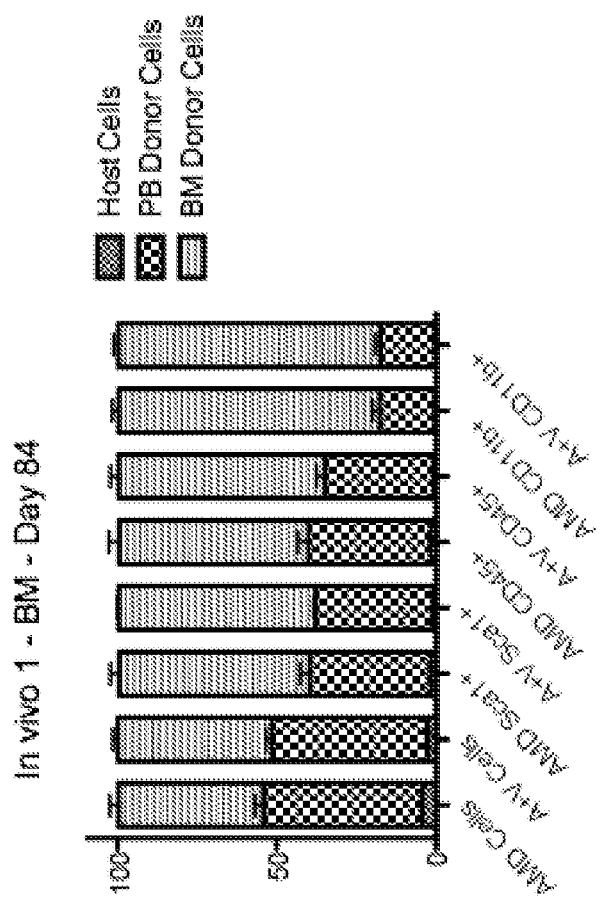
FIG. 22: Graphical illustration of no difference in donor GFP+/Sca1+/CD45+/CD11b+ bone marrow content at 84 days post transplant. Host cells, PB donor cells and BM donor cells were tested. Abscissa—AMD cells, A+V cells, AMD Sca1+, A+V Sca1+, AMD CD45+, A+V CD45+, AMD CD11b+, and A+V CD11b+.
Figure 23:
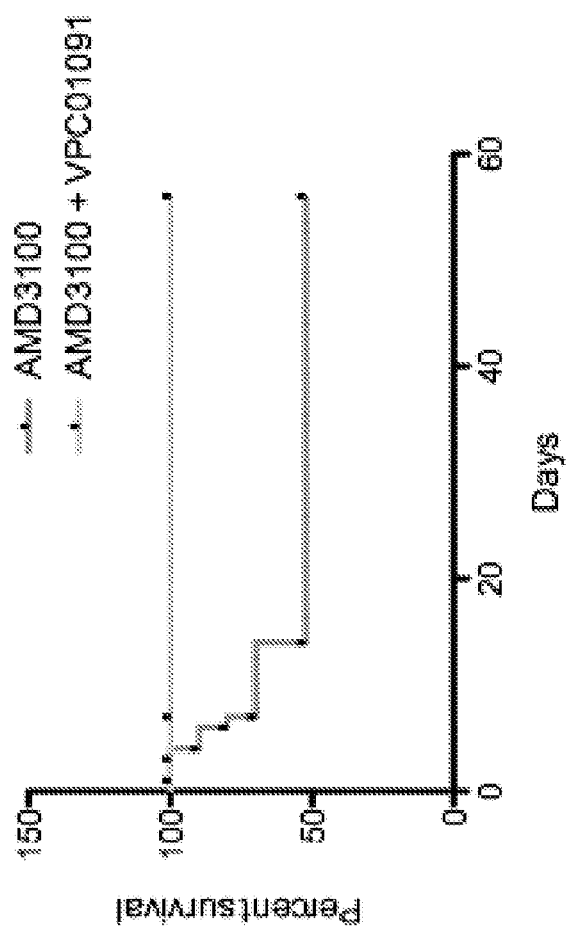
FIG. 23: Graphical illustration of survival of mice reconstituted with donor peripheral blood stem cells. By day 14 post transplantation, survival was 50% in the group with transplanted cells mobilized by AMD3100 alone. There was 100% survival in the group that received cells mobilized with the combination of AMD3100 and VPC01091. Ordinate—Percent Survival. Abscissa—Days.

Experiments were also done to examine the survival of mice reconstituted with equal volumes of donor peripheral blood (FIG. 21). By day 14 post transplantation, survival was 50% in the group with transplanted cells mobilized by AMD3100 alone. There was 100% survival in the group that received cells mobilized with the combination of AMD3100 and VPC01091, demonstrating the superior results achieved with this combination.

Figure 24:
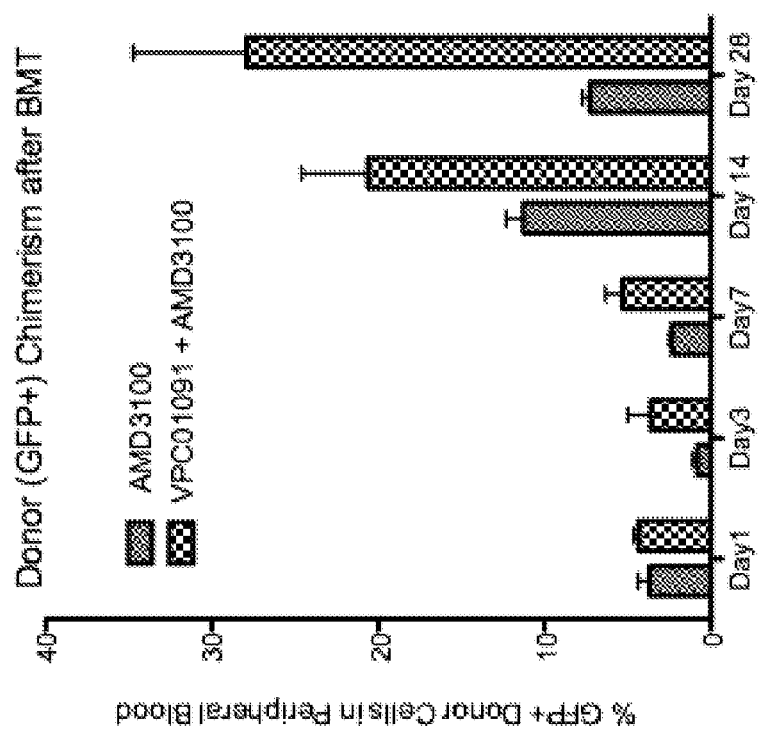
FIG. 24: Graphical Illustration of Donor (GFP+) Chimerism after BMT: Equal volumes of mobilized cells were injected into C57Bl/6 mice after lethal irradiation. After 7 days, significant increase in donor chimerism with "VPC01091+AMD3100" mobilized donor cells. One group was treated with only AMD3100. Ordinate—% GFP+Donor Cells in Peripheral Blood. Abscissa—Days.
Figure 25:
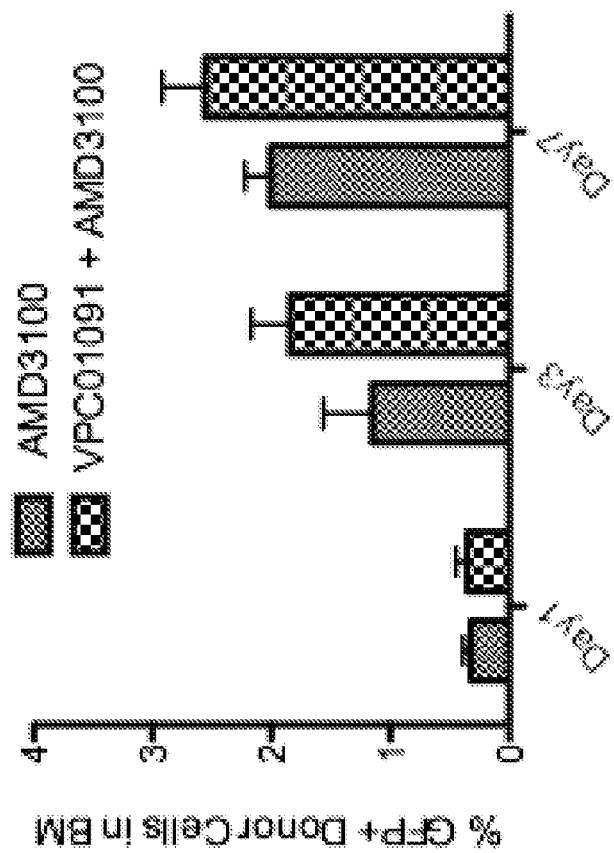
FIG. 25: Graphical illustration that donor (GFP+) cells are elevated in bone marrow of host mice after transplantation with cells mobilized in mice with "VPC01091 and AMD3100: compared to AMD3100 alone. Ordinate—% GFP+Donor Cells in BM. Abscissa—Days.

FIG. 24 shows the results of a study on donor (GFP+) chimerism after bone marrow transplantation (BMT). Equal volumes of mobilized blood were injected into C57Bl/6 mice after lethal irradiation from mice that had been mobilized with AMD3100 alone or AMD3100+VPC01091. After 7 days, a significant increase was found in donor chimerism with "VPC01091+AMD3100" mobilized donor cells. FIG. 25 demonstrates that donor (GFP+) cells are elevated in bone marrow of host mice after transplantation with cells mobilized in mice with "VPC01091 and AMD3100" compared to AMD3100 alone. It can be seen in FIGS. 26 (A & B) that on Day 1 post transplantation most blood and bone marrow cells are still host-derived and have not died from irradiation. There were no significant differences in host concentration of donor-derived blood cells between the two groups. Cells tested include—Host cells, PB donor cells and BM donor cells were tested and the treatments indicated on the figure include AMD cells, A+V cells, AMD Sca1+, A+V Sca1+, AMD CD45+, A+V CD45+, AMD CD11b+, and A+V CD11b+. It is further shown in FIGS. 27 (A & B) that on day 3 post transplantation the dominant cell types are still host-derived, but animals with cells mobilized with AMD3100+ VPC01091 show increased donor content. The blood cell fraction and BM cell fraction are shown and cells used include—Host cells, PB donor cells and BM donor cells, and the treatments included AMD cells, A+V cells, AMD Sca1+, A+V Sca1+, AMD CD45+, A+V CD45+, AMD CD11b+, and A+V CD11b+. FIGS. 28 (A & B) shows that on day 7 post transplantation the dominant cell types are still host-derived but animals with cells mobilized with AMD3100+ VPC01091 show increased donor content. FIG. 29 shows that on days 14 and 28 post transplantation most of the host-derived cells have died and the peripheral blood donor and bone marrow competitive transplant cells are dominant. There are significant increases in GFP+ donor cell chimerism in mice that received cells from mice mobilized with AMD3100+ VPC01091.

Discussion and Conclusions

By avoiding signaling on the CXCR4/SDF-1 axis, S1P receptor signaling can be used to mobilize marrow-derived stem cells into peripheral blood without affecting their ability to engraft in the host or at the repair site. By pre-treating cells with FTY720 we can enhance migration towards SDF-1, and abolish chemotaxis towards S1P, a competitive gradient in the circulation. By taking advantage of S1P receptor signaling we can significantly enhance the pool of marrow-derived stem cells for transplant and endogenous therapies as well as prime them to effectively engraft at the host site.

The present invention encompasses compositions and methods demonstrating that the rate of bone growth in large defects can be controlled by a combination of S1P receptor specific small molecules in a time dependent manner. The recruitment of CXCR4+ stem/progenitor cells and enhancement of bone defect healing via neovascularization and osseous tissue in-growth can be achieved through selective targeting and activation of S1P receptors. Concurrent pharmacological antagonism of $S1P_3$ and CXCR4 significantly enhanced the number of CFUs in peripheral blood compared to control treated animals. Animals repopulated with cells mobilized by VPC01091 do not lose their ability to engraft in the host and enhanced mobilization leads to enhanced chimerism.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Takafumi Kimura, et al., "The sphingosine 1-phosphate receptor agonist FTY720 supports CXCR4-dependent migration and bone marrow homing of human CD 34+ progenitor cells", Blood, 2004, 103: 4478-4486.
2. Veronique E. Miron, et al., "FTY720 Modulates Human Oligodendrocyte Progenitor Process Extension and Survival", Annals of Neurology, Vol. 63, No. 1, January 2008, 61-71.
3. Magda Kucia, et al., "Trafficking of Normal Stem Cells and Metastasis of Cancer Stem Cells Involve Similar Mechanisms: Pivotal Rose of the SDF-1-CXCR4 Axis", Stem Cells 2005:23:879-894.
4. Martin F. Ryser, et al., "$S1P_1$ overexpression stimulates S1P-dependent chemotaxis of human CD34+ hematopoietic progenitor cells but strongly inhibits SDF-1/CSCR4-dependent migration and in vivo living", Molecular Immunology 46 (2008) 166-171.
5. Carene E. Petrie Aronin, et al., "FTY720 Promotes Local Microvascular Network Formation and Regeneration of Cranial Bone Defects", Tissue Engineering, Part A, Vol. 16, No. 6, 2010, 16:6:1801-1809. Published Online 3/8/10.
6. Shaun M. Honig, et al., "FTY720 stimulates multidrug transporter- and cysteinyl leukotriene-dependent T cell chemotaxis to lymph nodes", The Journal of Clinical Investigtion, March 2003, Vol. 111, No. 5, 627-637.
7. Gabriele Seitz, et al., "The Role of Sphingosine 1-Phosphate Receptors in the Trafficking of Hematopoietic Progenitor Cells", Ann. N.Y. Acad. Sci. 1044: 84-89 (2005).
8. Myat Lin Oo, et al., "Immunosuppressive and Anti-angiogenic Sphingosine 1-Phosphate Receptor 1 Agonists Induce Ubiquitinylation and Proteasomal Degradation of the Receptor", Journal of Biological Chemistry, Vol. 282, No. 12, Mar. 23, 2007, 9082-9089.
9. Jason G. Cyster, "Chemokines, Sphingosine-1-Phosphate, and Cell Migration in Secondary Lymphoid Organs", Annu. Rev. Immunol., 2005. 23:127-59.
10. Lauren S. Sefcik, et al., "Selective Activation of Sphingosine 1-Phosphate Receptors 1 and 3 Promotes Local Microvascular Network Growth", Tissue Engineering, Part A, Vol. 17, Nos. 5 and 6, 2011: 617-629. Published Online 11/9/10.
11. Laura A. Paganessi, et al., "Effective mobilization of hematopoietic progenitor cells in G-CSF mobilization defective CD 26$^{-/-}$ mice through AMD3100-induced disruption of the CSCL12-CXCR4 axis", Experimental Hematology 2011:39:384-390.
12. Chao Song, "CXCR4 and matrix metalloproteinase-2 are involved in mesenchymal stromal cell homing and engraftment to tumors", Cytotherapy, 2010: Early Online, 1-13. Epub Online 12/20/10.
13. M. W. Laschke, et al., "Endothelial progenitor cells contribute to the vascularization of endometriotic lesions", Abstract, Am J Pathol. 2011, January: 178(1): 442-50. Epub 2010 Dec. 23.
14. Ha-Yon Kim, et al., "The CXCR4 Antagonist AMD3100 Has Dual Effects on Survival and Proliferation of Myeloma Cells In Vitro", Cancer Res. Treatment 2010: 42(4):225-234, Epub. 12/31/10.
15. Vijay K. Singh, et al., "Mobilized progenitor cells as a bridging therapy for radiation casualties: A brief review of tocopherol succinate-based approaches", Int. Immunopharmacol (2011), doi:10.1016/j.intimp.2011.01.017, 1-6.
16. Mieke Gouwy, et al., "CXCR4 and CCR5 ligands cooperate in monocyte and lymphocute migration and in inhibition of dual-tropic (R5/X4) HIV-1 infection", Eur. J. Immunol. 2011. 41: 1-11.
17. Sefcik et al. (2008, Biomaterials, 29:2869)

18. Int. Pat. Pub. No. WO 2010/118298 (Botchwey; published Oct. 14, 2010).

What is claimed is:

1. A method for mobilizing hemopoietic stem cells into circulation in a subject in need thereof, said method comprising administering to said subject an effective amount of an $S1P_3$ receptor antagonist and optionally a CXCR4 antagonist, wherein said CXCR4 antagonist is AMD3100:

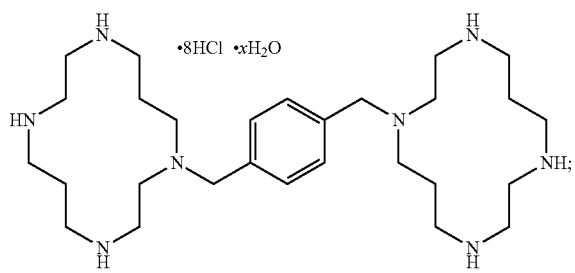

and wherein said $S1P_3$ receptor antagonist is selected from the group consisting of:

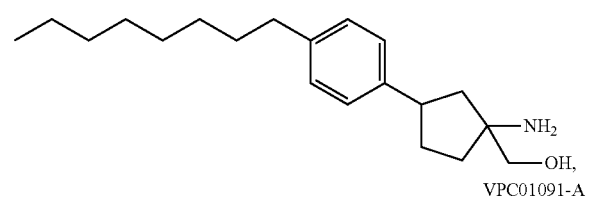

VPC01091

VPC01091-A

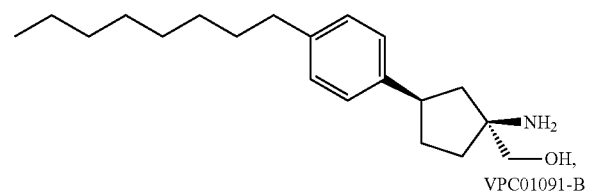

VPC01091-B

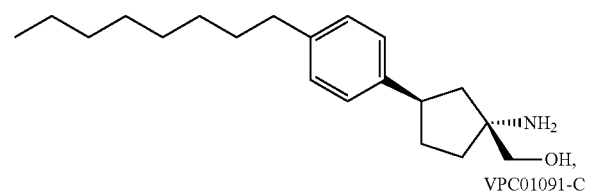

VPC01091-C

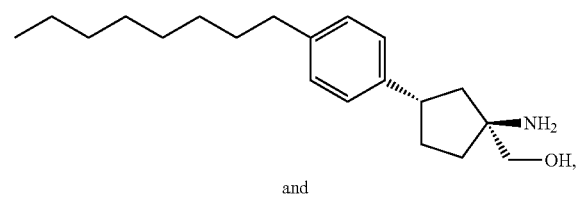

and

VPC01091-D thereby mobilizing said hemopoietic stem cells into circulation.

2. The method of claim 1, wherein an S1P receptor agonist is administered locally to recruit said mobilized hemopoietic stem cells to a wound and wherein said S1P receptor agonist is selected from the group consisting of:

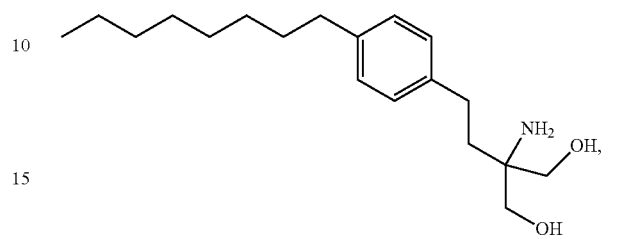

FTY720

2-amino-2-(4-octylphenethyl)propane-1,3-diol and

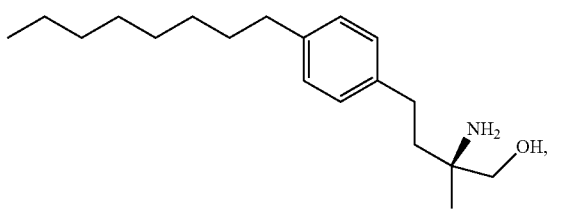

AAL151

(S)-2-amino-2-methyl-4-(4-octylphenethyl)butan-1-ol

3. The method of claim 2, where said method enhances engraftment of said mobilized hemopoietic stem cells at said wound.

4. The method of claim 1, wherein a CXCR4 antagonist is administered to said subject.

5. The method of claim 1, wherein when one $S1P_3$ receptor antagonist and one CXCR4 antagonist are administered, they are administered in one pharmaceutical composition.

6. The method of claim 5, wherein said $S1P_3$ receptor antagonist is VPC01091 and said CXCR4 antagonist is AMD3100.

7. The method of claim 6, wherein said method increases the number of stem cells in peripheral blood.

8. The method of claim 1, wherein an $S1P_3$ receptor antagonist is administered, an CXCR4 receptor antagonist is administered, and an S1P receptor agonist is administered.

9. The method of claim 1, wherein said $S1P_3$ receptor antagonist is administered more than once.

10. The method of claim 2, wherein said S1P receptor agonist is FTY720.

11. The method of claim 1, wherein said method enhances wound healing.

12. The method of claim 11, wherein said wound is a bone wound or allograft.

13. The method of claim 12, wherein said allograft is pre-coated with FTY720.

14. The method of claim 1, wherein said method enhances angiogenesis.

15. The method of claim 1, wherein said subject is human.

16. The method of claim 12, wherein said method increases the structural integrity of a bone allograft-host bone interface.

17. The method of claim 1, wherein a pharmaceutical compositions is administered to said subject, said pharmaceutical composition comprising an effective amount of said $S1P_3$ receptor antagonists and optionally an effective amount of said CXCR4 antagonists, wherein said composition comprises a pharmaceutically-acceptable carrier.

18. The method of claim 17, wherein said composition further comprises at least one purified antimicrobial agent.

19. The method of claim 17, wherein said composition is administered using a method selected from the group consisting of directly, topically, subcutaneously, and parenterally.

20. The method of claim 1, wherein said method mobilizes bone marrow cells into peripheral blood.

21. The method of claim 20, wherein said bone marrow cells are bone marrow stromal cells.

22. A method of recruiting hemopoietic stem cells, said method comprising administering to a subject an effective amount of an S1P$_3$ receptor antagonists and optionally a CXCR4 antagonist to mobilize said cells from bone marrow, and an S1P receptor agonist to recruit said cells from bone marrow, thereby recruiting cells wherein said S1P$_3$ receptor antagonist is selected from the group consisting of:

VPC01091
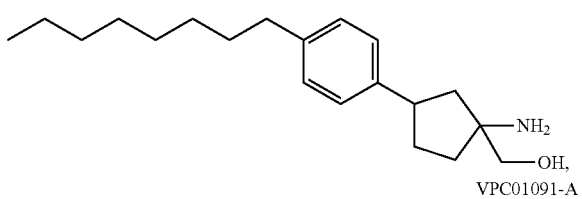

VPC01091-A
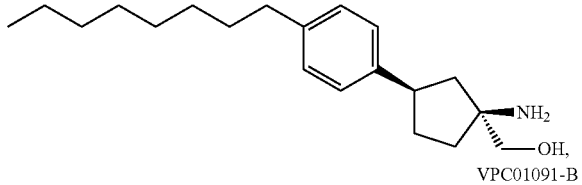

VPC01091-B
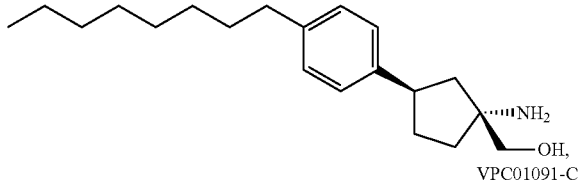

VPC01091-C
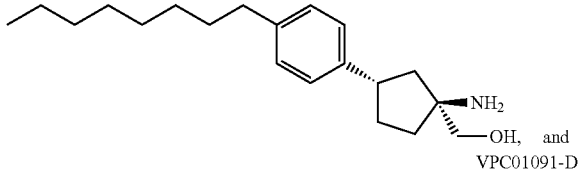

VPC01091-D
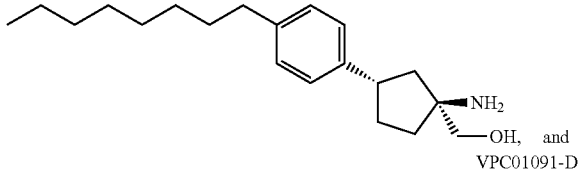 and

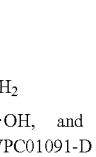

wherein said CXCR4 antagonist is AMD3100:

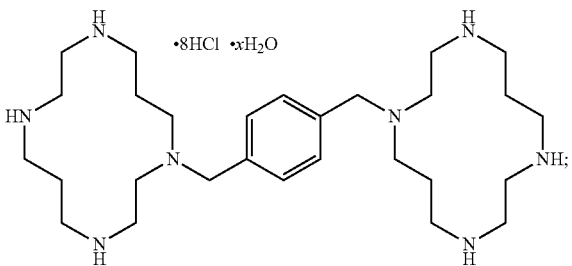 [SMILES: c1cc(CN2CCCNCCNCCCNCC2)ccc1CN1CCCNCCNCCCNCC1]

and wherein said S1P receptor agonist is administered locally and is selected from the group consisting of:

FTY720
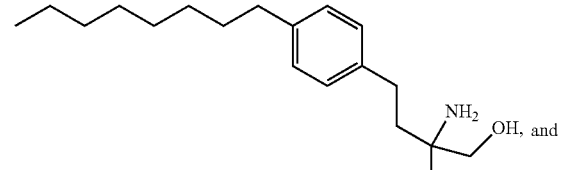

2-amino-2-(4-octylphenethyl)propane-1,3-diol

AAL151
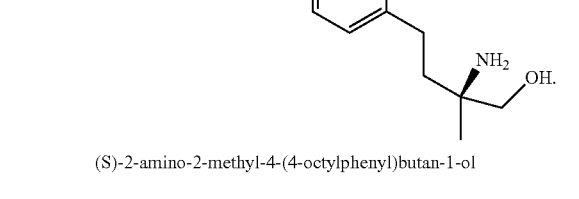

(S)-2-amino-2-methyl-4-(4-octylphenyl)butan-1-ol

23. The method of claim 22, wherein said subject is pre-treated with an S1P receptor agonist.

24. The method of claim 23, wherein said S1P receptor agonist increases migration of anti-inflammatory monocytes toward SDF-1.

25. The method of claim 23, wherein said S1P receptor agonist decreases the migration of inflammatory monocytes toward SDF-1 and S1P.

26. The method of claim 23, wherein said S1P receptor agonist is FTY720.

27. The method of claim 22, wherein said method enhances engraftment of said cells.

* * * * *